United States Patent
Binder et al.

(10) Patent No.: US 8,697,076 B2
(45) Date of Patent: Apr. 15, 2014

(54) ANTIBODIES SELECTIVE FOR PATHOLOGICAL TAU DIMERS AND PREFIBRILLAR PATHOLOGICAL TAU OLIGOMERS AND THEIR USES IN TREATMENT, DIAGNOSIS AND MONITORING OF TAUOPATHIES

(75) Inventors: Lester I. Binder, Chicago, IL (US); Daniel G. Chain, New York, NY (US); Yifan Fu, Clarendon Hills, IL (US); Kristina Patterson, Chicago, IL (US)

(73) Assignees: Northwestern University, Evanston, IL (US); Intellect Neurosciences Inc., New York, NY (US)

( * ) Notice: Subject to any disclaimer, the term of this patent is extended or adjusted under 35 U.S.C. 154(b) by 0 days.

(21) Appl. No.: 13/458,609

(22) Filed: Apr. 27, 2012

(65) Prior Publication Data

US 2012/0301473 A1 Nov. 29, 2012

Related U.S. Application Data

(60) Provisional application No. 61/479,645, filed on Apr. 27, 2011.

(51) Int. Cl.
*A61K 39/00* (2006.01)
*A61K 39/395* (2006.01)

(52) U.S. Cl.
USPC ............. 424/139.1; 424/134.1; 424/141.1; 424/142.1; 424/185.1; 514/17.7; 514/17.8

(58) Field of Classification Search
None
See application file for complete search history.

(56) References Cited

U.S. PATENT DOCUMENTS

| | | | |
|---|---|---|---|
| 2005/0054572 | A1 | 3/2005 | Marshall |
| 2008/0050383 | A1* | 2/2008 | Sigurdsson et al. ....... 424/141.1 |
| 2008/0220449 | A1 | 9/2008 | Vasan et al. |
| 2011/0312059 | A1* | 12/2011 | Moe et al. ................ 435/226 |
| 2012/0244146 | A1 | 9/2012 | Chain |
| 2012/0244174 | A1 | 9/2012 | Chain |

FOREIGN PATENT DOCUMENTS

WO WO 2011/026031 3/2011

OTHER PUBLICATIONS

Deshpande et al (2008) "Tau isoform expression and regulation in human cortical neurons" FASEB 22:2357.*
Friedhoff et al (1998) "A nucleated assembly mechanism of Alzheimer paired helical filaments" PNAS 95:15712-15717.*
Garcia-Sierra et al (2003) "Conformational changes and truncation of tau protein during tangle evolution in Alzheimer's disease" JAD 5:65,67.*
Ghoshal et al (2001) "Tau-66: Evidence for a novel tau conformation in Alzheimer's disease" J Neurochem 77:1372-1385.*
Invitrogen Product sheet "Rabbit (polyclonal) anti-oligomer antibody (A11)" accessed Apr. 18, 2013 from http://products.invitrogen.com/ivgn/product/AHB0052.*
Lang and Otvos (1992) "Immunological and conformation characterization of a phosphorylated immunodominant epitope on the paired helical filaments found in Alzheimer's disease" BBRC 187(2):783-90 (abstract only).*
Millipore "NB16 Anti-tau (Ab-1) Mouse mAb (Tau-2)" accessed Apr. 18, 2013 from http://millipore.com/catalogue/item/mab375.*
Rafii and Aisen (2009) "Recent developments in Alzheimer's disease therapeutics" BMC Medicine 7:7.*
Thermoscientific Product Sheet "Tau antibody (HT7)" accessed Apr. 18, 2013 from http://www.pierce-antibodies.com/Tau-antibody-clone-HT7-Monoclonal--MN1000.html.*
Notification of Transmittal of the International Search Report and the Written Opinion of the International Search Authority, or the Declaration issued in connection with International Application No. PCT/US2012/35514 on Dec. 10, 2012.
Written Opinion of the International Search Authority, or the Declaration issued in connection with International Application No. PCT/US2012/35514 on Dec. 10, 2012.
Davidowitz et al. Targeting tau oligomers for therapeutic development for Alzheimer's disease and tauopathies. Curr Topics Biotech. 2008, vol. 4, p. 47-64. p. 48, col. 2, and Table 1; and p. 49, Figure 1; p. 51, col. 2, 1ast para; p. 52, col. 2, lower para; and p. 54, col. 1, para 1.
Mo et al. Low Micromolar Zinc Accelerates the Fibrillization of Human Tau via Bridging of Cys-291 and Cys-322. J Biol Chem. 2009, vol. 284(50), p. 34648-57. Abstract.
Sahara et al. Assembly of two distinct dimers and higher-order oligomers from full-length tau. Eur J Neurosci. 2007, vol. 25(10), p. 3020-9. p. 3021, col. 1, para 1.
Alzforum_News, Chicago: Tau and a-Synuclein Oligomers Follow A.Beta Footsteps, Nov. 5, 2009. [Retrieved on Aug. 23, 2012]. Retrieved from the Internet: <URL: http://www.alzforum.org/new/detail.asp?id=2276> PDF file: p. 1-5. Entire documentation, especially, p. 3, para 1.
Binder et al., "Characterization of Prefibrillar Tau Oligomers in Vitro and in Alzheimer Disease," The Journal of Biological Chemistry vol. 286, No. 26, pp. 23063-23076, Jul. 1, 2011, The American Society for Biochemistry and Molecular Biology, Inc.

* cited by examiner

*Primary Examiner* — Jeffrey Stucker
*Assistant Examiner* — Adam M Weidner
(74) *Attorney, Agent, or Firm* — Davidson, Davidson & Kappel LLC

(57) ABSTRACT

Antibodies selective for pathological tau dimers and/or prefibrillar pathological tau oligomers, immunogenic peptides and epitopes of these antibodies, hydridomas producing these antibodies, uses of these antibodies, immunogenic peptides and epitopes in preparation of pharmaceutical compositions for the treatment of tauopathies, and uses of these antibodies, immunogenic peptides, epitopes and pharmaceutical compositions in the treatment of tauopathies are described. Also described are uses of these antibodies, immunogenic peptides, epitopes in diagnosis and monitoring of tauopathies.

19 Claims, 15 Drawing Sheets

ANTIBODIES SELECTIVE FOR PATHOLOGICAL TAU DIMERS AND PREFIBRILLAR PATHOLOGICAL TAU OLIGOMERS AND THEIR USES IN TREATMENT, DIAGNOSIS AND MONITORING OF TAUOPATHIES

CROSS-REFERENCE TO RELATED APPLICATIONS

This application claims priority to U.S. Ser. No. 61/479,645, filed on Apr. 27, 2011, herein incorporated by reference in its entirety.

This invention was made with government support under AG009466 awarded by the National Institutes of Health. The government has certain rights in the invention.

BACKGROUND OF THE INVENTION

The World Health Organization estimates that by 2050 there will be more than one billion people across the world that are age 65 and over. It was predicted that about half of these people will have some Tau inclusions (e.g., neurofibrillary tangles (NFT)) in their brains.

Accumulation of NFTs or other inclusions containing Tau in the brain are histopathological features of many neurodegenerative diseases, which are collectively known as tauopathies. Tauopathies include, e.g., Alzheimer's disease (AD), Pick's disease (PiD), progressive supranuclear palsy (PSP), corticobasal degeneration (CBD), and frontotemporal lobar degeneration (FTLD).

Tau is encoded by a Tau gene. It was reported that mutations in the tau gene may cause some forms of frontotemporal dementia (7-10), signifying that Tau dysfunction is sufficient to cause neurodegeneration. Moreover, pathological Tau appears to be an integral part of Aβ-induced neurotoxicity in cell culture and transgenic mouse models (3-5).

Tau pathology is thus involved and may be a cause of many tauopathies.

Therapeutic agents and compositions for therapeutic intervention in and/or prevention of tauopathies and diagnostic agents and compositions for use in diagnosis and monitoring of tauopathies may be of great value.

SUMMARY OF THE INVENTION

An object of the present invention is to provide antibodies capable of selectively recognizing a pathogenic conformation of prefibrillar pathological or neurotoxic tau and its precursors.

It is a further object of the invention to provide an isolated immunogenic peptide comprising an epitope of an antibody capable of selectively recognizing a pathogenic conformation of prefibrillar pathological or neurotoxic tau and its precursors.

It is a further object of the invention to provide epitopes of antibodies capable of selectively recognizing a pathogenic conformation of prefibrillar pathological or neurotoxic tau and its precursors, for use as immunogens or as standardizing agents in the diagnostic kits and methods.

It is a further object of the invention to provide pharmaceutical compositions (e.g., vaccines) for use in the treatment of and/or prevention of tauopathies.

It is an additional object of the invention to provide diagnostic composition for use in diagnosis and monitoring of tauopathies.

It is a further object of the invention to provide methods of preparing and using (i) the antibodies capable of selectively recognizing a pathogenic conformation of prefibrillar pathological or neurotoxic tau and its precursors and/or (ii) the isolated immunogenic peptide comprising an epitope of an antibody capable of selectively recognizing a conformation of prefibrillar pathological or neurotoxic tau and its precursors for the diagnosis of and/or for therapeutic intervention in tauopathies (e.g., Alzheimer's disease).

It is an additional object of the invention to provide methods of diagnosing, monitoring and treating tauopathies.

It is an additional object of the invention to provide hybridomas capable of producing antibodies capable of selectively recognizing a pathogenic conformation of prefibrillar pathological or neurotoxic tau and its precursors.

It is a further object of the invention to provide early diagnostic markers for tauopathies.

These objects are addressed with the present invention which relates in one aspect to the use of a pathogenic dimer comprising two tau monomers cross-linked to each other. The dimer is formed in-vitro and has a conformation which may be representative of a pathogenic conformation of a dimer formed in-vivo which may be responsible for initiating a cascade of events in which normal tau becomes directly neurotoxic or/and a chain of aggregation events leading to pathogenic prefibrillar tau oligomers, and eventually formation of NFTs. In the preferred embodiments, at least one of the cross-links between the individual tau monomers of the dimer formed in-vitro is not a disulfide bridge between cysteines of the tau monomers.

The invention identifies a precursor of prefibrillar pathological or neurotoxic tau as a pathogenic tau dimer having a conformation which is the same or similar to the conformation created by two tau monomers cross-linked to each other in-vitro by at least one cross-link which is not a disulfide bridge between cysteines of the tau monomers. Identification of such pathogenic dimers allows, e.g., for the generation of therapeutic agents and compositions for therapeutic intervention in and/or for prevention of tauopathies, and diagnostic agents and compositions for use in diagnosis and monitoring of tauopathies.

Thus, the invention is directed in part to isolated antibodies (e.g., non-naturally occurring antibodies or genetically engineered antibodies) capable of selectively recognizing pathogenic dimers and prefibrillar pathological or neurotoxic tau, including their pathogenic conformations, the pathogenic dimers and prefibrillar pathological or neurotoxic tau and precursors generally comprising two or at least two tau monomers cross-linked to each other, directly or through a linker (e.g., benzophenone-4-maleimide ("B4M"), at one or more cysteine residues. In the preferred embodiments, at least one of the cross-links between the individual tau monomers is not a disulfide bridge between cysteines of the tau monomers, the prefibrillar pathological or neurotoxic tau is prefibrillar oligomeric tau (e.g., soluble oligomeric tau) and the precursors of the oligomeric tau are dimers of tau (e.g., anti-parallel dimers of tau). These antibodies may identify, neutralize or promote clearance of the pathological tau and its precursors. These antibodies may therefore reduce or eliminate toxicity of the pathological tau and its precursors and/or slow down or prevent aggregation of the pathological tau into insoluble filaments. These antibodies may also lower the amount of pathogenic tau and its precursors in the brain and CSF fluid of a mammal, and may delay or prevent memory decline and other symptoms of tauopathies, including symptoms of AD, in the mammal. Because these antibodies are selective for the pathological tau and its precursors, these antibodies are not expected to affect biological functions of normal tau in vivo.

These antibodies may also allow for early detection of tauopathies (e.g., AD), e.g., at least 10 years before signs of cognitive decline or dementia appear and before NFTs begin to form, because these antibodies selectively recognize tau dimers, or their pathogenic conformations, which begin to appear in mammals suffering from or at risk of developing a tauopathy (e.g., AD) at least 10 years before NFTs begin to form and symptoms of dementia begin to appear.

The invention is also directed in part to an isolated immunogenic peptide (e.g., a genetically engineered peptide) comprising an epitope of an antibody capable of selectively recognizing prefibrillar pathological or neurotoxic tau and precursors thereof, including their pathogenic conformations, wherein the prefibrillar pathological or neurotoxic tau and precursors comprise at least two tau proteins cross-linked to each other, directly or through a linker (e.g., B4M), at one or more cysteine residues. In the preferred embodiments, at least one of the cross-links between the individual tau monomers is not a disulfide bridge between cysteines of the tau monomers. The immunogenic peptide of the invention is capable of inducing a production of the antibodies (e.g., i.e., non-naturally occurring antibodies or genetically engineered antibodies) capable of selectively recognizing the prefibrillar pathological or neurotoxic tau and precursors thereof in a mammal, upon administration to the mammal. These antibodies may be used for therapeutic intervention in and/or prevention of tauopathies (e.g., AD), and/or as diagnostic agents. These antibodies are suitable for and may be incorporated in compositions for use in diagnosis and monitoring of tauopathies (e.g., AD). These antibodies may also be used in the preparation of the medicaments for use in treatment and/or prevention of tauopathies (e.g., AD) and/or in the preparation of diagnostic agents for diagnosis and monitoring of tauopathies (e.g., AD).

The invention encompasses methods of preparing the antibodies capable of selectively recognizing prefibrillar pathological or neurotoxic tau and precursors thereof, and/or their pathogenic conformations; and methods of preparing the immunogenic peptides comprising an epitope of an antibody capable of selectively recognizing prefibrillar pathological or neurotoxic tau and/or a precursor thereof. These methods encompass both in situ and ex situ production of the antibodies capable of selectively recognizing prefibrillar pathological or neurotoxic tau and its precursors, including their pathogenic conformations.

The invention also encompasses hybridomas producing the antibodies capable of selectively recognizing prefibrillar pathological or neurotoxic tau and precursors thereof, and uses of these hybridomas in production of antibodies for use in the preparation of pharmaceutical compositions and/or diagnostic compositions.

The invention is further directed to pharmaceutical compositions comprising one or more antibodies (e.g., i.e., non-naturally occurring antibodies or genetically engineered antibodies) capable of selectively recognizing prefibrillar pathological or neurotoxic tau and precursors thereof, including their pathogenic conformations, and pharmaceutical compositions comprising immunogenic peptides comprising epitopes of the antibodies capable of selectively recognizing prefibrillar pathological or neurotoxic tau and precursors thereof, including their pathogenic conformations. These compositions may be used for therapeutic intervention in and/or prevention of tauopathies, including AD.

For example, in one aspect, the invention is directed to a vaccine comprising the antibodies capable of selectively recognizing the prefibrillar pathological or neurotoxic tau and precursors thereof, including their pathogenic conformations, or/and the immunogenic peptides comprising epitopes of the antibodies capable of selectively recognizing prefibrillar pathological or neurotoxic tau and precursors thereof. The vaccine may include one or more additional active agents (e.g., antibodies and/or immunogens) for the treatment or prevention of tauopathies, including AD.

The invention is also directed to the administration to a subject in need of therapy for a tauopathy (e.g., AD) of a therapeutically effective dose of the antibodies capable of selectively recognizing prefibrillar pathological or neurotoxic tau and precursors thereof, and/or their pathogenic conformations, or/and of the immunogenic peptides comprising epitopes of the antibodies capable of selectively recognizing prefibrillar pathological or neurotoxic tau and precursors thereof. Administration of these active agents is expected, e.g., to delay or reduce tau pathology in mammals suffering from or at risk of developing a tauopathy and/or improve cognitive function in these mammals. Administration of these active agents is also expected to neutralize and/or promote clearance of the pathological tau and its precursors, reduce or eliminate toxicity of the pathological tau and its precursors and/or slow down or prevent aggregation of the pathological tau into insoluble filaments, all without affecting the biological functions of normal tau. Thus, administration of these agents is expected to delay or prevent memory decline and other symptoms of tauopathies, including symptoms of AD in these mammals.

The invention is also directed to a method of treating or preventing a tauopathy, the method comprising administering a therapeutically effective amount of an immunogen comprising at least two tau proteins cross-linked to each other, directly or through a linker (e.g., B4M), at one or more cysteine residues, and/or the antibodies capable of selectively recognizing prefibrillar pathological or neurotoxic tau and precursors thereof, to a mammal with a tauopathy (e.g., AD) or at risk of developing the tauopathy. In the preferred embodiments, at least one of the cross-links between the individual tau monomers is not a disulfide bridge between cysteines of the tau monomers. Administration of the immunogen is expected to induce production of the antibodies (e.g., i.e., non-naturally occurring antibodies or genetically engineered antibodies) capable of selectively recognizing prefibrillar pathological or neurotoxic tau and precursors thereof in the mammal. The production of the antibodies or administration of these antibodies is expected, e.g., to delay or reduce tau pathology in mammals and/or improve cognitive function in mammals suffering from a tauopathy. These antibodies are also expected to neutralize and/or promote clearance of the pathological prefibrillar tau and its precursors, reduce or eliminate toxicity of the pathological prefibrillar tau and its precursors and/or slow down or prevent aggregation of the pathological prefibrillar tau into insoluble filaments, all without affecting the biological functions of normal tau. Administration of these antibodies is thus expected to delay or prevent memory decline and other symptoms of tauopathies, including symptoms of AD.

The invention is also related to an immunization of a mammal comprising administering a therapeutically effective dose of the antibodies capable of selectively recognizing prefibrillar pathological or neurotoxic tau and precursors thereof, including their pathological conformations, or/and of immunogenic peptides comprising epitopes of antibodies capable of selectively recognizing prefibrillar pathological or neurotoxic tau and precursors thereof, to the mammal.

The invention is also directed to methods of inducing an immunologic response in a mammal comprising administering a therapeutically effective dose of an immunogenic peptide(s) comprising epitope(s) of the antibodies capable of selectively recognizing prefibrillar pathological or neurotoxic tau and precursors thereof to the mammal.

The invention is further directed to diagnostic compositions comprising one or more antibodies capable of selectively recognizing prefibrillar pathological or neurotoxic tau and precursors thereof, including their pathogenic conformations. The diagnostic compositions may be used in the diagnosis and monitoring of tauopathies (e.g., AD). For example, these diagnostic compositions may be used to measure a degree of association of the pathogenic tau dimers and prefibrillar pathogenic tau oligomers with the antibodies, and subsequently quantifying the amount of pathogenic oligomers and dimers in a mammal or determining a stage of pathology based on this association. These diagnostic compositions may also be used to identify mammals starting to develop a tauopathy (e.g., AD) well before these mammals begin to show signs of cognitive decline and dementia (e.g., at least 10 years before signs of dementia begin to appear).

The invention is additionally directed to diagnostic methods utilizing the antibodies capable of selectively recognizing prefibrillar pathological or neurotoxic tau and precursors thereof, including their pathogenic conformations, immunogens of these antibodies and/or epitopes of these antibodies.

The invention is further directed to early diagnostic markers of tauopathies.

The invention also encompasses methods of preparing stabilized dimers of tau protein by crosslinking at least two monomers to each other, directly or through a linker (e.g., benzophenone-4-maleimide ("B4M"), at one or more cysteine residues; and uses of these dimers in diagnosis, monitoring or treatment of tauopathies and preparations of compositions for use in diagnosis, monitoring or treatment of tauopathies.

DEFINITIONS

The term "antibody" as used in the present application includes whole antibodies and binding fragments/segments thereof.

The terms "does not bind," "does not recognize," and "does not show reactivity" as used in the present application mean either that an antibody show no detectible binding or reactivity with a peptide or protein (e.g., hTau40 or its recombinant form) in-vitro, defined as having an equilibrium constant KD with the peptide or protein of from $1\times10^{-4}$ M to $1\times10^{-6}$ M, and as determined for example when tested at the saturating level of antibody-immunogen binding using 0.1 µg/ml of the antibody on a dot blot with 50 ng of the peptide or protein.

The terms "binds selectively," "selectively recognize," "selectively recognizes," "selectively recognizing," "having selectivity," and "selective for" as used in the present specification mean that an antibody is at least seven times more likely to bind the antigen it is selective for (e.g., a pathogenic tau dimer) than other proteins or peptides, when tested using immunogold labeling using 0.4 µg/ml of the purified antibody. In the preferred embodiments, the antibody has an equilibrium constant KD with the antigen it is selective for of from $1\times10^{-9}$ M to $1\times10^{-11}$ M in-vitro; and has an equilibrium constant KD with other peptides or proteins (e.g., htau40) which is from $1\times10^{-4}$ M to $1\times10^{-6}$ M or shows no detectible binding or reactivity with these other peptides or proteins in-vitro, when tested at the saturating level of antibody-immunogen binding using 0.1 µg/ml of the antibody on a dot blot with 50 ng of the peptide or protein.

The term "conformation" means a three-dimensional form of a peptide or protein (e.g., a secondary structure of the peptide or protein).

"Conformation selective antibody" as used in the present specification means that the antibody is selective for the specific conformation (e.g., secondary structure of the antigen). A conformation selective antibody would not recognize the amino acid sequence of its antigen when that sequence is not in the conformation selectively recognized by the antibody, when tested at the saturating level of antibody-immunogen binding using 0.1 µg/ml of the antibody on a dot blot with 50 ng of antigen.

The term "filament(s)" refers to structure(s) of tau aggregates which is (are) greater than 50 nm in length. "Filaments" include NFTs.

The term "human antibody" in the present application includes antibodies having variable and constant regions derived from human immunoglobulin sequences. The term "human antibody," as used in the present application, does not include antibodies in which CDR sequences from another mammalian species, e.g., a mouse, have been grafted onto human framework sequences.

The term "humanized antibody" as used in the present application refers to antibodies which comprise heavy and light chain variable region sequences from a non-human species (e.g., a mouse) but in which at least a portion of the $V_H$ and/or $V_L$ sequence has been replaced with a corresponding portion from a human immunoglobulin sequence.

The term "oligomer(s)" as used in the present application refers to tau aggregates which are less than 50 nm in length and which are intermediates between monomers of Tau and NFTs. The term "oligomer(s)" does not include monomers of tau (e.g., hTau40), dimers of tau and NFTs.

The terms "tau protein" and "tau monomer" as used in the present application refers to any one of known isoforms of tau (e.g., hTau40, the longest isoform of human microtubule associated protein tau containing all alternatively spliced inserts).

The terms "immunogen" refers to a molecule capable of being bound by an antibody, a B cell receptor (BCR), or a T cell receptor (TCR) if presented by MHC molecules. The term "immunogen," as used herein, also encompasses T-cell epitopes. An immunogen can additionally be capable of being recognized by the immune system and/or being capable of inducing a humoral immune response and/or cellular immune response leading to the activation of B- and/or T-lymphocytes. This may, however, require that, at least in certain cases, the immunogen contains or is linked to a T helper cell epitope and is given an adjuvant. An immunogen can have one or more epitopes (e.g., B- and T-epitopes). The "immunogen" as used herein may also be mixtures of several individual immunogens. The term "immunogen" encompasses, but is not limited to an isolated immunogenic peptide.

The term "prefibrillar pathological or neurotoxic tau" includes pathological or neurotoxic tau oligomers and dimers, and excludes NFTs.

The term "substantially" in the context of antibody recognition means that any binding of the antibody to its antigen that may be exhibited is insufficient to affect normal functions of the antigen in vivo.

The term "tauopathy" refers to tau-related disorders or conditions, e.g., Alzheimer's Disease, Progressive Supranuclear Palsy (PSP), Corticobasal Degeneration (CBD), Pick's Disease, Frontotemporal dementia and Parkinsonism associated with chromosome 17 (FTDP-17), Parkinson's disease, stroke, traumatic brain injury, mild cognitive impairment and the like.

The abbreviation "AA" means "arachidonic acid."
The abbreviation "Aβ" means "amyloid β."
The abbreviation "AD" means "Alzheimer disease."
The abbreviation "B4M" means "benzophenone-4 maleimide."
The abbreviation "MTBR" means "microtubule binding repeat."
The abbreviation "NFT" means "neurofibrillary tangle".
The abbreviation "SELDI-TOF" means "surface enhanced laser desorption and ionization time of flight."
The abbreviation "TOC1" means "Tau oligomeric complex-1 antibody."
The abbreviation "TR" means "Thiazin Red."

BRIEF DESCRIPTION OF THE DRAWINGS

FIG. 1A shows photochemical cross-linking performed by incubating soluble Tau with B4M. Full-length Tau (i.e., hTau40) possesses two native cysteine (Cys) residues located in the 2nd and 3rd MTBRs. After conjugating the maleimide moiety of B4M to the native cysteines (Cys*), aggregation of Tau was induced using arachidonic acid ("AA"), and the resultant Tau aggregates were cross-linked with short-wave UV light. Aggregation-competent Tau is depicted in the Alz-50 conformation in which the N terminus comes into close proximity of the MTBR region (35). The circles indicate potential cross-linked sites. FIG. 1B shows EM of aggregated Tau with no cross-linker and no UV treatment. Scale bar is 200 nm. FIG. 1C shows that EM of B4M-conjugated Tau UV irradiated for 5 min is morphologically identical to untreated Tau. FIG. 1D shows Western blot of cross-linked Tau filaments and controls. Cross-linking of Tau aggregates reveals an apparent 180-kDa multimer, as well as larger cross-linked products. Note the background levels of the 180-kDa multimer in the absence of cross-linking. 500 ng of Tau was loaded per lane and blotted with R1. Results are representative of five independent experiments.

FIG. 3A shows cross-linked hTau40 aggregates concentrated and separated by 505-PAGE. Monomer and oligomer bands were extracted and electroeluted and then run on 505-PAGE followed by staining with Coomassie Brilliant Blue R-250 to verify separation. FIG. 3B is SELDI-TOF MS analysis of Tau monomer and reveals a peak at 47 kDa, the mass of hTau40. Additionally, minor peaks at 94 and 141 kDa were observed. FIG. 3C is SELDI-TOF MS analysis of the apparent 180-kDa Tau oligomer and reveals the prominent peak as 94 kDa, which corresponds to a dimer. Noticeably, a large Tau monomer peak is also present, likely representative of uncross-linked 50S-stable dimers that have since become dissociated. Monomer+ 2 charge peaks are denoted by arrows.

FIG. 4A shows Tau cross-linked at defined time points after the addition of AA. Note that dimer cross-linking saturates 0.25 hours after the onset of aggregation. Corresponding EMs demonstrated that long filaments did not emerge until after dimer formation has already saturated. FIG. 4B depicts EMs of purified dimer (4 μM total Tau equivalent to 2 μM dimeric Tau) and monomer (2 μM) 24 hours after the addition of AA and demonstrated that dimer aggregation produced mostly oligomers and a few short filaments (arrows). Conversely, electroeluted monomer formed long filaments in addition to oligomers when induced to aggregate with AA. Protein loading was 500 ng/lane blotted with R1. Scale bars in FIG. 4A and FIG. 4B are 200 nm.

FIG. 5A shows dot blot demonstrating TOC1 immunoreactivity. It shows that TOC1 preferentially (i.e., selectively) labels uncross-linked Tau oligomeric and filamentous aggregates prepared with AA as opposed to unaggregated Tau (−AA). Moreover, it shows that TOC1 did not react with either α-synuclein (αS) or Aβ in the monomeric, oligomeric, or filamentous states. 45 ng/spot was applied to the nitrocellulose. Total Tau was determined using Tau12. FIG. 5B shows quantification of TOC1 and Tau12 immunoreactivity at varying Tau concentrations. Whereas, Tau12 (gray dashed line) demonstrates a high affinity for both unaggregated (0) and aggregated (●) Tau, TOC1 (black solid line) reacts exclusively with Tau aggregates. Each point represents a minimum of three independent measurements. FIG. 5C shows EMs of Tau oligomers and filaments (Tau Olig+Fil), α-synuclein oligomers and filaments (αS Olig+Fil), Aβ oligomers (Aβ Olig), and Aβ filaments (Aβ Fil) confirm the generation of aggregates of the appropriate morphology for each protein. Scale bar is 200 nm. FIG. 5D shows that TOC1 preferentially reacts with Tau dimers on dot blots. Monomeric and dimeric Tau were isolated from the same aggregation reaction. Also included is an electroeluted monomeric sample that was never exposed to AA (−AA). 12 ng/spot was applied to the nitrocellulose.

FIG. 6A shows TOC1 immune-gold labeling which revealed preferential labeling of oligomeric structures. Labeling of the ends of a few filaments was observed as well (arrow). FIG. 6B shows higher magnification of TOC1 immunogold labeling. FIG. 6C is immunogold labeling of the poly-His tag which revealed abundant labeling of both Tau oligomers and filaments. FIG. 6D is quantification of TOC1 immunogold labeling of filaments (>50 nm) and oligomers (<50 nm) relative to His tag immune-gold labeling of structures of the same category.*, p<O.Q1, paired t test. Scale bars are 100 nm.

FIG. 7A is schematic representations of the deletion mutants utilized. FIG. 7B is EM of wild type (WD, $A^{9-155}$, $A^{273-305}$, $A^{144-273}$, $A^{291-349}$, and $A^{321-441}$). hTau40 was used to confirm the presence of aggregates. The morphological characteristics of the other deletion mutants were described elsewhere (30, 36, 37, 53). Scale bar is 500 nm. FIG. 7C is immunoreactivity of TOC1 to deletion mutants of hTau40 expressed as the ratio of TOC1:

total Tau. Total Tau was measured with eitherTau12 or a H is probe antibody. Results were normalized to WT hTau40. Each bar represents the average of three independent experiments with the exception of MTBR (n=2). The proposed discontinuous epitope of TOC1 consisted of residues 155-244, or a fragment(s) thereof, (Site 1) and residues 376-421, or a fragment(s) thereof, (Site 2) and was represented schematically in panel A.*, p<0.05;, p<0.01; *, p<0.001, one-way analysis of variance; ND, p value not determined. FIG. 7D is the discontinuous epitope of TOC1, its preferential binding (e.g., selective binding) to dimeric over monomeric Tau are consistent with an antiparallel dimer conformation. The gray shaded box represents the MTBR, and the proposed TOC1 epitope is circled.

FIG. 8A shows TOC1 preferentially (i.e., selectively) labeling Tau in AD brains, compared with that from controls in non-denaturing conditions on dot blots (580 ng/spot), indicating that Tau in the TOC1 conformation is more abundant in AD. FIG. 8B is a quantification of TOC1 labeling in extracts from the frontal cortex of control and AD brains in A represented as TOC1:Tau12 ratios.*, p<0.01, unpaired t test. FIG. 8C depicts that the superior temporal gyrus (STG) does not contain TOC1 immunoreactive Tau pathology in control cases (Braak I and II). FIG. 8D depicts that, in the entorhinal cortex (EC) of control cases, TOC1 labels early pretangle neurons with staining extending into both apical and basal dendritic processes. In addition, neuropil threads are labeled with TOC1. FIG. 8E is higher magnification of TOC1-labeled pretangle neuron in the EC from a control case and reveals that these neurons do not contain mature compact NFTs. FIG. 8F shows that TOC1 labels abundant pathology in the STG of AD cases (Braak V. and VI), including neuropil threads, neuritic plaques, as well as pretangle and tangle-bearing neurons. FIG. 8G shows that, in the EC of AD cases, TOC1 labels similar pathology in addition to neurons that have lost their dendritic processes indicating that they are further along in the process of tangle evolution. FIG. 8H is a higher magnification of TOC1 staining of the EC in AD. FIG. 8I is a low magnification TOC1 immunostaining of the hippocampus of an AD case. FIG. 8J shows that TOC1 immunostaining in the CA1 region of the hippocampus in AD reveals flame-shaped inclusions within pyridimal neurons that are characteristic of this region. FIG. 8K is a higher magnification of TOC1 immunolabeling of a neuritic plaque and pyramidal neurons in the CA1 region of an AD case. Scale bars are 50 μm.

FIGS. 9A and 9B show laser scanning confocal microscopy used to determine the degree of colocalization between TOC1 (green) and pS422 (red) in the entorhinal cortex. Colocalization between the two antibodies was almost complete in both control (A) and AD (B) cases, indicating that formation of the TOC1 epitope correlates with phosphorylation of Ser422, an early event in AD pathogenesis. FIG. 9C shows immunofluorescence which was performed using TOC1 (green) and MN423 (red) in severe AD cases. Very little colocalization was observed. FIG. 9D shows that, in severe AD cases, TOC1 and TR did not colocalize, indicating that the TOC1 epitope precedes β-sheet formation characteristic of NFTs. Although occasional inclusions with both TOC1 and TR exist (arrow), different portions of the cell are labeled by each. Scale bar is 50 μm.

FIG. 10A shows that increased UV time resulted in an increase in the quantity of cross-linked oligomeric species; however, the migration of these oligomeric species did not change. FIG. 10B shows that the concentration of tau used in the polymerization reaction did not affect the composition of the cross-linked products. FIG. 10C shows that varying the concentration of AA used in the aggregation reaction affected the amount but not the composition of the cross-linked products. Cross-linked aggregation reactions were conducted with 8 μM tau, 75 μM AA, and 300 seconds UV irradiation time except where otherwise indicated. 500 ng/lane was loaded on SDS-PAGE and transferred to nitrocellulose prior to blotting with the R1 polyclonal anti-tau antibody.

FIG. 11A shows SELDI-TOF MS analysis of the 180 kDa cross-linked product and reveals a prominent peak as 94 kDa, corresponding to a tau dimer. Minor peaks at 141 kDa (trimer) and 188 kDa (tetramer) are also present. Thus, the apparent 180 kDa multimer is not a trimer nor a tetramer but, in fact, a dimer. FIG. 11B shows SELDI-TOF MS analysis performed without multiple sample applications (sample bound to the chip with the bioprocessor module) and omitting formic acid in the matrix solution. Under these milder conditions, the data collected was almost identical to that in panel A (above) with the exception of reduced overall signal intensity. Monomer+2 charge peak is denoted with an arrow. Data were collected at a laser energy of 4400J with a mass range between 10-220 kDa.

FIGS. 14A-14E are negatively stained EM images of tau fractions after sucrose gradient centrifugation. FIGS. 14F-14J show TOC1 Immunogold labeling with negatively stained EM. Fraction 1. (A,F) through Fraction 5 (E,J). Figure K shows Dot Blots using Tau7 and TOC1 antibodies on 50 ng of protein from each fraction. FIG. 14L shows Dot Blot Densitometry graph comparing the TOC1:Tau7 ratio for each fraction of Example 3. Scale bar=200 nm.

FIGS. 15A-15C are negatively stained EM images of tau in the absence of arachidonic acid (−AA) or in its presence after 15 minutes or 6 hours of aggregation. FIGS. 15D-15F show TOC1 Immunogold labeling with negatively stained EM on the same aggregate preparations. Scale bar=200 nm.

DETAILED DESCRIPTION

Figure 1:
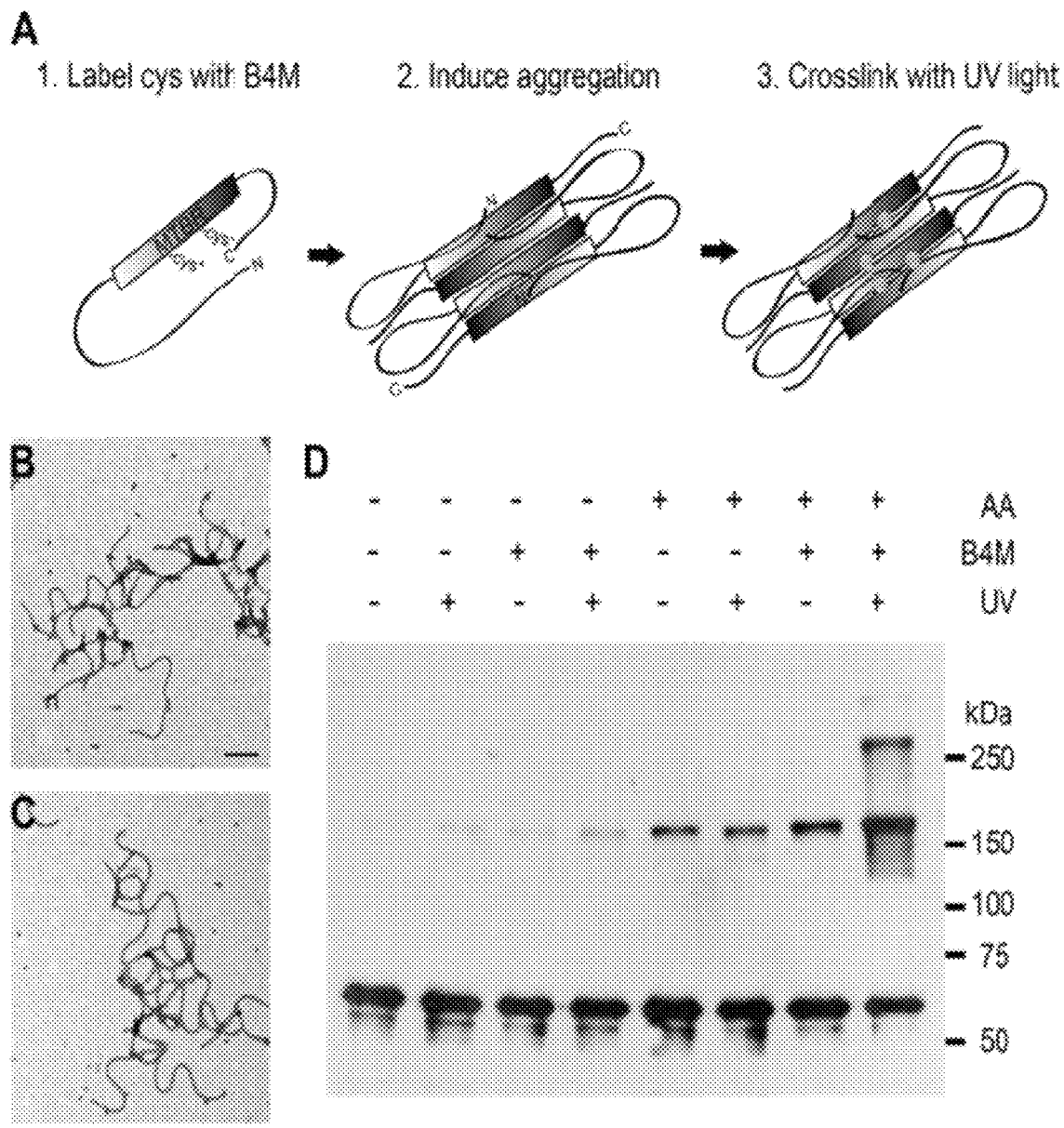
FIGS. 1A to 1D depict cross-linking Tau aggregates with B4M cross-linkers.

Pathological aggregation of the microtubule-associated protein Tau and accumulation of neurofibrillary tangles (NFT) or other inclusions containing Tau are defining histopathological features of tauopathies. NFTs usually appear in the cortex of a mammalian brain in a reproducible pattern. The location of NFTs usually provides information with regard to its age or stage of maturation.

A common feature of tauopathies is neuronal cell degeneration. Neuronal cell degeneration is a very slow, multi-stage process of cumulative neuronal cell dysfunction that culminates in cell death. In degenerating cells, signal transduction between neuronal cells across the intercellular gap, or synapse, begins to deteriorate many years before neuronal cell death occurs. Initially, Tau proteins aggregate, next Tau tangles form and eventually cell death is seen. The progression of a patient through these phases correlates strongly with loss of memory and cognitive decline.

One tauopathy is Alzheimer's disease (AD).

Alzheimer's Disease

AD is a common chronic progressive neurodegenerative disease in which there is neuronal cell degeneration and an irreversible loss of cognitive and behavioral functions.

AD can persevere for over 10 years, advancing from mild symptoms to extremely severe manifestations. AD is said to afflict approximately 10% of the population over the age of 65, and more than 30% of the population over the age of 80.

The predominant initial clinical symptom of AD is the impairment of memory, although a wide range of other higher functions, such as personality and judgment, are also affected. Yet in very early, asymptomatic AD, pre-tangle Tau aggregates may be or are already present in the entorhinal cortex and hippocampus regions of the brain. These are the same regions where neuronal degeneration and loss of neuronal cells occurs later as the disease progresses. With time, Tau tangles also form in the parieto-temporal and frontal region of the cortex resulting in neuronal dysfunction and correlating with the worsening of clinical symptoms.

The severity and progression of AD is characterized by Braak stages, using a tool described by Braak in Tau Aggregates Correlate with Cognitive Impairment During the 1990s. Braak graded the presence, distribution and density of Tau tangles in the brain and defined six distinct stages of AD progression ("Braak stages"). Braak stage is a measure of where and how many tangles there are in the brain.

Braak stage I is the point at which tau protein starts to clump into tau tangles. At this stage, the tau tangles have begun to form in the transitional entorhinal region of the brain, which is a "relay station" between the cortex and the hippocampus, and is critical for memory. There are no external symptoms at this stage, and may take a number of years (e.g., 10 to 15 years) before any symptoms (e.g., dementia) are noticed.

By Braak stage II, tau tangles have accumulated further and have caused some neurons to burst apart and die. At this stage, the tau tangles are much more extensive in the transitional entorhinal region and have begun to kill neurons there. At the same time, tau protein began to accumulate in the brain's hippocampus and neo-cortex, but has not yet formed tangles. However, mental testing at this stage still shows minimal impairment.

By Braak stage III, the tau tangles have begun to cause extensive neuronal death. A proposed mechanism for neuronal death is that the tau tangles grow out of control. Tau tangles fill up the neuron, causing its membrane to burst. Although, at this stage, tau tangles and neuronal death have likely caused some memory impairment, only about ten percent of patients at this stage will be diagnosed as suffering from dementia.

By Braak stage IV, even though the tau tangles still occupy only a small portion of the brain, tau tangles have caused significant memory and cognitive impairment. By this stage, the tau tangles have formed extensively in the transitional entorhinal region and the hippocampus, where they have caused neuronal death, and the tangles are starting to form in neo-cortex. Neo-cortex is the largest part of the brain and is involved in higher functions such as sensory perception, conscious thought and language. Seventy percent of patients with this level of tangles in their brain will be diagnosed as suffering from dementia.

By Braak stage V, the tau tangles have caused extensive neuronal death, giving rise to severe memory and cognitive impairment. Tangles have formed extensively in the transitional entorhinal region, the hippocampus (which is critical for memory), and the neo-cortex. About eighty percent of patients with this level of tangles will be diagnosed as suffering from moderate to severe dementia. They will be completely unable to take care of themselves and will have trouble recognizing family members.

AD is also characterized by the extracellular accumulation of plaques composed of amyloid β(Aβ) and the intracellular accumulation of the microtubule-associated protein Tau into neurofibrillary tangles (NFTs). Aβ plaques are generally preceded by formation of pathogenic amyloid beta dimers, oligomers and fibrils outside the cell.

There also appears to be a potential link between amyloid beta aggregation and Tau pathology. Several studies have established that Aβ oligomers increase phospholipase A2 activity, which in turn elevates AA resulting in neuronal toxicity (81-83). Increased activity of cytoplasmic phospholipase A2 has been confirmed in AD, generating increased levels of free fatty acids including AA (84). Interestingly, reduction of phospholipase A2 ameliorates cognitive deficits in an amyloid precursor protein mouse model of AD (83). In the same model, reduction of endogenous Tau also prevented behavioral deficits (4). These findings suggest that AA and Tau may work synergistically. Examples below provide evidence that AA-stimulated Tau aggregation is relevant to AD, suggesting that the liberation of free fatty acids including AA is a potential link between Aβ and Tau pathology.

NFTs are composed of Tau aggregates in the form of paired helical filaments and straight filaments (62, 63). Unlike Aβ plaques, the spatial and temporal progression of NFTs positively correlates with the progression of clinical symptoms (1, 2).

Although the spatiotemporal distribution of NFTs correlates with neuron loss and cognitive impairment in AD, current evidence suggests that NFTs may not be the primary form of Tau underlying neuronal dysfunction. For instance, the amount of neuronal loss greatly surpasses the amount of tangle formation in AD (64). Furthermore, neuronal loss and cognitive deficits precede neurofibrillary pathology in transgenic mouse models (20, 21). Consequently, it has been proposed that prefibrillar Tau aggregates may be responsible for a large part of disease-related neurotoxicity. To this effect, prefibrillar Tau aggregates correlate with cognitive dysfunction in a tauopathy mouse model, and similar multimeric Tau species were found in AD (25).

Recent evidence indicates that neuronal dysfunction precedes the formation of these insoluble fibrillar deposits, suggesting that earlier prefibrillar Tau aggregates may be neurotoxic. For example, overexpression of both wild type and mutant Tau induces neurodegeneration in various animal models (14-19); however, memory deficits and cell loss precede detectable NFT-like Tau pathology (20, 21). Moreover, suppression of Tau expression improves memory function and halts further cell loss yet NFTs persist, suggesting that neurofibrillary pathology; however, memory deficits and cell loss precede detectable NFT-like Tau pathology (20, 21). Moreover, suppression of Tau expression improves memory function and halts further cell loss yet NFTs persist, suggesting that neurofibrillary pathology is not sufficient for neurodegeneration (22, 23). Importantly, neurodegeneration occurs in some animal models overexpressing Tau despite the absence of overt neurofibrillary pathology (19, 24). Thus, NFTs may not be required for and may not be the primary cause of neurotoxicity and cognitive dysfunction. In fact, levels of early Tau multimeric aggregates that preceded NFTs correlated with memory deficits in transgenic mice that overexpress Tau (25). Collectively, these studies strongly suggest that an intermediate Tau aggregate preceding NFT formation may be responsible for neuronal dysfunction observed in AD and other tauopathies.

The present invention, in one aspect, identifies prefibrillar Tau aggregates, including their conformations, which may be neurotoxic and may contribute to the pathology of a tauopathy (e.g., AD), and describes a proposed mechanism for formation of the NFTS and neurodegeneration.

The examples that follow describe a study in which prefibrillar Tau aggregates that may be associated with disease-related cognitive decline in AD, including their conformation, were identified and characterized. In this study, using arachidonic acid ("AA") combined with a photochemical cross-linking technique, Tau multimers that approximate those seen in AD, and believed to have a pathogenic conformation which approximate the one seen in AD, were analyzed by SDS-PAGE. It was demonstrated that dimerization is an early event in the Tau aggregation process, and that the described dimers are building blocks for prefibrillar oligomeric species. Furthermore, the first glimpse of Tau oligomers within the context of early AD pathology was provided, using a novel antibody selective for a dimer comprising at least two tau proteins cross-linked to each other at one or more cysteine residues, through a linker consisting of B4M radical, including its conformation.

In AD, Tau is cross-linked by transglutaminases and products of lipid peroxidation such as hydroxynonenal (product of AA peroxidation), and these modifications may even promote Tau aggregation by stabilizing AD-associated Tau conformations such as Alz-50 (74-79). Although it is likely that Tau dimerization occurs under physiological conditions, the process may become dysregulated in disease. Formation of stable cross-links may be one mechanism by which the equilibrium shifts away from soluble, monomeric Tau toward Tau aggregates.

AD is also characterized by the presence of both Aβ and Tau inclusions. Tau appears to be necessary (e.g., appears to precede or initiate) toxicity of Aβ in both cultured cells and transgenic mice (3, 4). Therefore, elucidating the mechanism by which Tau converts from a soluble, micro-tubule-bound protein into stable, toxic aggregates appears to be a key to understanding this disease. One such mechanism is described below.

Proposed Mechanism for Tau Aggregation

An emerging view is that NFT themselves are not the true toxic entity in tauopathies; rather, prefibrillar aggregates of a size intermediate between monomers and NFT are pathogenic.

A proposed mechanism for Tau aggregation according to the present invention involves formation of a pathogenic dimer comprising two tau monomers cross-linked to each other. The dimer has a pathogenic conformation and may be directly neurotoxic or/and may initiate a chain of aggregation events leading to the formation of NFTs. The dimer may be a precursor of the prefibrillar pathological or neurotoxic tau and formation of NFTs. The prefibrillar pathological or neurotoxic tau may be an oligomer comprising these dimers.

It was demonstrated in the examples below that Tau dimers of the invention (e.g., dimers comprising two tau monomers cross-linked to each other with apparent kDa of 180), including their pathogenic conformations, are aggregation intermediates in the formation of higher order oligomers. Interestingly, these oligomeric aggregates are markedly elevated in the advanced stages of AD (e.g., Braak Stage VI), but not during early stages (e.g., Braak Stage I). Identification of this pathological tau and its precursors by the inventors allows, e.g., for generations of therapeutic agents, and preparations of compositions for therapeutic intervention in and/or prevention of tauopathies and diagnostic agents and compositions for use in diagnosis and monitoring of tauopathies.

In the examples below, a monoclonal antibody that selectively recognizes pathogenic Tau dimers, including their pathogenic conformation, and which may also recognize higher order pathogenic oligomeric aggregates of Tau, including their pathogenic conformation, was generated. This antibody however shows no reactivity with NFTs and no reactivity with tau monomers in-vitro, when tested at the saturating level of antibody-immunogen binding using 0.1 μg/ml of the antibody on a dot blot with 50 ng of the peptide or protein. Moreover, immunohistochemical studies with this antibody indicate that Tau oligomerization precedes the formation of mature NFT inclusions. Collectively, these findings demonstrate that the Tau dimers, including their pathogenic conformations, and higher order oligomers form during the earliest stages of AD pathogenesis and may represent a prefibrillar toxic form of aggregated Tau.

The examples that follow show that dimerization is an early event in the Tau aggregation process, which precedes the formation of filaments. In fact, in the examples, aggregation of purified Tau dimers resulted in the formation of oligomers and a few short filaments in contrast to the aggregation of monomeric Tau, which formed longer filaments. Stable filaments can form by a nucleation-elongation reaction in which monomers first form a stable nucleus (nucleation) to which additional monomers can add (elongation) (SO). The nucleation process is critical and rate-limiting, as lowering this energy barrier induces the production of more filaments. Because Tau dimers did not self-associate in the absence of inducer, these findings suggest that Tau dimer formation precedes nucleation and that some other conformational shift must occur prior to oligomer and filament formation. A potential caveat is that the cross-linked Tau dimers were denatured during the purification process, and, thus, it is possible that the proteins did not re-nature completely or correctly. Moreover, the results indicate that dimeric Tau is not favored for elongation, at least not in the cross-linked form. It is possible that dimers that are not cross-linked have the freedom to rearrange into a conformation such that elongation could occur. Further studies are required to elucidate the events necessary for Tau nucleation, and to determine whether dimers lead directly to oligomers and subsequent filament formation or whether these oligomers represent off-pathway aggregates that do not form filaments. In either event, the reduction and/or of these dimers may be useful because it may (i) directly stop or slow down microtubule dissociation, stop or reduce altered signaling, stop or reduce mitochondrial dysfunction, resulting in the prevention or reduction of neurodegeneration; or (ii) may prevent or reduce the number of NFTs, resulting in the prevention or reduction of neurodegeneration.

The relevance of these findings to AD was validated in the examples below, by the generation of a novel monoclonal antibody (i.e., TOC1) that selectively labels pathological Tau dimers and higher order oligomers. Interestingly, TOC1 immunoreactivity was greatly elevated in AD brains (Braak V-VI) over controls (Braak I-III). TOC1 avidly labeled the hallmark Tau pathology in AD including neuropil threads, neuritic plaques, and neuronal inclusions. This confirms, e.g., that TOC1 may be used as a diagnostic agent to diagnose and monitor progression of AD.

Moreover, the presence of TOC1 immunoreactive inclusions in control cases (Braak stages I and II) suggests that dimer/oligomer formation is an early event in disease pathogenesis. Supporting this assertion, immunofluorescence in human tissue sections indicated that oligomerization closely associates with Ser 422 phosphorylation, an early pathological event in AD (58). Moreover, colocalization with TR, a marker for fibrillar forms of both Tau and Aβ, and colocalization with MN423, a late NFT marker (60), was scarcely observed. These findings confirm that TOC1 does indeed label prefibrillar pathology. The presence of TOC1 positive prefibrillar inclusions in AD supports the in vitro Tau aggregation and cross-linking results of the examples, suggesting that Tau dimers/oligomers may be intermediates in the aggregation process that precedes NFT formation in situ. Thus; SDS-stable Tau oligomers (e.g., SDS-stabilized dimers of Tau) of the examples are believed to be intermediates in at least some form of Tau aggregation.

This relationship between the Tau dimers and higher order oligomers and Tau protein aggregation and the emergence of Alzheimer's disease symptoms, supports the conclusion that antibodies that selectively recognize the pathogenic Tau dimers and higher order oligomers may and do have clinical utility in Alzheimer's disease and related disorders.

Tau Monomers

NFTs, a pathological hallmark of AD, are composed of Tau aggregates in the form of paired helical filaments and straight filaments (62, 63). Tau aggregates are composed of pathological tau. Additionally, Tau appears to be necessary for (contribute to) Aβ-induced neurotoxicity in cell culture and transgenic mouse models (3-5). Tau inclusions are also found in other tauopathies that lack Aβ pathology, including Pick's disease, corticobasal degeneration, and progressive supranuclear palsy (6). Notably, mutations in the tau gene cause some forms of frontotemporal dementia (7-10), signifying that Tau dysfunction is sufficient to cause neurodegeneration.

Tau is a microtubule associated protein. There are currently six known isoforms of human tau protein. The amino acid sequences corresponding to the isoforms of the human tau protein of the present invention are given in SEQ ID NOs: 1-6.

SEQ ID NO: 1, the longest tau isoform, htau40, contains two N-terminal inserts and four microtubule binding (2N4R) domains, is as follows:

```
MAEPRQEFEV MEDHAGTYGL GDRKDQGGYT MHQDQEGDTD AGLKESPLQT PTEDGSEEPG      60

SETSDAKSTP TAEDVTAPLV DEGAPGKQAA AQPHTEIPEG TTAEEAGIGD TPSLEDEAAG     120

HVTQARMVSK SKDGTGSDDK KAKGADGKTK IATPRGAAPP GQKGQANATR IPAKTPPAPK     180

TPPSSGEPPK SGDRSGYSSP GSPGTPGSRS RTPSLPTPPT REPKKVAVVR TPPKSPSSAK     240

SRLQTAPVPM PDLKNVKSKI GSTENLKHQP GGGKVQIINK KLDLSNVQSK CGSKDNIKHV     300

PGGGSVQIVY KPVDLSKVTS KCGSLGNIHH KPGGGQVEVK SEKLDFKDRV QSKIGSLDNI     360

THVPGGGNKK IETHKLTFRE NAKAKTDHGA EIVYKSPVVS GDTSPRHLSN VSSTGSIDMV     420

DSPQLATLAD EVSASLAKQG L                                              441
```

SEQ ID NO: 2 contains two N-terminal inserts and three microtubule-binding domains (2N3R) as follows:

```
MAEPRQEFEV MEDHAGTYGL GDRKDQGGYT MHQDQEGDTD AGLKESPLQT PTEDGSEEPG      60

SETSDAKSTP TAEDVTAPLV DEGAPGKQAA AQPHTEIPEG TTAEEAGIGD TPSLEDEAAG     120

HVTQARMVSK SLDGTGSDDK KAKGADGKTK IATPRGAAPP GQKGQANATR IPAKTPPAPK     180

TPPSSGEPPK SGDRSGYSSP GSPGTPGSRS RTPSLPTPPT REPKKVAVVR TPPKSPSSAK     240

SRLQTAPVPM PDLKNVKSKI GSTENLKHQP GGGKVQIVYK PVDLSKVTSK CGSLGNIHHK     300

PGGGQVEVKS EKLDFKDRVQ SKIGSLDNIT HVPGGGNKKI ETHKLTFREN AKAKTDHGAE     360

IVYKSPVVSG DTSPAHLSNV SSTGSIDMVD SPQLATLADE VSASLAKQGL               410
```

SEQ ID NO:3 contains one N-terminal insert and four microtubule-binding domains (1N4R) as follows:

```
MAEPRQEFEV MEDHAGTYGL GDRKDQGGYT MHQDQEGDTD AGLKESPLQT PTGDGSEEPG      60

SETSDAKSTP TAEAEEAGIG DTPSLEDEAA GHVTQARMVS KSLDGTGSDD KKAKGADGKT     120

LIATPRGAAP PGQKGQANAT RIPAKTPPAP KTPPSSGEPP KSGDRSGYSS PGSPGTPGSR     180

SRTPSLPTPP TREPKKVAVV RTPPKSPSSA KSRLQTAPVP MPDLKNVKSK IGSTENLKHQ     240

PGGGKVQIIN KKLDLSNVQS KCGSLDNILH VPGGSVQIV YKPVDLSKVT SKCGSLGNIH     300

HKPGGGQVEV KSEKLDFKDR VQSKIGSLDN ITHVPGGGNK KIETHKLTFR ENAKAKTDHG     360

AEIVYKSPVV SGDTSPRHLS NVSSTGSIDM VDSPQLATLA DEVSASLAKQ GL            412
```

SEQ ID NO: 4 contains zero N-terminal inserts and four microtubule-binding domains (0N4R) as follows:

```
MAEPRQEFEV MEDHAGTYGL GDRLDQGGYT MHQDQEGDTD AGLKAEEAGI GDTPSLEDEA      60

AGHVTQARMV SKSKDGTGSD DKKAKGADGK TKIATPRGAA PPGQKGQANA TRIPAKTPPA     120

PKTPPSSGEP PKSGDRSGYS SPGSPGTPGS RSRTPSLPTP PTREPKKVAV VATPPKSPSS     180

AKSRLQTAPV PMPDLKNVKS LIGSTENLKH QPGGGKVQII NKKLDLSNVQ SKCGSKDNIK     240

HVPGGGSVQI VYKPVDLSKV TSKCGSLGNI HHKPGGGQVE VKSEKLDFKD RVQSKIGSLD     300

NITHVPGGGN KKIETHKLTF RENAKALTDH GAEIVYKSPV VSGDTSPRHL SNVSSTGSID     360

MVDSPQLATL ADEVSASLAK QGL                                            383
```

SEQ ID NO: 5 contains one N-terminal insert and three microtubule-binding domains (1N3R) as follows:

```
MAEPRQEFEV MEDHAGTYGL GDRKDQGGYT MHQDQEGDTD AGLKESPLQT PTEDGSEEPG      60

SETSDAKSTP TAEAEEAGIG DTPSLEDEAA GHVTQARMVS KSKDGTGSDD KKAKGADGKT     120

KIATPRGAAP PGQKGQANAT RIPAKTPPAP KTPPSSGEPP KSGDRSGYSS PGSPGTPGSR     180

SRTPSLPTPP TREPKKVAVV RTPPKSPSSA KSRLQTAPVP MPDLKNVKSK IGSTENLKHQ     240

PGGGKVQIVY KPVDLSKVTS KCGSLGNIHH KPGGGQVEVK SEKLDFKDRV QSKIGSLDNI     300

THVPGGGNKK IETHKLTFRE NAKAKTDHGA EIVYKSPVVS GDTSPRHLSN VSSTGSIDMV     360

DSPQLATLAD EVSASLAKQG L                                              381
```

SEQ ID NO: 6 contains zero N-terminal inserts and three microtubule-binding domains (0N3R) as follows:

```
MAEPRQEFEV MEDHAGTYGL GDRKDQGGYT MHQDQEGDTD AGLKAEEAGI GDTPSLEDEA      60

AGHVTQARMV SKSKDGTGSD DKKAKGADGK TKIATPRGAA PPGQKGQANA TRIPAKTPPA     120

PKTPPSSGEP PKSGDRSGYS SPGSPGTPGS RSRTPSLPTP PTREPKKVAV VRTPPKSPSS     180

AKSRLQTAPV PMPDLKNVKS KIGSTENLKH QPGGGKVQIV YKPVDLSKVT SKCGSLGNIH     240

HKPGGGQVEV KSEKLDFKDR VQSKIGSLDN ITHVPGGGNK KIGTHKLTFR ENAKAKTDHG     300

AEIVYKSPVV SGDTSPRHLS NVSSTGSIDM VDSPQLATLA DEVSASLAKQ GL             352
```

Under physiological conditions, Tau is a highly soluble microtubule-associated protein with limited secondary structure (11). In AD and other tauopathies, Tau becomes hyperphosphorylated and undergoes conformational shifts that lead to its self-association into filamentous and non-filamentous aggregates (12). Filamentous Tau is highly ordered, possessing β-pleated structure, as is typical of amyloidogenic proteins (13). Although NFT load correlates with neuronal cell loss and the severity of cognitive impairment in AD, whether or not these filamentous Tau aggregates are neurotoxic remained controversial. Overexpression of both wild type and mutant Tau induces neurodegeneration in various animal models (14-19); however, memory deficits and cell loss precede detectable NFT-like Tau pathology (20, 21). Moreover, suppression of Tau expression improves memory function and halts further cell loss. Yet NFTs persist, suggesting that neurofibrillary pathology is not sufficient for neurodegeneration (22, 23). Importantly, neurodegeneration occurs in some animal models overexpressing Tau despite the absence of overt neurofibrillary pathology (19, 24). Thus, NFTs may not be required for and may not be the primary cause of neurotoxicity and cognitive dysfunction. In fact, levels of early Tau multimeric aggregates that preceded NFTs correlated with memory deficits in transgenic mice that overexpress Tau (25). Collectively, these studies strongly suggest that an intermediate Tau aggregate preceding NFT formation may be responsible for neuronal dysfunction observed in AD and other tauopathies.

Based on the examples below, the intermediate Tau aggregate preceding NFT formation appears to be a specific Tau multimer (i.e., a tau dimer) which will be described below.

Tau Multimers

Certain Tau multimers (e.g. dimers, trimers, etc.) are described elsewhere; however, previous work primarily focused on intermolecular associations mediated by disulfide bonds (29, 31, 69). Although three-repeat Tau possesses a single cysteine residue, four-repeat Tau has two cysteine residues favoring intramolecular over intermolecular disulfide bonds (30, 31). Furthermore, multiple reports affirm that reduction-resistant Tau multimers are present in AD and frontotemporal dementia (25, 70).

Although the existence of certain Tau multimeric aggregates in AD brain homogenates has been reported (25, 29, 56), the composition of these aggregates remained controversial. Previous studies suggest that Tau dimers are created when inducers such as heparin (29, 31) or thioflavin S (26) are used, and even in the absence of inducers (29, 71, 72), whereas others suggest Tau oligomers are composed of trimeric subunits (28). However, all of these previous conclusions were based on molecular weight estimations with SDS-PAGE, gel filtration chromatography, and/or mathematical modeling. Because Tau binds anomalously to SDS and exists as a non-globular protein, mass estimation using these techniques can be inaccurate (73).

The invention is one aspect identifies a cross-linked apparent 180-kDa multimer of Tau as a dimer, utilizing SELDI-TOF mass spectrometry to analyze the cross-linked apparent 180-kDa multimer, and to provide a more definitive measurement of the molecular mass of this aggregate. Data in the examples that follow clearly demonstrate that this aggregate is in fact a dimer. For example, the data shows that, SDS-stable Tau oligomers (e.g., SDS-stabilized dimers of Tau) are disease specific, because 180 KDa oligomeric species are found in the brain homogenates of patients with advance stages of AD, but not in the brain homogenates of patients without cognitive impairment during early states of AD (e.g., Braak stage I).

The examples that follow also demonstrate that dimeric aggregates occur in the absence of cross-linker and even, to some extent, in the absence of inducer; and that B4M cross-linking stabilizes these aggregates. This finding allows, inter alia, for the preparation of a stabilized tau dimer capable of being used as an immunogen for the production of antibodies selective for the precursors of pathological tau.

An isolated dimer of the invention may comprise two tau proteins cross-linked to each other having the same conformation as two hTau40 cross-linked to each other through B4M at one or more cysteine residues. In the preferred embodiments, at least one of the cross-links between the individual tau monomers is not a disulfide bridge between cysteines of the tau monomers. One or two of the tau proteins may be hTau40. One or two of the tau proteins may also be a truncated tau (e.g., ΔTau, hTau40 truncated at $Asp^{421}$). Generally, however, both Tau proteins are hTau40.

In an additional aspect, the invention is directed to an isolated non-filamentous tau oligomer comprising at least three tau monomers.

Immunogenic Peptide

An isolated immunogenic peptide ("immunogen") of the present invention, comprises at least two tau proteins cross-linked to each other, either directly or through a linker at one or more cysteine residues. The immunogenic peptide is preferably a non-naturally occurring (i.e., genetically engineered) peptide or protein. The cross-linking preferably induces a pathogenic conformation and allows for the stabilization of Tau in its aggregation-competent state. The immunogenic peptide is capable of inducing a production of the antibodies capable of selectively recognizing pathogenic tau dimers and prefibrillar pathological or neurotoxic tau oligomers described above, including their pathogenic conformations in a mammal, upon administration to the mammal. The immunogenic peptide may and is generally made by artificial means.

The linker may be an agent which has a sulfhydryl (SH) group and is capable of reacting with available cites upon UV illumination. The linker may, e.g., be selected from the group consisting of B4M, PEAS (N-((2-pyridyldithio)ethyl)-4-azidosalicylamide), succinimidyl trans-4-(maleimidylmethyl) cyclohexane-1-carboxylate (SMCC), 3-(2-pyridyldithio)propionate (SPDP), 2,5-Pyrrolidinedione, 1-[1-oxo-3-(2-pyridinyldithio)propoxy], succinimidyl acetylthioacetate (SATA), N-((2-pyridyldithio)ethyl)-4-azidosalicylamide), or the like.

In the preferred embodiments, the linker is B4M (1H-Pyrrole-2,5-dione, 1-(4-benzoylphenyl). B4M is a heterobifunctional, photoreactive crossslinker which is capable of chemically reacting and selectively labeling sulfhydryl group(s) (SH) of the cysteines of Tau (e.g., hTau40). The chemical formula of B4M is $C_{17}H_{11}NO_3$; and the structural formula of B4M is:

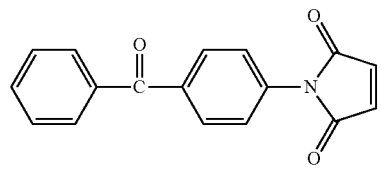 [SMILES: O=C(c1ccccc1)c1ccc(N2C(=O)C=CC2=O)cc1]

In the preferred embodiments, the linker is B4M and at least one of the cross-links between the individual tau monomers is not a disulfide bridge between cysteines of the monomers. In certain embodiments, one of the tau monomers may be a truncated Tau (e.g., ΔTau, hTau40 truncated at $Asp^{421}$). In other embodiments, the immunogenic peptide may comprise at least two truncated tau cross-linked to each other, either directly or through a linker (e.g., B4M) at one or more cysteine residues. Thus, the immunogen may comprise two hTau40 cross-linked to each other, directly or through a linker (e.g., B4M), at one or more cysteine residues. The immunogen may also comprise hTau40 cross-linked to ΔTau, directly or through a linker (e.g., B4M), at one or more cysteine residues; or two ΔTau cross-linked to each other, directly or through a linker (e.g., B4M), at one or more cysteine residues. In all of these embodiments, at least one of the cross-links between the individual tau monomers is, preferably, not a disulfide bridge between cysteines of the tau monomers. However, in certain embodiments, all of the cross-links between the individual tau monomers are disulfide bridges between cysteines of the tau monomers.

When the tau protein is hTau40 or ΔTau, the tau protein may be cross-linked at $Cys^{291}$ and/or $Cys^{322}$. When the tau protein is 2N3R (SEQ ID NO: 2), the tau protein may be cross-linked at $Cys^{291}$. When the tau protein is 1N4R (SEQ ID NO: 3), the tau protein may be cross-linked at $Cys^{262}$ and/or $Cys^{293}$. When the tau protein is 0N4R (SEQ ID NO: 4), the tau protein may be cross-linked at $Cys^{233}$ and/or $Cys^{274}$. When the tau protein is 1N3R (SEQ ID NO: 5), the tau protein may be cross-linked at $Cys^{272}$. When the tau protein is 0N3R (SEQ ID NO: 6), the tau protein may be cross-linked at $Cys^{233}$.

The immunogenic peptide of the invention may comprise or consist of an epitope of the antibodies capable of selectively recognizing pathogenic tau dimers and prefibrillar pathological or neurotoxic oligomeric tau, including their pathogenic conformations, wherein the prefibrillar pathological or neurotoxic oligomeric tau comprises at least two tau proteins cross-linked to each other, directly or through a linker (e.g., B4M or N-((2-pyridyldithio)ethyl)-4-azidosalicylamide), at one or more cysteine residues.

For example, the immunogenic peptide of the invention may comprise or consist an epitope of an antibody having the variable region of the heavy chain of the antibody (V$_H$) of SEQ ID NO: 7, or a segment thereof:

QVQLQQPGAELVMPGASVKLSCKASGYTFTSYWMHWVKQRPGQGLEWIGEI

DPSDSYTNYNQKFKGKSTLTVDKPSSTAYMQLSSLTSEDSAVYYCARSGDG

SSPWYFDVWGTGTTVTVSS;

and
the variable region of the light chain of the antibody (V$_L$) of SEQ ID NO: 8, or a segment thereof:

DIVMTQSTLSLPVSLGDQASISCRSSQSIVHSNGNTYLEWYLQKPGQSPKL

LIYKVSNRFSGVPDRFSGSGSGTDFTLKISRVEAEDLGVYYCFQGSHVPRT

FGGGTKLEIK.

The immunogenic peptide of the invention may comprise an epitope of an antibody which selectively recognizes a pathogenic tau. The pathogenic tau in this embodiments includes, e.g., truncated tau, dimers of tau, trimmers of tau, prefibrillar oligomers of tau, and/or their pathogenic conformation. The antibody which selectively recognizes the pathogenic tau may be any one of the antibodies described below.

In certain embodiments, the immunogenic peptide of the invention may comprise or consist of an epitope of an antibody having the heavy chain of SEQ ID NO: 12, or a segment thereof; and the light chain of the antibody of SEQ ID NO: 14, or a segment thereof.

The immunogenic peptide of the invention may comprise or consist of an epitope of the antibody whose epitope comprises or consists of a fragment comprising or consisting of amino acid residues 221-228 of hTau40, or a portion thereof. In some of these embodiments, the epitope comprises or consists of a four, five, six, or seven amino acid segment from amino acid residues 221-228 of hTau40.

The immunogenic peptide may comprise a fragment consisting of amino acid residues 221-228 of hTau40, or a portion thereof.

Generally, at least two tau proteins, or segments thereof, may be required to form the epitope of the antibodies of the present invention. For example, the epitope of the antibodies may be formed by a conformation created by two hTau40 cross-linked to each other, directly or through a linker (e.g., B4M), at one or more cysteine residues. The epitope of the antibodies may also be formed by a conformation created by Tau40 cross-linked to ΔTau, directly or through a linker (e.g., B4M), at one or more cysteine residues. The epitope of the antibody may additionally be formed by conformation created by two ΔTau cross-linked to each other, directly or through a linker (e.g., B4M), at one or more cysteine residues. In all of these embodiments, at least one of the cross-links between the individual tau monomers is, preferably, not a disulfide bridge between cysteines of the monomers.

The epitope of the immunogenic peptide may be a discontinues epitope which comprises or consists of two different regions of tau (e.g., hTau40): (a) a first region comprising or consisting of a proline-rich region of Tau (i.e., residues 155-244 of hTau40), or a segment(s) thereof, and (b) a second region comprising or consisting of a segment(s) from the carboxy terminal region of tau (e.g., residues 376-441 or residues 376-421 of hTau40). The first region may consist of a peptide consisting of a segment(s) from the proline region of Tau (i.e., residues 155-244 of hTau40) consisting from 4 to 80 residues, from 5 to 70 residues, from 5 to 60 residues, from 5 to 50, from 5 to 40 residues, from 5 to 35 residues, 5 to 30 residues, from 5 to 25 residues, from 5 to 20 residues, from 5 to 15 residues, from 5 to 12 residues, from 5 to 10 residues, from 5 to 9 residues of the proline-rich region of hTau40, and the second region may consist of a peptide consisting of a segment(s) from the carboxy terminal region of Tau (residues 376-441 or residues 376-421 of hTau40) consisting of from 5 to 60 residues, from 5 to 50, from 5 to 40 residues, from 5 to 35 residues, 5 to 30 residues, from 5 to 25 residues, from 5 to 20 residues, from 5 to 15 residues, from 5 to 12 residues, from 5 to 10 residues, from 5 to 9 residues from the carboxy terminal region of Tau (e.g., hTau40).

In some of these embodiments, the fragment from the proline region of hTau40 consists of residues 155-244, residues 160-240, residues 170-235, residues 180-230, residues 190-230, residues 195-230, residues 200-230, residues 205-230, residues 210-230, residues 212-230, residues 215-229, residues 218-229, residues 219-229, residues 220-229, residues 221-228, a segment(s) of any of the foregoing, or a combination of any of the foregoing of hTau40; and the fragment from the carboxy terminal region of hTau40 consists of residues 376-441, residues 376-421, residues 380-421, residues 390-421, residues 400-421, residues 410-421, residues 412-421, residues 415-421, residues 416-421, a segment(s) of any of the foregoing, or a combination of any of the foregoing of hTau40. Thus, the fragment from the proline region of hTau40 may consist, e.g., residues 221-228, or a segment thereof, of hTau40, and the fragment from the carboxy terminal region of hTau40 may consist from residues 400-421, or a segment thereof, of hTau40.

In some preferred embodiments, the fragment from the proline-rich region of hTau40 consists of residues 221-228 of hTau40, and the fragment from the carboxy terminal region of hTau40 consists of residues 376-441, residues 376-421, residues 380-421, residues 390-421, residues 400-421, residues 410-421, residues 412-421, residues 415-421, residues 416-421, a segment(s) of any of the foregoing, or a combination of any of the foregoing of hTau40.

The epitope of the immunogenic peptide may also include a fragment of hTau40 consisting of Cys$^{291}$-Arg$^{349}$, or a segment thereof.

Formation of the epitopes mentioned in the preceding paragraphs, generally, precedes β-sheet formation characteristic of NFTs.

In certain embodiments, the immunogenic peptide comprises a mimotope of an epitope of an antibody which selectively recognizes a pathogenic tau. The pathogenic tau in this embodiments includes, e.g., truncated tau, dimers of tau, trimmers of tau, prefibrillar oligomers of tau, and/or their pathogenic conformation. The antibody which selectively recognizes the pathogenic tau may be any one of the antibodies described below in the Antibody section.

In certain embodiments, the immunogenic peptide of the invention comprises a chimeric peptide comprising (i) a residues 221-228, or a subfragment thereof, of hTau40 fused together with or without a spacer (e.g., an amino acid spacer) to (ii) a promiscuous T helper cell epitope derived from a different source than the fragment (e.g., from tetanus toxoid). The promiscuous T helper cell epitope is, generally, a T cell epitope from tetanus toxin, pertussis toxin, diphtheria toxin, measles virus F protein, hepatitis B virus surface antigen, *Chlamydia trachomitis* major outer membrane protein, *Plasmodium falciparum* circumsporozoite, *Schistosoma mansoni* triose phosphate isomerase, or *Escherichia coli* TraT. In certain embodiments, the promiscuous T helper cell epitope is a known strong T cell epitope is the tetanus toxoid promiscuous epitope of SEQ ID NO: 15.

In certain embodiments, the T helper cell epitopes in the chimeric peptide of the present invention are selected not only for a capacity to cause immune responses in most members of a given population, but also for a capacity to cause memory/recall responses. When the mammal is human, the vast majority of human subjects/patients receiving immunotherapy with the chimeric peptide of the present invention will already have been immunized with the pediatric vaccines (i.e., MMR and diphtheria+pertussis+tetanus vaccines) and, possibly, the hepatitis B virus vaccine. These patients have therefore been previously exposed to at least one of the $T_h$ epitopes present in chimeric pediatric vaccines. Prior exposure to a $T_h$ epitope through immunization with the standard vaccines should establish $T_h$ cell clones which can immediately proliferate upon administration of the chimeric peptide (i.e., a recall response), thereby stimulating rapid B cell responses to the chimeric peptide. In addition, the $T_h$ epitopes avoid any pathogen-specific B cell and/or suppressor T cell epitopes which could lead to carrier-induced immune suppression, a problem encountered when toxin molecules are used to elicit T helper cell responses.

The $T_h$ epitopes in the chimeric peptide of the invention are promiscuous but not universal. This characteristic means that the $T_h$ epitopes are reactive in a large segment of an outbred population expressing different MHC antigens (reactive in 50 to 90% of the population), but not in all members of that population. To provide a comprehensive, approaching universal, immune reactivity for an internal peptide cleavage product, a combination of chimeric peptides with different $T_h$ epitopes can be prepared. For example, a combination of four chimeric peptides with promiscuous $T_h$ epitopes from tetanus and pertussis toxins, measles virus F protein and HBsAg may be more effective.

Promiscuous $T_h$ epitopes often share common structural features. For example, promiscuous $T_h$ epitopes range in size from about 15 to about 30 residues. Amphipathic helices are a common feature of the $T_h$ epitopes. An amphipathic helix is defined by an α-helical structure with hydrophobic amino acid residues dominating the surrounding faces. $T_h$ epitopes frequently contain additional primary amino acid patterns such as a Gly or a charged reside followed by two to three hydrophobic residues followed in turn by a charged or polar residue. This pattern defines Rothbard sequences. $T_h$ epitopes often obey the 1, 4, 5, 8 rule, where a positively charged residue is followed by hydrophobic residues at the fourth, fifth and eighth positions after the charged residue. Since all of these structures are composed of common hydrophobic, charged and polar amino acids, each structure can exist simultaneously within a single $T_h$ epitope.

$T_h$ is therefore a sequence of amino acids (natural or non-natural) that contain a $T_h$ epitope. The $T_h$ epitope can be a continuous or discontinuous epitope. Hence, not every amino acid of $T_h$ is necessarily part of the epitope. Accordingly, $T_h$ epitopes, including analogs and segments of $T_h$ epitopes, are capable of enhancing or stimulating an immune response to the internal peptide cleavage product. Immunodominant $T_h$ epitopes are broadly reactive in animal and human populations with widely divergent MHC types (Celis et al., 1988; Demotz et al., 1989; and Chong et al., 1992). The $T_h$ domain of the chimeric peptides of the present invention has from about 10 to about 50 amino acids residues and preferably from about 10 to about 30 amino acids residues. When multiple $T_h$ epitopes are present, then each $T_h$ epitope is independently the same or different.

$T_h$ epitope analogs include substitutions, deletions and insertions of one to about five amino acid residues in the $T_h$ epitope. $T_h$ segments are contiguous portions of a $T_h$ epitope that are sufficient to enhance or stimulate an immune response to the internal peptide cleavage product. An example of $T_h$ segments is a series of overlapping peptides that are derived from a single longer peptide.

The $T_h$ epitopes of the present invention include, e.g., hepatitis B surface antigen T helper cell epitopes ($HB_s$ $T_h$); pertussis toxin T helper cell epitopes (PT $T_h$); tetanus toxin T helper cell epitopes (TT $T_h$); measles virus F protein T helper cell epitope ($MV_{F1}$ $T_h$); Chlamydia trachomitis major outer membrane protein T helper cell epitopes (CT $T_h$); diphtheria toxin T helper cell epitopes (DT TO; Plasmodium falciparum circumsporozoite T helper cell epitopes (PF $T_h$); Schistosoma mansoni triose phosphate isomerase T helper cell epitopes (SM $T_h$); Escherichia coli TraT T helper cell epitopes (TraT $T_h$), and immune-enhancing analogs or any of the foregoing. The epitopes of these T helper cells are as provided in Table 1:

TABLE 1

| T helper cell | Epitope |
| --- | --- |
| $TT_O$ $T_H$ | SEQ ID NO: 16 |
| $HB_3$ $T_H$ | SEQ ID NO: 17 |
| $TT_1$ $T_H$ | SEQ ID NO: 18 |
| $TT_1$ $T_H$ | SEQ ID NO: 19 |
| $TT_2$ $T_H$ | SEQ ID NO: 20 |
| $PT_{1A}$ $T_H$ | SEQ ID NO: 21 |
| $TT_3$ $T_H$ | SEQ ID NO: 22 |
| $PT_2$ $T_H$ | SEQ ID NO: 23 |
| $MV_{F1}$ $T_H$ | SEQ ID NO: 24 |
| $MV_{F2}$ $T_H$ | SEQ ID NO: 25 |
| $TT_4$ $T_H$ | SEQ ID NO: 26 |
| $TT_5$ $T_H$ | SEQ ID NO: 27 |
| $CT_1$ $T_H$ | SEQ ID NO: 28 |
| $DT_1$ $T_H$ | SEQ ID NO: 29 |
| $DT_2$ $T_H$ | SEQ ID NO: 30 |
| PF $T_H$ | SEQ ID NO: 31 |
| SM $T_H$ | SEQ ID NO: 32 |
| TraT1 $T_H$ | SEQ ID NO: 33 |
| TraT2 $T_H$ | SEQ ID NO: 34 |
| TraT3 $T_H$ | SEQ ID NO: 35 |

In certain embodiments, the immunogenic peptide of the invention comprises a chimeric peptide comprising a four, five, six, or seven amino acid fragment from amino acid residues 221-228 of hTau40, the fragment fused, with or without a spacer (e.g., an amino acid(s) spacer), to (ii) the tetanus toxoid promiscuous epitope of SEQ ID NO: 15.

In certain embodiments, the immunogenic peptide of the invention comprises a chimeric peptide comprising an isolated epitope of an antibody having the heavy chain of SEQ ID NO: 12, or a segment thereof; and the light chain of the antibody of SEQ ID NO: 14, or a segment thereof, the isolated epitope fused, with or without a spacer, to (ii) the tetanus toxoid promiscuous epitope of SEQ ID NO: 15.

In certain embodiments, the immunogenic peptide of the invention comprises a chimeric peptide comprising an isolated epitope of an antibody having the heavy chain of SEQ ID NO: 12, or a segment thereof; and the light chain of the antibody of SEQ ID NO: 14, or a segment thereof, the isolated epitope fused, with or without a spacer, to a promiscuous T helper cell epitope of a sequence selected from the group consisting of SEQ ID NO: 16; SEQ ID NO: 17; SEQ ID NO: 18; SEQ ID NO: 19; SEQ ID NO: 20; SEQ ID NO: 21; SEQ ID NO: 22; SEQ ID NO. 23; SEQ ID NO: 24; SEQ ID NO: 25; SEQ ID NO: 26; SEQ ID NO: 27; SEQ ID NO: 28; SEQ ID NO: 29; SEQ ID NO: 30; SEQ ID NO: 31; SEQ ID NO: 32; SEQ ID NO: 33, SEQ ID NO: 34, and SEQ ID No: 35.

The immunogenic peptides of the invention are capable of inducting production of the antibodies which selectively recognize the conformation of pathogenic tau dimers and prefibrillar pathogenic tau oligomers, but do not substantially recognize NFTs and, preferably, do not substantially recognize Tau monomers.

Immunogens in accordance with the present invention can be prepared by dimerization of Tau (e.g., hTau40) by a technique comprising reacting tau monomers with a molar excess of a cross-linker, aggregating the monomers to form an aggregate, and exposing the aggregates to a shortwave UV light. This process does not rely upon oxidative conditions. The cross-linker may be an agent which has a sulfhydryl (SH) group and is capable of reacting with available cites upon UV illumination. The cross-linker may, e.g., be selected from the group consisting of B4M, PEAS (N-((2-pyridyldithio)ethyl)-4-azidosalicylamide), succinimidyl trans-4-(maleimidylmethyl)cyclohexane-1-carboxylate (SMCC), 3-(2-pyridyldithio)propionate (SPDP), 2,5-Pyrrolidinedione, 1-[1-oxo-3-(2-pyridinyldithio)propoxy], succinimidyl acetylthioacetate (SATA), N-((2-pyridyldithio)ethyl)-4-azidosalicylamide), or the like. In the preferred embodiments, the cross-linker is B4M, a 10-fold molar excess of B4M is used, the monomers are aggregated in the presence of arrachidonic acid, and are cross-linked with UV light (254 mm).

Immunogens may also be prepared by a method comprising reacting a tau monomer (e.g. hTau40) with benzophenone-4-maleimide (B4M). B4M preferably reacts with one or more cysteine residues of the tau monomer. The reaction is preferably conducted before the tau monomer is aggregated.

These technique has several advantages over techniques described elsewhere: (a) site-specific labeling of native cysteine residues, while Tau is in its soluble, extended conformation; (b) lack of interference with the Tau aggregation process; and (c) generation of stable, irreversible cross-linking of Tau multimers allowing for the determination and studying of the conformation of the Tau aggregates and downstream applications such as aggregation and/or toxicity studies.

A tau monomer for use in the dimerization (e.g., hTau40 or ΔTau) may be obtained from a commercial source or synthesized denovo by using a number of numerous well known synthetic recombinant techniques, including, e.g., techniques used to transform cells, construct vectors, extract messenger RNA, prepare cDNA libraries, and the like. Most of these techniques are widely practiced in the art, and most practitioners are familiar with the standard resource materials which describe specific conditions and procedures widely practiced in the art. For example, the tau monomer may be synthesized by solid phase peptide synthesis or recombinant expression, or can be obtained from natural sources.

Automatic peptide synthesizers are commercially available from numerous suppliers, such as Applied Biosystems (Foster City, Calif.).

Procedures for recombinant expression are described by Sambrook et al., Molecular Cloning: A Laboratory Manual (C.S.H.P. Press, NY 2d ed., 1989), which is hereby incorporated by reference in its entirety. Recombinant expression systems can include bacteria, such as *E. coli*, yeast, insect cells, or mammalian cells. The most commonly used prokaryote system for the production of recombinant proteins remains *E. coli*, however, other microbial strains may also be used, such as Bacilli, for example *Bacillus subtilis*, various species of *Pseudomonas*, or other bacterial strains. In such prokaryotic systems, plasmid vectors which contain replication sites and control sequences derived from a species compatible with the host are used. Commonly used prokaryotic control sequences include promoters for transcription initiation, optionally with an operator, along with ribosome binding site sequences.

A wide variety of eukaryotic hosts are also now available for production of recombinant foreign proteins. Commonly used eukaryotic systems include yeast, insect cells, mammalian cells, avian cells, and cells of higher plants. The list is not exhaustive. As in bacteria, eukaryotic hosts may be transformed with expression systems which produce the desired protein directly, but more commonly, signal sequences are provided to effect the secretion of the protein. Eukaryotic systems have the additional advantage that they are able to process introns which may occur in the genomic sequences encoding proteins of higher organisms. Eukaryotic systems also provide a variety of processing mechanisms which result in, for example, glycosylation, oxidation or derivatization of certain amino acid residues, conformational control, and so forth.

Suitable promoters are available which are compatible and operable for use in each of these host types as well are termination sequences and enhancers, as e.g., the baculovirus polyhedron promoter. As above, promoters can be either constitutive or inducible. For example, in mammalian system, the MTII promoter can be induced by the addition of heavy metal ions.

The particulars for the construction of expression systems suitable for desired host are known to those in the art. For recombinant production of the protein, the DNA encoding it is suitable ligated into the expression system of choice, and the system is then transformed into the compatible host cell which is then cultured and maintained under conditions wherein expression of the foreign gene takes place. The immunogens of this invention produced this way, are recovered from the culture, either by lysing the cells or from the culture medium as appropriate and known to those in the art.

Correct ligations for plasmid construction can be confirmed by first transforming a suitable host with the ligation mixture. Successful transformants are selected by ampicillin, tetracycline or other antibiotic resistance or using other markers depending on the mode of plasmid construction, as is understood in the art.

Tau monomers may also be produced by chemical synthesis of the amino acid sequence of a tau-protein (Goedert et al., 1988, Proc. Natl. Acad. Sci. USA, 85:4051-4055) or a fragment thereof, as predicted from the cloning and sequencing of a cDNA coding for a tau-protein. This tau-protein sequence information may be utilized to predict the appropriate amino and carboxy terminal tau-peptides to be chemically synthesized using standard peptide synthesis methods known in the art. These methods include, e.g., a solid-phase method devised by R. Bruce Merrifield, (Erickson and Merrifield, "Solid-Phase Peptide Synthesis", in The Proteins, Volume 2, H. Neurath & R. Hill (eds.) Academic Press, Inc., New York pp. 255-257; Merrifield, 1986, "Solid phase synthesis", Science, 242:341-347). In the solid-phase method, amino acids are added stepwise to a growing peptide chain that is linked to an insoluble matrix, such as polystyrene beads. A major advantage of this method is that the desired product at each stage is bound to beads that can be rapidly filtered and washed and thus the need to purify intermediates is obviated. All of the reactions are carried out in a single vessel, which eliminates losses due to repeated transfers of products.

The production of tau monomer, or a fragment thereof, can further be achieved by recombinant DNA technology. For example, appropriate tau nucleotide coding sequences may be synthesized, cloned and expressed in appropriate host cells. Since the DNA sequence encoding for a tau-protein is known (Goeddert et al., 1988, Proc. Natl. Acad. Sci., USA 85:4051-4055), DNA probes may be synthesized by standard methods known in the art to screen cDNA libraries prepared from brain tissue of Alzheimer's disease patients for the specific tau-protein cDNA's. These DNA probes can further be used to isolate the entire family of tau-protein genes from these cDNA libraries using methods which are well known to those skilled in the art. See, for example, the techniques described in Maniatis et al., 1982, Molecular Cloning A Laboratory Manual, Cold Spring Harbor Laboratory, N.Y., Chapter 7.

The polymerase chain reaction (PCR) technique can be utilized to amplify the individual members of the tau family for subsequent cloning and expression of tau-protein cDNAs (e.g., see U.S. Pat. Nos. 4,683,202; 4,683,195; 4,889,818; Gyllensten et al., 1988, Proc. Nat'l Acad. Sci. USA, 85:7652-7656; Ochman et al., 1988, Genetics, 120:621-623; Triglia et al., 1988, Nucl. Acids. Res., 16:8156; Frohman et al., 1988, Proc. Nat'l Acad. Sci. USA, 85:8998-9002; Loh et al., 1989, Science, 243:217-220).

Methods which are well known to those skilled in the art can be used to construct expression vectors containing tau-proteins or fragments thereof coding sequences and appropriate transcriptional/translational control signals. These methods include in vitro recombinant DNA techniques, synthetic techniques and in vivo recombination/genetic recombination. See, for example, the techniques described in Maniatis et al., 1982, Molecular Cloning A Laboratory Manual, Cold Spring Harbor Laboratory, N.Y., Chapter 12.

A variety of host-expression vector systems may be utilized to express tau-proteins or fragments thereof. These include but are not limited to microorganisms such as bacteria transformed with recombinant bacteriophage DNA, plasmid DNA or cosmid DNA expression vectors containing a coding sequence for a tau-protein or fragment thereof; yeast transformed with recombinant yeast expression vectors containing a coding sequence for a tau-protein or fragment thereof; insect cell systems infected with recombinant virus expression vectors (e.g., baculovirus) containing a coding sequence for a tau-protein or fragment thereof; or animal cell systems infected with recombinant virus expression vectors (e.g., adenovirus, vaccinia virus) containing a coding sequence for a tau-protein or fragment thereof.

The expression elements of these vectors vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage lambda, plac, ptrp, ptac (ptrp-lac hybrid promoter) and the like may be used; when cloning in insect cell systems, promoters such as the baculovirus polyhedrin promoter may be used; when cloning in mammalian cell systems, promoters such as the adenovirus late promoter or the vaccinia virus 7.5K promoter may be used. Promoters produced by recombinant DNA or synthetic techniques may also be used to provide for transcription of the inserted coding sequence for a tau-protein or fragment thereof.

In yeast, a number of vectors containing constitutive or inducible promoters may be used. For a review see, Current Protocols in Molecular Biology, Vol. 2, 1988, Ed. Ausubel et al., Greene Publish. Assoc. & Wiley Interscience Ch. 13; Grant et al., 1987, Expression and Secretion Vectors for Yeast, in Methods in Enzymology, Eds. Wu & Grossman, 1987, Acad. Press, N.Y., Vol. 153, pp. 516-544; Glover, 1986, DNA Cloning, Vol. II, IRL Press, Wash., D.C. Ch. 3; and Bitter, 1987, Heterologous Gene Expression in Yeast, Methods in Enzymology, Eds. Berger & Kimmel, Acad. Press, N.Y., Vol. 152, pp. 673-684; and The Molecular Biology of the Yeast *Saccharomyces,* 1982, Eds. Strathern et al., Cold Spring Harbor Press, Vols. I and II. For complementation assays in yeast, cDNAs for tau-proteins or fragments thereof may be cloned into yeast episomal plasmids (YEp) which replicate autonomously in yeast due to the presence of the yeast 2μ circle. The tau-protein or fragment thereof sequence may be cloned behind either a constitutive yeast promoter such as ADH or LEU2 or an inducible promoter such as GAL (Cloning in Yeast, Chpt. 3, R. Rothstein In; DNA Cloning Vol. 11, A Practical Approach, Ed. DM Glover, 1986, IRL Press, Wash., D.C.). Constructs may contain the 5' and 3' non-translated regions of a cognate tau-protein mRNA or those corresponding to a yeast gene. YEp plasmids transform at high efficiency and the plasmids are extremely stable. Alternatively, vectors may be used which promote integration of foreign DNA sequences into the yeast chromosome.

In certain embodiments, an insect system could be used to express tau-proteins or fragments thereof. In one such system, *Autographa californica* nuclear polyhedrosis virus (AcNPV) is used as a vector to express foreign genes. The virus grows in *Spodoptera frugiperda* cells. The tau-protein or fragment thereof coding sequence may be cloned into non-essential regions (for example the polyhedrin gene) of the virus and placed under control of an AcNPV promoter (for example the polyhedrin promoter). Successful insertion of the polyhedrin gene results in production of non-occluded recombinant virus (i.e., virus lacking the proteinaceous coat coded for by the polyhedrin gene). These recombinant viruses are then used to infect *Spodoptera frugiperda* cells in which the inserted gene is expressed. (e.g., see Smith et al., 1983, J. Biol., 46:586; Smith, U.S. Pat. No. 4,215,051).

An immunogen of the invention is immunoreactive whether it results from the expression of the entire gene sequence, a portion of the gene sequence or from two or more gene sequences which are ligated to direct the production of chimeric proteins. This reactivity may be demonstrated by standard immunological techniques, such as radioimmunoprecipitation, radioimmune competition, or immunoblots.

Immunogens of the invention are suitable to be administered intranasally, by a subcutaneous injection, intramuscular injection, IV infusion, transcutaneously, buccally, and for inclusion into pharmaceutical compositions for intranasal, subcutaneous, intramuscular injection, IV, transcutaneously, or buccal administration, as described in more detail below.

Upon administration to a mammal, the immunogens cause the mammal to produce antibodies which selectively recognize prefibrillar pathological or neurotoxic tau and precursors comprising comprise at least two tau proteins cross-linked to each other, directly or through a linker (e.g., B4M), at one or more cysteine residues.

Immunogens of the invention may also be used for testing or screening of drugs, for therapeutic monitoring and/or for the determination of the effectiveness of treatment of a tauopathy.

Antibodies

Isolated antibodies of the invention (e.g., non-naturally occurring antibodies or genetically engineered antibodies) are glycoproteins made up of light (L) and heavy (H) polypeptide chains, or segments of any of the foregoing. L and H chains are subdivided into variable and constant regions. The variable regions are responsible for antigen-binding. Preferably, the variable region of the heavy chain of the antibody ($V_H$) comprises or consists of SEQ ID NO: 7, or a segment(s) thereof:

QVQLQQPGAELVMPGASVKLSCKASGYTFTSYWMHWVKQRPGQGLEWIGEI

DPSDSYTNYNQKFKGKSTLTVDKPSSTAYMQLSSLTSEDSAVYYCARSGDG

SSPWYFDVWGTGTTVTVSS;

and
the variable region of the light chain of the antibody ($V_L$) comprises or consists of SEQ ID NO: 8, or a segment(s) thereof:

DIVMTQSTLSLPVSLGDQASISCRSSQSIVHSNGNTYLEWYLQKPGQSPKL

LIYKVSNRFSGVPDRFSGSGSGTDFTLKISRVEAEDLGVYYCFQGSHVPRT

FGGGTKLEIK.

The heavy chain of the antibody may comprise or consist of SEQ ID NO: 12, or a segment(s) thereof; and the light chain of the antibody may comprise or consist of SEQ ID NO: 14, or a segment(s) thereof.

Isolated antibodies of the invention are capable of and selectively recognize prefibrillar pathological or neurotoxic tau and precursors comprising at least two tau proteins, or fragments thereof, cross-linked to each other, directly or through a linker (e.g., B4M), at one or more cysteine residues.

When the tau protein is hTau40 or ΔTau, the tau protein may be cross-linked at $Cys^{291}$ and/or $Cys^{322}$. When the tau protein is 2N3R (SEQ ID NO: 2), the tau protein may be cross-linked at $Cys^{291}$. When the tau protein is 1N4R (SEQ ID NO: 3), the tau protein may be cross-linked at $Cys^{262}$ and/or $Cys^{293}$. When the tau protein is 0N4R (SEQ ID NO: 4), the tau protein may be cross-linked at $Cys^{233}$ and/or $Cys^{274}$. When the tau protein is 1N3R (SEQ ID NO: 5), the tau protein may be cross-linked at $Cys^{272}$. When the tau protein is 0N3R (SEQ ID NO: 6), the tau protein may be cross-linked at $Cys^{233}$.

The linker may be an agent which has a sulfhydryl (SH) group and is capable of reacting with available cites upon UV illumination. The linker may, e.g., be selected from the group consisting of B4M, PEAS (N-((2-pyridyldithio)ethyl)-4-azidosalicylamide), succinimidyl trans-4-(maleimidylmethyl) cyclohexane-1-carboxylate (SMCC), 3-(2-pyridyldithio)propionate (SPDP), 2,5-Pyrrolidinedione, 1-[1-oxo-3-(2-pyridinyldithio)propoxy], succinimidyl acetylthioacetate (SATA), N-((2-pyridyldithio)ethyl)-4-azidosalicylamide), or the like. In the preferred embodiments, the linker is B4M.

The antibodies of the invention may specifically recognize a pathogenic conformation of the prefibrillar pathological or neurotoxic tau and precursors. In the preferred embodiments, this conformation is the conformation induced by cross-linking tau monomers as described in the present specification.

In the preferred embodiments, the antibodies of the invention are selective for the epitope comprising a fragment comprising or consisting of amino acid residues 221-228, or a portion thereof, of hTau40.

At least two tau proteins, or segments thereof may be required to form an epitope of the antibodies of the present invention. For example, the epitope of the antibodies may be formed by a conformation created by two hTau40 cross-linked to each other, directly or through a linker (e.g., B4M), at one or more cysteine residues. The epitope of the antibodies may also be formed by a conformation created by Tau40 cross-linked to ΔTau, directly or through a linker (e.g., B4M), at one or more cysteine residues. The epitope of the antibody may additionally be formed by conformation created by two ΔTau cross-linked to each other, directly or through a linker (e.g., B4M), at one or more cysteine residues.

The epitope of the antibodies may be a discontinues epitope which comprises or consists of two different regions of tau (e.g., hTau40): (a) a first region comprising or consisting of a proline-rich region of Tau (i.e., residues 155-244 or 221-228 of hTau40), or a segment(s) thereof, and (b) a second region comprising or consisting of a segment(s) from the carboxy terminal region of tau (e.g., residues 376-441 or residues 376-421 of hTau40). The first region may consist of a peptide consisting of a fragment from the proline region of Tau (i.e., residues 155-244 of hTau40) consisting from 4 to 80 residues, from 5 to 70 residues, from 5 to 60 residues, from 5 to 50, from 5 to 40 residues, from 5 to 35 residues, 5 to 30 residues, from 5 to 25 residues, from 5 to 20 residues, from 5 to 15 residues, from 5 to 12 residues, from 5 to 10 residues, from 5 to 9 residues of the proline-rich region of hTau40, and the second region may consist of a peptide consisting of a segment(s) from the carboxy terminal region of Tau (residues 376-441 or residues 376-421 of hTau40) consisting of from 5 to 60 residues, from 5 to 50, from 5 to 40 residues, from 5 to 35 residues, 5 to 30 residues, from 5 to 25 residues, from 5 to 20 residues, from 5 to 15 residues, from 5 to 12 residues, from 5 to 10 residues, from 5 to 9 residues from the carboxy terminal region of Tau (e.g., hTau40).

In some of these embodiments, the fragment from the proline region of hTau40 consists of residues 155-244, residues 160-240, residues 170-235, residues 180-230, residues 190-230, residues 195-230, residues 200-230, residues 205-230, residues 210-230, residues 212-230, residues 215-229, residues 218-229, residues 219-229, residues 220-229, residues 221-228, a segment(s) of any of the foregoing, or a combination of any of the foregoing of hTau40; and the fragment from the carboxy terminal region of hTau40 consists of residues 376-441, residues 376-421, residues 380-421, residues 390-421, residues 400-421, residues 410-421, residues 412-421, residues 415-421, residues 416-421, a segment(s) of any of the foregoing, or a combination of any of the foregoing of hTau40. Thus, the fragment from the proline region of hTau40 may consist, e.g., residues 221-228, or a segment(s) thereof, of hTau40, and the fragment from the carboxy terminal region of hTau40 may consist from residues 400-421, or a segment(s) thereof, of hTau40.

In some preferred embodiments, the fragment from the proline region of hTau40 consists of residues 221-228, or a portion thereof, and the fragment from the carboxy terminal region of hTau40 consists of residues 376-441, residues 376-421, residues 380-421, residues 390-421, residues 400-421, residues 410-421, residues 412-421, residues 415-421, residues 416-421, a segment(s) of any of the foregoing, or a combination of any of the foregoing of hTau40.

In some of these embodiments the epitope of the antibody may comprise or consists of residues 221-228, or a portion thereof, of hTau40. In some of these embodiments, the epitope comprises or consists of a four, five, six, or seven amino acid segment from amino acid residues 221-228 of hTau40.

The epitope of the antibody or a portion thereof, may lie within ninety amino acids of a MTBR of hTau40, and does not include any of the MTBRs.

The epitope of an antibody of the present invention may be an intermolecular and/or intramolecular epitope.

Formation of the epitopes mentioned in the preceding paragraphs, generally, precedes β-sheet formation characteristic of NFTs.

The antibodies of the invention preferably do not react with monomeric tau, when tested at saturating levels of anti-body-immunogen binding, do not react with α-synuclein, and do not react with Aβ in the unaggregated, oligomeric or filamentous states.

In the preferred embodiments of the invention, the antibodies of the invention are selective for the conformation of pathogenic tau dimers and prefibrillar oligomers and do not recognize NFTs.

The antibodies of the invention, preferably, show no affinity to a construct consisting of $Gln^{244}$-$Glu^{372}$ of hTau40. This indicates, e.g., that the antibodies of the invention do not recognize the portion of Tau aggregates possessing β-pleated sheets in the absence of the rest of the Tau molecule; and that the antibodies of the invention are conformation specific antibodies.

Figure 7:
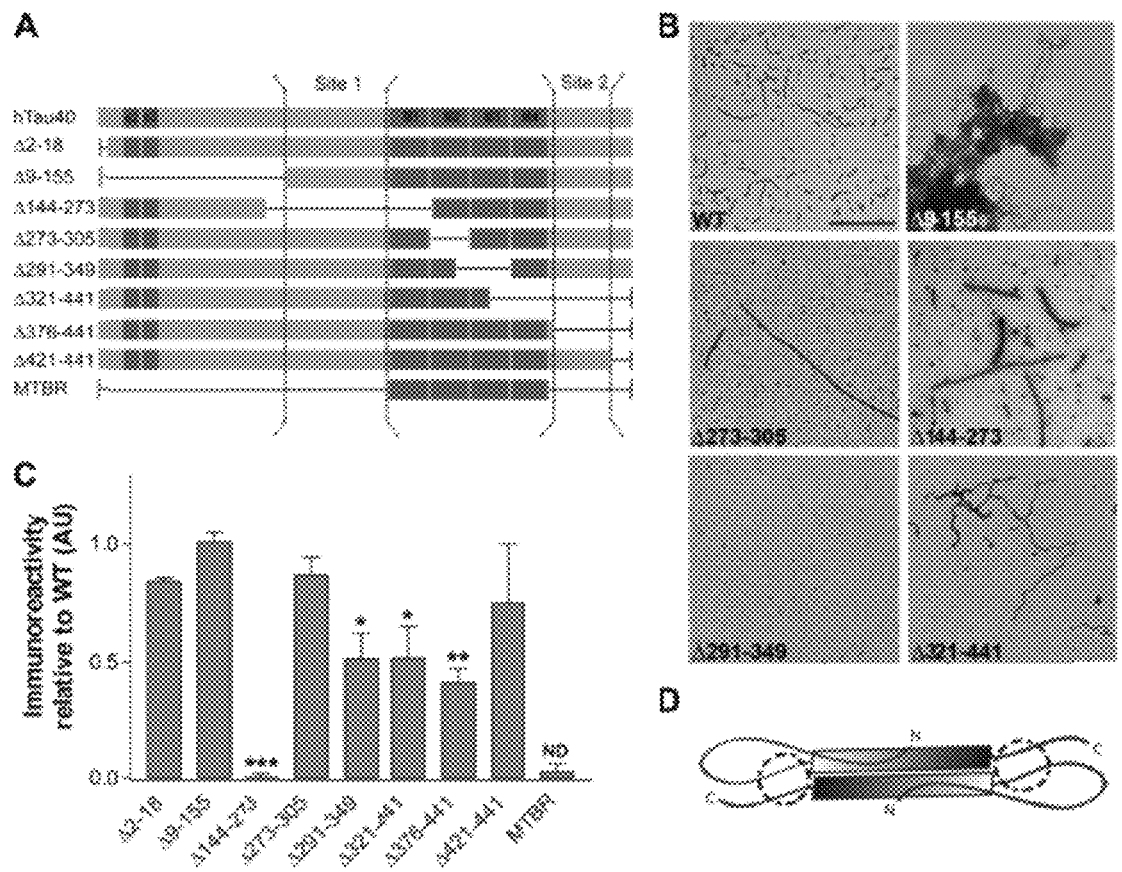
FIGS. 7A-7D depict epitope mapping of TOC1. Deletion mutants of hTau40 were assembled with AA, spotted onto nitrocellulose, and probed with TOC1.

The discontinuous epitopes of antibodies provide evidence for conformational changes in Tau during the disease process. For instance, epitope mapping of the Alz-50 antibody revealed that the N terminus comes into close proximity to the MTBR early in tangle evolution (35, 85). The epitopes of the antibodies is selectively recognized by TOC1, which will be described in detail below. It is possible that its epitope may occur from intramolecular folding events; however, because TOC1 does not recognize monomeric Tau at saturating levels of anti-body-immunogen binding, it is more likely that this is an intermolecular event consistent with the formation of dimers (e.g., anti-parallel dimers) given that the two epitopes are on either side of the MTBRs (see FIG. 7). This expands upon a previous study showing that three-repeat Tau can dimerize in an antiparallel manner (72). The results of the examples below suggest, e.g., that both three- and four-repeat Tau form dimers; however, TOC1 labeled only a portion of the Tau aggregates, suggesting that there may be other aggregation-competent conformations to discover. Future studies more precisely chart the evolution of the conformational shifts of Tau and how they relate to TOC1 during disease pathogenesis. Even so, the results below confer significant insights concerning the earliest stages of Tau aggregation and provide an important foundation for the future study of potentially neurotoxic Tau oligomers in disease pathogenesis, and for current development of the pharmaceutical compositions for use in the prevention and treatment of Tauopathies and/or diagnostic compositions for diagnosis and monitoring of Tauopathies.

In the preferred embodiments of the invention, the antibodies of the invention (i) inhibit, reduce, clear and/or eliminate formation of prefibrillar pathological tau aggregates, (ii) inhibit, reduce, clear and/or eliminate prefibrillar pathological aggregation of Tau, and/or (iii) prevent the formation of neurofiblary tangles and/or increase clearance of the neurofiblary tangles, all without affecting the biological functions of normal tau proteins. These antibodies do not affect the biological functions of normal tau proteins because these antibodies are selective for prefibrillar pathological or neurotoxic tau and precursors (i.e., they do not bind or do not sufficiently bind normal tau proteins to affect their biological function, e.g., when tested at saturating levels of antibody-immunogen binding).

The antibodies of the invention may neutralize and/or remove the dimers of Tau before these dimers are phosphorylated, and therefore may stop or prevent the cascade of the aggregation events early on.

The antibodies of the invention may directly block formation of tau filaments and slow down or stop formation of NFTs from tau filaments, e.g., by binding to and changing the conformation of tau dimers and prefibrillar oligomers to a conformation which is non-pathogenic, or blocking certain cites on the pathogenic tau dimer thereby making it unsuitable for aggregation. In certain embodiments, the antibodies do not directly block formation of Tau filaments and/or NFTs, and, instead facilitates the removal/clearance of Tau dimers, e.g., by phagocytosis.

One antibody of the invention is TOC1. TOC1 is a conformation selective antibody that selectively recognizes portions of the proline-rich region and C-terminus of Tau. The variable region of the heavy chain of the antibody ($V_H$) of TOC1 comprises or consists of SEQ ID NO: 7, or a segment thereof, and the variable region of the light chain of the antibody ($V_L$) comprises or consists of SEQ ID NO: 8, or a segment thereof. The Heavy chain of TOC1 comprises or consists of SEQ ID NO: 12, or a segment thereof; and the Light chain of TOC1 comprises or consists of SEQ ID NO: 14 or a segment thereof.

In the preferred embodiments, the antibody is TOC1 antibody, an antibody which has the same or better selectivity for the pathogenic conformation of prefibrillar pathological or neurotoxic tau oligomers and its precursors (i.e., tau dimers) comprising at least two tau proteins, or fragments thereof, cross-linked to each other, directly or through a linker (e.g., B4M), at one or more cysteine residues, or an antibody which retains the specific epitope binding of TOC1 antibody. The epitope of these antibodies may be formed by the conformation induced by two hTau40 cross-linked to each other, directly or through a linker (e.g., B4M), at one or more cysteine residues; by Tau40 cross-linked to ΔTau, directly or through a linker (e.g., B4M), at one or more cysteine residues; or by two ΔTau cross-linked to each other, directly or through a linker (e.g., B4M), at one or more cysteine residues. In all of these embodiments, at least one of the cross-links between the individual tau monomers is, preferably, not a disulfide bridge between cysteines of the tau monomers.

In certain embodiments, the antibody of the invention is not TOC1 antibody, but comprises a variable region of the heavy chain, or a segment thereof, which is the same as or homologous to the variable region, or a segment thereof, of TOC1 antibody (i.e., the antibody comprising $V_H$ of SEQ ID NO: 7, or a segment thereof, and $V_L$ of SEQ ID No: 8, or a segment thereof).

In certain embodiments, the antibody is selective for the conformation recognized by TOC1.

In certain embodiments, the antibody selectively recognizes a conformation induced by crosslinking of two more tau dimers and recognized by TOC1.

In certain embodiments, the antibody selectively binds to an epitope found in a tau oligomer or a tau dimer prepared by cross-linking at least two tau proteins to each other in-vitro, either directly or through a linker, at one or more cysteine residues.

In certain embodiments, the antibody of the invention, the antibody of the invention is not TOMA antibody.

In certain embodiments, the antibody of the invention, the antibody of the invention is not T2286 antibody.

The antibodies of the invention include polyclonal and monoclonal antibodies.

The antibodies of the invention also include recombinant antibodies.

The antibodies of the invention further include, e.g., chimeric antibodies, humanized antibodies, human antibodies, murine antibodies, camelid antibodies, fragments of any of the foregoing (e.g., Fc fragments, Fab fragments, subfragments of any of the foregoing, etc.), and hybrid antibodies (e.g., biselective or bifunctional antibodies).

The antibodies of the invention specifically include single chain antibodies (e.g., camelid antibodies). Single chain antibodies have a potential to penetrate the brain more readily than full-sized immunoglobulins and are less likely to induce unwanted immune reactions.

Any of the antibodies mentioned above may be an IgM or an IgG antibody, or a fragment of any of the foregoing. IgM and IgG antibodies are made up of four polypeptide chains linked together by disulfide bonds. The four chains of whole (intact) IgM and IgG antibodies are two identical heavy chains referred to as H-chains and two identical light chains referred to as L-chains.

In the embodiments where the antibody is an IgG antibody, the IgG antibody may be obtained by an immunoglobulin class switching by rearrangement of a gene of an IgM antibody according to the present invention which will result in the elaboration of IgG antibodies of the same antigenic specificity as the IgM antibody. The gene of the IgM antibody may comprise a fragment which consists of SEQ ID NO: 9, or a segment thereof, and a fragment which consists of SEQ ID NO: 10, or a segment thereof, or fragments homologous thereto. For example, an IgM antibody specific for prefibrillar pathological or neurotoxic tau and precursors comprising comprise at least two tau proteins, or fragments thereof, cross-linked to each other, directly or through a linker (e.g., B4M), at one or more cysteine residues, is formed first. Later the μ constant region of the IgM antibody may be switched with a γ, ε or α constant region to form the heavy chain of the IgG antibody. The antigenic specificity of the B cell will remain the same because the variable regions, diversity segments and joining segments DNA remains the same.

For the production of antibodies, various host animals may be immunized by injection with one or more immunogens described above, which may or may not be conjugated (e.g., to bovine serum albumin), including but not limited to rabbits, mice, rats, etc. using standard immunization protocol (Taggert and Samloff, 1983). Following the completion of immunization, a fusion procedure may be performed using, e.g., splenocytes from the hyperimmunized mice and an appropriate myeloma cell-line SP2/0 Ag14 (ATCC CRL 1581, NS-1 (ATCC TIB18), or equivalent, by using, e.g., polyethylene glycol, and successful fusion products may be selected by means of HAT media and viable hybridoma colonies may then be grown out in well plates. The wells containing successful fusion products may then be screened using, e.g., using ELISA (e.g., specificity and binding affinities) and antibodies selective for prefibrillar pathological or neurotoxic tau and precursors comprising comprise at least two tau proteins, or fragments thereof, cross-linked to each other, directly or through a linker (e.g., B4M), at one or more cysteine residues, and showing no binding and/or no reactivity to other proteins (e.g., monomers of Tau) may be isolated.

Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *corynebacterium parvum*. In certain embodiments, the adjuvant is alum.

Once monoclonal antibodies are generated, the selectivity and binding affinity (Kd) can be evaluated by ELISA, Biacore or other method. For example, in vitro bioassays can be performed on the antibodies to test for the efficacy of the antibodies to selectively bind tau dimers. In vitro bioassays can also be performed on the antibodies to test for the lack of interference with function of the normal tau.

The antibodies selective for the dimers of tau or oligomers of tau, and showing no binding and/or reactivity to normal tau may then be isolated, and, further evaluated in in vivo experiments, e.g., in transgenic AD models. Tg2576 is one example of such a model. Tg2576 is well-characterized and has been used in numerous studies with great reproducibility. Moreover, it has the same Swedish mutation as the hAPP-J20 mouse model used to discover the role of tau in Aβ mediated toxicity. P301L (JNPL3) is another example of a model which may be used. Another transgenic model which could be used, and is preferably used, is a triple transgenic mouse model of Alzheimer's disease (3×Tg-AD) that expresses both plaque and tangle pathology and contains 3 mutations relevant to Alzheimer's pathology ($PS1_{M146V}$, $\beta APP_{Swe}$, and $tau_{P301L}$). The in vivo experiments, if conducted, will assess safety and efficacy of the isolated antibodies, using a variety of methods to measure safety and efficacy, including, e.g., biochemical, neuropathological, imaging and cognitive tools.

In certain embodiments, the antibodies of the invention are raised against electro-eluted cross-linked Tau dimers. In the preferred embodiments, at least one of the cross-links between the individual tau monomers of the electro-eluted cross-linked Tau dimers is not a disulfide bridge between cysteines of the monomers.

The antibodies of the invention, in certain embodiments, may be expressed in-vivo in the brain of a mammal suffering from or at risk of developing a tauopathy (e.g., AD), in response to the administration of a pharmaceutical composition of the invention described below, e.g., a pharmaceutical composition comprising a gene comprising cDNA of one or more antibodies of the invention. In certain embodiments, cDNA comprises SEQ ID NO: 9, or a segment thereof, and a SEQ ID NO: 10, or a segment thereof, or one or more segment which are homologous to any of these sequences or segments thereof.

In a further aspect of the invention, the antibodies according to the present invention or cDNA of these antibodies may be used for the preparation of drug or a pharmaceutical composition for the treatment of tauopathies such as AD by biotechnological modification into single chain molecules equipped with targeting sequence able to deliver them into the neuroblastoma cells expressing tauons, where they bind the tauons and interfere with their pathological effects and increase the degradation of the prefibrillary pathogenic Tau.

In yet another embodiment of the invention, the antibodies of the present invention may be conjugated to a cytoprotective agent directly or through a linker. The cytoprotective agent may be an antioxidant (e.g., melatonin or a different agent capable of cross-linking. The cytoprotective agent should be recognized as safe (GRAS) by the United States Food and Drug Administration ("FDA"). The linker may be selected from the group comprising or consisting of a hydrazine linker, a disulfite linker, a thioether linker, a peptide linker, or the like. In certain embodiments, the antibody is selective for ΔTau, and the cytoprotective agent is melatonin.

In an additional embodiment of the invention, the antibodies of the present invention may be conjugated to an agent which may improve antibody's ability to cross the BBB and is generally recognized as safe (GRAS) by the United States Food and Drug Administration ("FDA"). The agent which facilitates or improves antibody's ability to cross the BBB may be conjugated to the antibody directly or through a linker comprising or consisting of a hydrazine linker, a disulfite linker, a thioether linker, a peptide linker, or the like. The agent which facilitates or improves antibody's ability to cross the BBB may comprise or consists of transferrin, insulin receptor bispecific antibodies or other targeting signals.

Antibodies of the invention are suitable for crossing BBB and for administration, e.g., by a subcutaneous injection, nasal administration, intramuscular injection, IV infusion, transcutaneous injection, buccal administration, oral administration, or as described in more detail below.

Antibodies of the invention may also be used for testing or screening of drugs, for therapeutic monitoring and/or for the determination of the effectiveness of treatment of a tauopathy.

Isolated genes encoding the antibodies of the invention are part of the present invention. In certain embodiments, an isolated gene comprises SEQ ID NO: 9, or a segment thereof, and a SEQ ID NO: 10, or a segment thereof, or one or more segment which are homologous to any of these sequences or segments thereof.

Hybridomas

In an additional aspect, the invention is directed to a hybridoma producing antibodies capable of and selectively recognize prefibrillar pathological or neurotoxic tau and precursors comprising comprise at least two tau proteins, or fragments thereof, cross-linked to each other, directly or through a linker (e.g., B4M), at one or more cysteine residues.

Generally, the hybridoma cells are made in the following manner: (i) a mammal (e.g., a mouse, a camel, etc.) is immunized with an immunogen comprising or consisting of at least two tau proteins, or fragments thereof, cross-linked to each other, directly or through a linker (e.g., B4M), at one or more cysteine residues, or a fragment thereof; (ii) spleen cells from the mammal are grown in a culture dish in the presence of myeloma cells, the strain of the myeloma cells are chosen such that it grows indefinitely in culture, and it does not produce immunoglobulins; (iii) fusion of cell is encouraged by adding certain chemicals (e.g., polyethylene glycol); (iv) the cells are grown in a special culture medium that supports the growth of the fused, hybrid cells but not of the parenteral cells; (v) the resulting clones are screened for the production of antibody capable of and selectively recognize prefibrillar pathological or neurotoxic tau and precursors comprising comprise at least two tau proteins, or fragments thereof, cross-linked to each other, directly or through a linker (e.g., B4M), at one or more cysteine residues.

The selectivity and binding affinity (Kd) of the antibodies can be evaluated and/or confirmed, e.g., by ELISA, Biacore or other method. The antibodies selective for the dimers of tau or oligomers of tau, and showing no binding and/or reactivity to normal tau may be further evaluated in in vivo experiments, e.g., in transgenic AD models (e.g., Tg2576, P301L, or a triple transgenic mouse model of Alzheimer's disease (3×Tg-AD) that expresses both plaque and tangle pathology and contains 3 mutations relevant to Alzheimer's pathology (PS1$_{M146V}$, βAPP$_{Swe}$, and tau$_{P301L}$).

Hybridomas producing antibodies capable of and selectively recognize prefibrillar pathological or neurotoxic tau and precursors comprising comprise at least two tau proteins, or fragments thereof, cross-linked to each other, directly or through a linker (e.g., B4M or N-((2-pyridyldithio)ethyl)-4-azidosalicylamide), at one or more cysteine residues, are selected and isolated.

In the preferred embodiments, the hybridoma contains a fragment of cDNA comprising or consisting of SEQ ID NO: 9, or a segment(s) thereof:

CAGGTCCAACTGCAGCAGCCTGGGGCTGAGCTTGTGATGCCTGGGGCTTCA

GTGAAGCTGTCCTGCAAGGCTTCTGGCTACACCTTCACCAGCTACTGGATG

CACTGGGTGAAGCAGAGGCCTGGACAAGGCCTTGAGTGGATCGGAGAGATT

GATCCTTCTGATAGTTATACTAACTACAATCAAAAGTTCAAGGGCAAGTCC

ACATTGACTGTAGACAAACCCTCCAGCACAGCCTACATGCAGCTCAGCAGC

CTGACATCTGAGGACTCTGCGGTCTATTACTGTGCAAGAAGTGGGGACGGT

AGTAGCCCCTGGTACTTCGATGTCTGGGGCACAGGGACCACGGTCACCGTC

TCCTCA;

and a fragment of DNA comprising or consisting of SEQ ID NO: 10, or a segment(s) thereof:

GATATTGTGATGACACAGTCTACACTCTCCCTGCCTGTCAGTCTTGGAGAT

CAAGCCTCCATCTCTTGCAGATCTAGTCAGAGCATTGTACATAGTAATGGA

AACACCTATTTAGAATGGTACCTGCAGAAACCAGGCCAGTCTCCAAAGCTC

CTGATCTACAAAGTTTCCAACCGATTTTCTGGGGTCCCAGACAGGTTCAGT

GGCAGTGGATCAGGGACAGATTTCACACTCAAGATCAGCAGAGTGGAGGCT

GAGGATCTGGGAGTTTATTACTGCTTTCAAGGTTCACATGTTCCTCGGACG

TTCGGTGGAGGCACCAAGCTGGAAATCAAA.

The fragment of cDNA comprising or consisting of SEQ ID No: 9 encodes V$_H$ of the antibody; and the fragment of cDNA comprising or consisting of SEQ ID No: 10 encodes V$_L$ of the antibody.

The invention also encompasses hybridomas comprising fragments homologous to fragments or segments of SEQ ID NO: 9 and SEQ ID NO: 10.

The DNA sequence encoding Heavy chain of the antibody may comprise or consist of SEQ ID NO: 11, or a fragment thereof; and the DNA sequence encoding the Light chain of the antibody may comprise or consist of SEQ ID NO: 13, or a fragment thereof.

In addition, the DNA sequence encoding Heavy chain of the antibody may comprise or consist of a sequence homologous to SEQ ID NO: 11, or a fragment thereof; and the DNA sequence encoding the Light chain of the antibody may comprise or consist of a sequence homologous to SEQ ID NO: 13, or a fragment thereof.

Hybridomas of the invention may produce virtually unlimited quantities of monoclonal antibodies that may be used in the preparation of pharmaceutical compositions and diagnostic compositions of the invention.

Epitopes

In a further aspect, the invention is directed to isolated epitopes of the antibodies of the invention. These antibodies were described above.

An isolated epitope of the invention may comprise two tau proteins, or fragments thereof. For example, the epitope of the antibodies may be formed by a conformation created by two hTau40 cross-linked to each other, directly or through a linker (e.g.,), at one or more cysteine residues. The epitope of the antibodies may also be formed by a conformation created by Tau40 cross-linked to ΔTau, directly or through a linker (e.g., B4M), at one or more cysteine residues. The epitope of the antibody may additionally be formed by conformation created by two ΔTau cross-linked to each other, directly or through a linker (e.g., B4M), at one or more cysteine residues. In any of these embodiments, the linker may be an agent which has a sulfhydryl (SH) group and is capable of reacting with available cites upon UV illumination. The linker may, e.g., be selected from the group consisting of B4M, PEAS (N-((2-pyridyldithio)ethyl)-4-azidosalicylamide), succinimidyl trans-4-(maleimidylmethyl)cyclohexane-1-carboxylate (SMCC), 3-(2-pyridyldithio)propionate (SPDP), 2,5-Pyrrolidinedione, 1-[1-oxo-3-(2-pyridinyldithio)propoxy], succinimidyl acetylthioacetate (SATA), N-((2-pyridyldithio)ethyl)-4-azidosalicylamide), or the like. In the preferred embodiments, however, the linker is B4M.

The isolated epitope of the antibodies may comprises or consists of a fragment comprising or consisting of amino acid residues 221-228, or a portion thereof, of hTau40. In some of these embodiments, the epitope comprises or consists of a four, five, six, or seven amino acid segment from amino acid residues 221-228 of hTau40.

The isolated epitope of the antibodies may comprises or consists of an amino acid sequence corresponding to two different regions of tau (e.g., hTau40): (a) a first region comprising or consisting of an amino acid sequence of a proline-rich region of Tau (i.e., residues 155-244 of hTau40), or a segment(s) thereof, and (b) a second region comprising or consisting of an amino acid sequence of a fragment from the carboxy terminal region of tau (e.g., residues 376-441 or residues 376-421 of hTau40) or a segment(s) thereof. The first region may consist of a peptide consisting of a fragment from the proline region of Tau (i.e., residues 155-244 of hTau40) consisting from 4 to 80 residues, from 5 to 70 residues, from 5 to 60 residues, from 5 to 50, from 5 to 40 residues, from 5 to 35 residues, 5 to 30 residues, from 5 to 25 residues, from 5 to 20 residues, from 5 to 15 residues, from 5 to 12 residues, from 5 to 10 residues, from 5 to 9 residues of the proline-rich region of hTau40, and the second region may consist of a peptide consisting of a fragment from the carboxy terminal region of Tau (residues 376-441 or residues 376-421 of hTau40) consisting of from 5 to 60 residues, from 5 to 50, from 5 to 40 residues, from 5 to 35 residues, 5 to 30 residues, from 5 to 25 residues, from 5 to 20 residues, from 5 to 15 residues, from 5 to 12 residues, from 5 to 10 residues, from 5 to 9 residues from the carboxy terminal region of Tau (e.g., hTau40).

In some of these embodiments, the fragment from the proline region of hTau40 consists of residues 155-244, residues 160-240, residues 170-235, residues 180-230, residues 190-230, residues 195-230, residues 200-230, residues 205-230, residues 210-230, residues 212-230, residues 215-229, residues 218-229, residues 219-229, residues 220-229, residues 221-228, a segment(s) of any of the foregoing, or a combination of any of the foregoing of hTau40; and the fragment from the carboxy terminal region of hTau40 consists of residues 376-441, residues 376-421, residues 380-421, residues 390-421, residues 400-421, residues 410-421, residues 412-421, residues 415-421, residues 416-421, a segment(s) of any of the foregoing, or a combination of any of the foregoing of hTau40. Thus, the fragment from the proline region of hTau40 may consist, e.g., residues 221-228, or a segment(s) thereof, of hTau40, and the fragment from the carboxy terminal region of hTau40 may consist from residues 400-421, or a segment(s) thereof, of hTau40.

In some of these embodiments, the fragment from the proline region of hTau40 consists of residues 221-228, or portion thereof, and a segment(s) of any of the foregoing, or a combination of any of the foregoing of hTau40; and the fragment from the carboxy terminal region of hTau40 consists of residues 376-441, residues 376-421, residues 380-421, residues 390-421, residues 400-421, residues 410-421, residues 412-421, residues 415-421, residues 416-421, a segment(s) of any of the foregoing, or a combination of any of the foregoing of hTau40.

The isolated epitope of the antibody, or a segment(s) thereof, may lay within ninety amino acids of a MTBR of hTau40, and does not include any of the MTBRs.

The isolated epitope of the present invention may be an intermolecular and/or intramolecular epitope.

The isolated epitope of the invention may comprise or consists of an amino acid sequence, or a segment(s) thereof, selectively recognized by an antibody comprising a $V_H$ comprising or consisting of SEQ ID NO: 7, or a segment(s) thereof, and a $V_L$ comprising or consisting of SEQ ID NO: 8, or a segment(s) thereof.

The isolated epitope of the invention may comprise or consists of an amino acid sequence, or a segment(s) thereof, selectively recognized by an antibody comprising a Heavy chain of SEQ ID NO: 12 or a fragment thereof; and a Light chain comprising or consisting of SEQ ID NO: 14 or a fragment thereof.

The isolated epitope of the invention may be obtained from a commercial source or synthesized denovo by using a number of numerous well known synthetic recombinant techniques, including, e.g., techniques used to transform cells, construct vectors, extract messenger RNA, prepare cDNA libraries, and the like. These techniques are widely practiced in the art, and most practitioners are familiar with the standard resource materials which describe specific conditions and procedures widely practiced in the art. For example, the tau monomer may be synthesized by solid phase peptide synthesis or recombinant expression, or can be obtained from natural sources.

The isolated epitope, or a segment(s) thereof, of the invention may be used as an immunogen to generate antibodies capable of and selectively recognizing prefibrillar pathological or neurotoxic tau and precursors comprising at least two tau proteins, or segments thereof, cross-linked to each other, directly or through a linker (e.g., B4M), at one or more cysteine residues, as described above.

In certain embodiments, the epitope is an isolated epitope of TOC1, or a portion thereof. The epitope comprises a fragment consisting of amino acids 221-228 or a portion thereof.

The TOC1 epitope is readily demonstrable in dot blots of aggregated tau, in immuno-gold EM, and in immunohistochemistry. In these non-denaturing assays, the TOC1 site is available for binding in oligomers or dimers, but not in monomers and polymers (filaments). It appears that TOC1, while in monomer or polymer form, obscures its epitope; this is why it can be seen on tau immunoblots following SDS-PAGE.

Pharmaceutical Compositions

Pharmaceutical formulations in accordance with the present invention may comprise (i) an active agent comprising or consisting of (a) one or more antibody[ies] capable of selectively recognizing prefibrillar pathological or neurotoxic tau and precursors comprising at least two tau proteins, or fragments thereof, cross-linked to each other, directly or through a linker (e.g., B4M), at one or more cysteine residues, as described above, (b) one or more immunogenic peptide[s] comprising at least two tau proteins cross-linked to each other, either directly or through a linker (e.g., B4M) at one or more cysteine residues, as described above, (c) one or more segment[s] of the immunogenic peptides, (d) one or more segments[s] of the antibodies, and (e) isolated genes or cDNA sequences encoding the antibodies, (f) mixtures of any the foregoing and (ii) one or more pharmaceutically acceptable excipients. In the preferred embodiments, at least one of the cross-links between the individual tau monomers is not a disulfide bridge between cysteines of the monomers.

The active agent may also include one or more antibodies which are free end-specific of Aβ peptides and/or one or more immunogens for these antibodies; and/or a plurality of antibodies which recognize and bind ΔTau and do not recognize and do not bind hTau40, and/or one or more immunogens for these antibodies.

The specific embodiments contemplated include, for example:

1) pharmaceutical composition comprising an active agent comprising one or more antibody[ies] capable of selectively recognizing prefibrillar pathological or neurotoxic tau and precursors comprising at least two tau proteins, or fragments thereof, cross-linked to each other, directly or through a linker (e.g., B4M), at one or more cysteine residues, as described above, and/or one more immunogens for these antibodies;

2) pharmaceutical composition comprising an active agent comprising (i) one or more antibody[ies] capable of selectively recognizing prefibrillar pathological or neurotoxic tau and precursors comprising at least two tau proteins, or fragments thereof, cross-linked to each other, directly or through a linker (e.g., B4M), at one or more cysteine residues, as described above, and/or one more immunogens for these antibodies, and (ii) one or more antibodies which are free end-specific of Aβ peptides and/or one or more immunogens for these free end-specific antibodies;

3) pharmaceutical composition comprising an active agent comprising (i) one or more antibody[ies] capable of selectively recognizing prefibrillar pathological or neurotoxic tau and precursors comprising at least two tau proteins, or fragments thereof, cross-linked to each other, directly or through a linker (e.g., B4M), at one or more cysteine residues, as described above, and/or one more immunogens for these antibodies, and (ii) one or more antibodies which recognize and bind ΔTau and do not recognize and do not bind htau1-40, and/or one or more immunogens for these ΔTau antibodies; and 4) pharmaceutical composition comprising an active agent comprising (i) one or more antibody[ies] capable of selectively recognizing prefibrillar pathological or neurotoxic tau and precursors comprising at least two tau proteins, or fragments thereof, cross-linked to each other, directly or through a linker (e.g., B4M), at one or more cysteine residues, as described above, and/or one more immunogens for these antibodies; (ii) one or more antibodies which are free end-specific of Aβ peptides and/or one or more immunogens for these free end-specific antibodies; and (iii) one or more antibodies which recognize and bind ΔTau and do not recognize and do not bind htau1-40, and/or one or more immunogens for these ΔTau antibodies.

The active agent(s) will generally comprise from about 0.01% to about 90% of the formulation, and the one or more excipients will generally comprise from about 10% to about 99.99% of the formulation. In the preferred embodiments, the formulations are used for introduction of the active agent into a body of a living mammal (e.g., a human) and are accompanied with instructions (e.g., a package insert) which recite directions for administration of the active agent into the body of the living mammal. In some of these embodiments, the formulations are used for treatment or prevention of AD and/or another tauopathy and are accompanied by the instructions which recited directions for treatment and/or prevention of AD and/or another tauopathy.

Pharmaceutical compositions of the present invention, in certain embodiments, may comprise a gene encoding an antibody capable of selectively recognizing pathogenic tau dimers and prefibrillar pathological or neurotoxic tau. Antibodies capable of selectively recognizing pathogenic tau dimers and prefibrillar pathological or neurotoxic tau were described above. In certain embodiments, the isolated gene comprises a fragment of SEQ ID NO: 9, or a segment(s) thereof, and a fragment of SEQ ID NO: 10, or a segment(s) thereof, or one or more fragments or segments which are homologous to any of these fragments or segments.

Pharmaceutical compositions in accordance with the present invention can be administered by parenteral, topical, intranasal, intravenous, oral, subcutaneous, intraarterial, intracranial, intraperitoneal, intranasal, or intramuscular means for prophylactic and/or therapeutic treatment. The pharmaceutical compositions can be administered intravenously, intracerebrally, intranasally, orally, transdermally, buccally, intra-arterially, intracranially, or intracephalically. The most typical route of administration of an immunogenic agent is subcutaneous although other routes can be equally effective. The next most common route is intramuscular injection. This type of injection is most typically performed in the arm or leg muscles. In some methods, agents are injected directly into a particular tissue where deposits have accumulated, for example intracranial injection. For compositions comprising antibodies, intramuscular injection or an intravenous infusion may be preferred. A preferred route of administration for certain antibodies (e.g., camelid antibodies) may be oral. In some methods, particular therapeutic antibodies are injected directly into the cranium. In some methods, antibodies are administered as a sustained release composition or device, such as a Medipad™ device (Elan Pharm. Technologies, Dublin, Ireland). In certain embodiments, the adjuvant is alum.

The pharmaceutical formulations in accordance with the present invention may also contain one or more pharmaceutical carriers and/or suitable adjuvants.

A therapeutically effective amount of the antibody of the invention may vary according to factors such as the disease state, age, sex, and weight of the individual, and the ability of the modulator to elicit a desired response in the individual. Dosage regimens may be adjusted to provide the optimum therapeutic response. A therapeutically effective amount is also one in which any toxic or detrimental effects of the modulator are outweighed by the therapeutically beneficial effects.

A "prophylactically effective amount" (e.g., of an antibody capable of selectively recognizing prefibrillar pathological or neurotoxic tau and precursors comprising at least two tau proteins, or fragments thereof, cross-linked to each other, directly or through a linker (e.g., B4M), at one or more cysteine residues, as described above) refers to an amount effective, at dosages and for periods of time necessary, to achieve the desired prophylactic result, such as preventing or inhibiting the rate of tau deposition, aggregation, polymerization and/or neurotoxicity in a subject predisposed to the formation of neurofibrillary tangles. A prophylactically effective amount can be determined as described above for the therapeutically effective amount. Typically, since a prophylactic dose is used in subjects prior to or at an earlier stage of disease, the prophylactically effective amount will be less than the therapeutically effective amount. A "therapeutically effective amount" refers to an amount effective, at dosages and for periods of time necessary, to achieve the desired therapeutic rest, such as slowed progression of Alzheimer's disease, delayed onset, reduction or reversal of aggregate formation and/or neurofibrillary tangles, and/or reduction or reversal of neurotoxicity. A therapeutically effective amount of the antibody of the invention may vary according to factors such as the disease state, age, sex, and weight of the individual, and the ability of the modulator to elicit a desired response in the individual. Dosage regimens may be adjusted to provide the optimum therapeutic response. A therapeutically effective amount is also one in which any toxic or detrimental effects of the modulator are outweighed by the therapeutically beneficial effects.

One factor that may be considered when determining a therapeutically or prophylactically effective amount of an antibody capable of selectively recognizing prefibrillar pathological or neurotoxic tau and precursors comprising at least two tau proteins, or fragments thereof, cross-linked to each other, directly or through a linker (e.g., B4M), at one or more cysteine residues, as described above is the concentration of tau dimers in a biological compartment of a subject, such as in the cerebrospinal fluid (CSF) or the plasma of the subject. It is to be noted that dosage values may vary with the severity of the condition to be alleviated. It is to be further understood that for any particular subject, specific dosage regimens could be adjusted over time according to the individual need and the professional judgment of the person administering or supervising the administration of the compositions. For example, a single bolus may be administered, several divided doses may be administered over time or the dose may be proportionally reduced or increased as indicated by the exigencies of the therapeutic situation.

It is especially advantageous in certain embodiments to formulate parenteral compositions in dosage unit form for ease administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals. As used herein "pharmaceutically acceptable carrier" includes any and all solvents, dispersion media, coatings, antibacterial and antifungal agents, isotonic and absorption delaying agents, and the like that are physiologically compatible. In one embodiment, the carrier is suitable for parenteral administration. Preferably, the carrier can be suitable for intravenous, intraperitoneal or intramuscular administration. Alternatively, the carrier is suitable for administration into the central nervous system (e.g., intraspinally or intracerebrally). In another embodiment, the carrier is suitable for oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Formulations prepared in accordance with the present invention typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, the antibody can be administered in a time-release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

Sterile injectable solutions can be prepared by incorporating the active compound (e.g., antibody to the prefibrillar pathogenic tau in the required amount) in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Topical application can result from intransdermal or intradermal application. Topical administration can be facilitated by coadministration of the agent with cholera toxin or detoxified derivatives or subunits thereof. Alternatively, transdermal delivery can be achieved using skin patch or using transfersomes.

Other delivery systems can include time-release, delayed release or sustained release delivery systems. Such systems can avoid repeated administrations of the active compounds of the invention, increasing convenience to the subject and the physician. Many types of release delivery systems are available and known to those of ordinary skill in the art. They include polymer based systems such as polylactic and polyglycolic acids polyanhydrides and polycaprolactone; nonpolymer systems that are lipids including sterols such as cholesterol, cholesterol esters and fatty acids or neutral fats such as mono-, di and triglycerides; hydrogel release systems; silastic systems; peptide based systems; wax coatings, compressed tablets using conventional binders and excipients, partially fused implants and the like. In addition, a pump-based hardware delivery system can be used, some of which are adapted for implantation.

A long-term sustained release implant also may be used. "Long-term" release, as used herein, means that the implant is constructed and arranged to deliver therapeutic levels of the active ingredient for at least 30 days, and preferably 60 days. Long-term sustained release implants are well known to those of ordinary skill in the art and include some of the release systems described above. Such implants can be particularly useful in treating conditions characterized by aggregates of amyloid beta peptides by placing the implant near portions of the brain affected by such aggregates, thereby effecting localized, high doses of the compounds of the invention.

Immunogenic agents of the present invention, such as peptides, are sometimes administered in combination with an adjuvant. A variety of adjuvants can be used in combination with a peptide, such as tau, to elicit an immune response. Preferred adjuvants augment the intrinsic response to an immunogen without causing conformational changes in the immunogen that affect the qualitative form of the response.

A preferred class of adjuvants is aluminum salts (alum), such as aluminum hydroxide, aluminum phosphate, and aluminum sulfate. Such adjuvants can be used with or without other specific immunostimulating agents, such as 3 De-O-acylated monophosphoryl lipid A (MPL) or 3-DMP, polymeric or monomeric amino acids, such as polyglutamic acid or polylysine. Such adjuvants can be used with or without other specific immunostimulating agents, such as muramyl peptides (e.g., N-acetylmuramyl-L-threonyl-D-isoglutamine (thr-MDP), N-acetyl-normuramyl-L-alanyl-D-isoglutamine (nor-MDP), N-acetylmuramyl-L-alanyl-D-isoglutaminyl-L-alanine-2-(1'-2' dipalmitoyl-sn-glycero-3-hydroxyphosphoryloxy)-ethylamine (MTP-PE), N-acetylglucsaminyl-N-acetylmuramyl-L-Al-D-isoglu-L-Ala-dipalmitoxy propylamide (DTP-DPP) Theramide™), or other bacterial cell wall components. Oil-in-water emulsions include (a) MF59 (WO 90/14837 to Van Nest et al., which is hereby incorporated by reference in its entirety), containing 5% Squalene, 0.5% Tween 80, and 0.5% Span 85 (optionally containing various amounts of MTP-PE) formulated into submicron particles using a microfluidizer such as Model 110Y microfluidizer (Microfluidics, Newton Mass.), (b) SAF, containing 10% Squalene, 0.4% Tween 80, 5% pluronic-blocked polymer L121, and thr-MDP, either microfluidized into a submicron emulsion or vortexed to generate a larger particle size emulsion, and (e) Ribi™ adjuvant system (RAS), (Ribi ImmunoChem, Hamilton, Mont.) containing 2% squalene, 0.2% Tween 80, and one or more bacterial c ell wall components from the group consisting of monophosphoryllipid A (MPL), trehalose dimycolate (TDM), and cell wall skeleton (CWS), preferably MPL+CWS (Detox™). Other adjuvants include Complete Freund's Adjuvant (CFA) and Incomplete Freund's Adjuvant (IFA). Other adjuvants include cytokines, such as interleukins (IL-1, IL-2, and IL-12), macrophage colony stimulating factor (M-CSF), and tumor necrosis factor (TNF). In certain embodiments, the adjuvant is ilum.

An adjuvant can be administered with an immunogen as a single composition, or can be administered before, concurrent with, or after administration of the immunogen. Immunogen and adjuvant can be packaged and supplied in the same vial or can be packaged in separate vials and mixed before use. Immunogen and adjuvant are typically packaged with a label, indicating the intended therapeutic application. If immunogen and adjuvant are packaged separately, the packaging typically includes instructions for mixing before use. The choice of an adjuvant and/or carrier depends on the stability of the immunogenic formulation containing the adjuvant, the route of administration, the dosing schedule, the efficacy of the adjuvant for the species being vaccinated, and, in humans, a pharmaceutically acceptable adjuvant is one that has been approved or is approvable for human administration by pertinent regulatory bodies. For example, Complete Freund's adjuvant is not suitable for human administration. However, alum, MPL or Incomplete Freund's adjuvant (Chang et al., Advanced Drug Delivery Reviews 32:173-186 (1998), which is hereby incorporated by reference in its entirety) alone or optionally all combinations thereof are suitable for human administration.

Agents of the present invention are often administered as pharmaceutical compositions comprising an active therapeutic agent and a variety of other pharmaceutically acceptable components. See Remington's Pharmaceutical Science (15th ed., Mack Publishing Company, Easton, Pa., 1980), which is hereby incorporated by reference in its entirety. The preferred form depends on the intended mode of administration and therapeutic application. The compositions can also include, depending on the formulation desired, pharmaceutically-acceptable, non-toxic carriers or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like.

Pharmaceutical compositions can also include large, slowly metabolized macromolecules, such as proteins, polysaccharides like chitosan, polylactic acids, polyglycolic acids and copolymers (e.g., latex functionalized sepharose, agarose, cellulose, and the like), polymeric amino acids, amino acid copolymers, and lipid aggregates (e.g., oil droplets or liposomes). Additionally, these carriers can function as immunostimulating agents (i.e., adjuvants).

For parenteral administration, agents of the present invention can be administered as injectable dosages of a solution or suspension of the substance in a physiologically acceptable diluent with a pharmaceutical carrier that can be a sterile liquid such as water, oil, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin. Peanut oil, soybean oil, and mineral oil are all examples of useful materials. In general, glycols, such as propylene glycol or polyethylene glycol, are preferred liquid carriers, particularly for injectable solutions. Agents of the invention, particularly, antibodies, can be administered in the form of a depot injection or implant preparation which can be formulated in such a manner as to permit a sustained release of the active ingredient. An exemplary composition comprises monoclonal antibody at 5 mg/mL, formulated in aqueous buffer consisting of 50 mM L-histidine, 150 mM NaCl, adjusted to pH 6.0 with HCl.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles, such as polylactide, polyglycolide, or copolymer, for enhanced adjuvant effect (Langer, et al., Science 249:1527 (1990); Hanes, et al., Advanced Drug Delivery Reviews 28:97-119 (1997), which are hereby incorporated by reference in their entirety).

Additional formulations suitable for other modes of administration include oral, intranasal, and pulmonary formulations, suppositories, and transdermal applications.

For suppositories, binders and carriers include, for example, polyalkylene glycols or triglycerides; such suppositories can be formed from mixtures containing the active ingredient in the range of 0.5% to 10%, preferably 1%-2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

Topical application can result in transdermal or intradermal delivery. Topical administration can be facilitated by co-administration of the agent with cholera toxin or detoxified derivatives or subunits thereof or other similar bacterial toxins (See Glenn et al., Nature 391:851 (1998), which is hereby incorporated by reference in its entirety). Co-administration can be achieved by using the components as a mixture or as linked molecules obtained by chemical crosslinking or expression as a fusion protein. Alternatively, transdermal delivery can be achieved using a skin path or using transferosomes (Paul et al., Eur. J. Immunol. 25:3521-24 (1995); Cevc et al., Biochem. Biophys. Acta 1368:201-15 (1998), which are hereby incorporated by reference in their entirety).

Vaccines

One particular pharmaceutical composition contemplated by the present invention is a vaccine. A vaccine in accordance with the present invention may be used to provide passive immunization and/or active immunization to a mammal.

A vaccine for passive immunization may comprise one or more antibody[ies] capable of selectively recognizing prefibrillar pathological or neurotoxic tau and precursors comprising at least two tau proteins, or fragments thereof, cross-linked to each other, directly or through a linker (e.g., B4M), at one or more cysteine residues including their pathogenic conformation. In certain embodiments, at least one of the cross-links between the individual tau monomers is not a disulfide bridge between cysteines of the monomers.

The vaccine for active immunization may comprise an immunogenic peptide of the present invention comprises at least two tau proteins cross-linked to each other, either directly or through a linker (e.g., B4M) at one or more cysteine residues, or a segment(s) thereof. In certain embodiments, at least one of the cross-links between the individual tau monomers is not a disulfide bridge between cysteines of the monomers.

The vaccine for active immunization may also comprise one or more epitopes of the antibody[ies] capable of selectively recognizing prefibrillar pathological or neurotoxic tau and precursors, including their pathogenic conformation.

The antibodies, immunogens and epitopes suitable for inclusion into vaccines of the invention were described in detail above.

Any one of these vaccines may include also one or more antibodies which are free end-specific of Aβ peptides and/or one or more immunogens for these antibodies; and/or a plurality of antibodies which recognize and bind ΔTau and do not recognize and do not bind htau1-40, and/or one or more immunogens for these antibodies. Some of the embodiments contemplated were described above the Pharmaceutical Composition section.

The vaccine may also additionally comprise one or more pharmaceutically acceptable excipients as described above and, in certain embodiments, one or more mimotopes of any of the antibodies mentioned above, and may be administered as described above (e.g., intravenously, subcutaneously, intranasally or intracranially).

Therapy

Administration of the immunogenic peptides, immunogenic epitopes thereof, antibodies, pharmaceutical compositions, vaccines, all as described above, or any combinations thereof can be used as a therapy to treat Alzheimer's disease, or other tauopathy associated with the development of neurofibrillary tangles. Additionally, the administration of these substances and compositions can also be used as a prophylactic treatment to immunize against Alzheimer's disease, or other tauopathy associated with the neurofibrillary tangle.

Patients amenable to treatment include individuals at risk of disease but not showing symptoms, as well as patients presently showing symptoms. In the case of Alzheimer's disease, virtually anyone is at risk of suffering from Alzheimer's disease. Therefore, the present methods can be administered prophylactically to the general population without the need for any assessment of the risk of the subject patient. Such prophylactic administration can begin at, e.g., age 50 or greater. The present methods are especially useful for individuals who do have a known genetic risk of Alzheimer's disease. Such individuals include those having relatives who have experienced this disease and those whose risk is determined by analysis of genetic or biochemical markers. Genetic markers of risk toward Alzheimer's disease include mutations in the APP gene, particularly mutations, at position 717 and positions 670 and 671 referred to as the Hardy and Swedish mutations respectively. Other markers of risk are mutations in the presenilin genes, PS1 and PS2, and ApoE4, family history of AD, hypercholesterolemia or atherosclerosis. Individuals presently suffering from Alzheimer's disease can be recognized from characteristic dementia by the presence of risk factors described above. In addition, a number of diagnostic tests are available for identifying individuals who have AD. These include imaging, and/or measurement of CSF tau and Aβ42 levels. Elevated tau and decreased Aβ42 levels signify the presence of AD. Individuals suffering from Alzheimer's disease can also be diagnosed by Alzheimer's Disease and Related Disorders Association criteria.

In asymptomatic patients, treatment can begin at any age (e.g., 10, 20, 30, 40, 50, or 60). Usually, however, it is not necessary to begin treatment until a patient reaches 40, 50, 60, 70, 75 or 80. Treatment typically entails multiple dosages over a period of time. Treatment can be monitored by assaying antibody, or activated T-cell or B-cell responses to the therapeutic agent over time. If the response falls, a booster dosage is indicated. In the case of potential Down's syndrome patients, treatment can begin antenatally by administering therapeutic agent to the mother or shortly after birth.

In prophylactic applications, pharmaceutical compositions or medicaments are administered to a patient susceptible to, or otherwise at risk of, Alzheimer's disease in an amount sufficient to eliminate or reduce the risk, lessen the severity, or delay the outset of the disease, including biochemical, histologic and/or behavioral symptoms of the disease, its complications and intermediate pathological phenotypes presented during development of the disease. In therapeutic applications, compositions or medicaments are administered to a patient suspected of, or already suffering from, such a disease in an amount sufficient to cure, or at least partially arrest, the symptoms of the disease biochemical, histologic and/or behavioral), including its complications and intermediate pathological phenotypes in development of the disease. In some methods, administration of agent reduces or eliminates mild cognitive impairment in patients that have not yet developed characteristic Alzheimer's pathology. An amount adequate to accomplish therapeutic or prophylactic treatment is defined as a therapeutically- or prophylactically-effective dose. In both prophylactic and therapeutic regimes, agents are usually administered in several dosages until a sufficient immune response has been achieved. Typically, the immune response is monitored and repeated dosages are given if the immune response starts to wane.

Effective doses of the compositions of the present invention, for the treatment of the above described conditions vary depending upon many different factors, including means of administration, target site, physiological state of the patient, other medications administered, and whether treatment is prophylactic or therapeutic. Treatment dosages need to be titrated to optimize safety and efficacy.

An additional advantage of the selective antibodies of the present invention, in certain embodiments, may be that, for equal mass dosages, dosages of antibodies that selectively recognizing the conformation of the prefibrillar pathological or neurotoxic tau oligomers and their precursors (i.e., tau dimers) comprising at least two tau proteins, or fragments thereof, cross-linked to each other, directly or through a linker (e.g., B4M), at one or more cysteine residues contain a higher molar dosage of the antibodies effective in clearing and/or "inactivating," than a composition comprising a mixture of the selective antibodies and non-selective antibodies.

The amount of immunogen depends on whether adjuvant is also administered, with higher dosages being required in the absence of adjuvant. Generally, the amount of an immunogen for administration sometimes varies from 1-500 µg per patient and more usually from 5-500 µg per injection for human administration. Occasionally, a higher dose of 1-2 mg per injection is used. Typically about 10, 20, 50, or 100 µg is used for each human injection. The mass of immunogen also depends on the mass ratio of immunogenic epitope within the immunogen to the mass of immunogen as a whole. Typically, $10^{-3}$ to $10^{-5}$ micromoles of immunogenic epitope are used for each microgram of immunogen. The timing of injections can vary significantly from once a day, to once a year, to once a decade. On any given day that a dosage of immunogen is given, the dosage is greater than 1 µg/patient and usually greater than 10 µg patient if adjuvant is also administered, and greater than 10 µg/patient and usually greater than 100 µg/patient in the absence of adjuvant. A typical regimen consists of an immunization followed by booster injections at time intervals, such as 6 week intervals. Another regimen consists of an immunization followed by booster injections 1, 2, and 12 months later. Another regimen entails an injection every two months for life. Alternatively, booster injections can be on an irregular basis as indicated by monitoring of immune response.

For passive immunization with an antibody, the dosage ranges from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once per every two weeks or once a month or once every 3 to 6 months. In some methods, two or more antibodies (e.g., recombinant, monoclonal, chimeric and/or humanized) with the same or different binding specificities are administered simultaneously, in which case the dosage of each antibody administered falls within the ranges indicated. In such circumstances, the two or more antibodies may both be directed at, e.g., truncated tau. Alternatively, one or more of the antibodies may be directed at, e.g., truncated tau, and one or more additional antibodies may be directed at amyloid-β (Aβ) peptides associated with Alzheimer's disease. Antibodies are usually administered on multiple occasions. Intervals between single dosages can be hourly, daily, weekly, monthly, or yearly. In some methods, dosage is adjusted to achieve a plasma antibody concentration of 1-1000 µg/ml and in some methods 25-300 µg ml. Alternatively, antibody can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

Doses for nucleic acids encoding immunogens range from about 10 ng to 1 g, 100 ng to 100 mg, 1 µg to 10 mg, or 30-300 µg DNA per patient. Doses for infectious viral vectors vary from 10-100, or more, virions per dose.

The efficacy of the administration/treatment may be accessed by measuring levels of neurotoxic tau in plasma and/or CSF. Based on this assessment, the dose and/or frequency of administration may be adjusted accordingly. In addition or in alternative, the efficacy of administration/treatment is accessed by, e.g., monitoring the number of NFTs.

In addition or in alternative, the efficacy of the administration/treatment may also be accessed by amyloid plaques imaging by PET. An increase in brain's metabolism would indicate that the administration/treatment is effective. The efficacy may further be accessed by a degree of brain atrophy, as determined by MRI.

In addition or in alternative, the efficacy of the administration/treatment may be accessed by measuring the levels of IgG and IgM against dimer of tau or oligomers of tau.

The safety of the administration/treatment may be accessed by monitoring for microhemorrhages and/vasogenic edema, e.g., by MRI. Based on this assessment, the dose and/or frequency of administration may be adjusted accordingly.

Antibodies and immunogens may be administered intranasally, by a subcutaneous injection, intramuscular injection, IV infusion, transcutaneously, buccally, etc., alone or in combination with other immunological therapeutic agent(s) for the treatment of tauopathies (e.g., AD).

Diagnostic Compositions

In an additional aspect, the invention is directed to the use of the antibodies capable of selectively recognizing pathological tau dimers and prefibrillar pathological or neurotoxic oligomers in the diagnosis and monitoring of tauopathies (e.g., AD), including pathogenic conformations of pathological tau dimers and prefibrillar pathological or neurotoxic oligomers, and/or in the preparation of the diagnostic compositions for diagnosis and monitoring of tauopathies (e.g., AD). For example, these diagnostic compositions may be used to measure association of the pathogenic dimers and prefibrillar pathogenic oligomers with the antibodies, and subsequently quantifying the amount of pathogenic oligomers and dimers in a mammal or determining a stage of pathology based on this association.

These diagnostic compositions may also be used to identify mammals starting to develop a tauopathy (e.g., AD) well before these mammals begin to show signs of cognitive decline and dementia, as these antibodies selectively recognizing pathological tau dimers and prefibrillar pathological or neurotoxic oligomers which appear early in the development of tauopathies (e.g., at least 10 years before signs of dementia and mental decline begin to appear).

The diagnostic compositions may comprise one or more antibodies capable of selectively recognizing pathogenic tau dimer and/or prefibrillar pathological or neurotoxic Tau, including their pathogenic conformation (e.g., one or more TOC-1 antibodies). The antibodies which selectively recognize a pathogenic tau dimer and/or prefibrillar pathological or neurotoxic Tau were described above.

The diagnostic composition may also include a detectable agent. The detectable agent may be a radioactive marker, a nucleic acid, a fluorescent label, an enzymatic label. The detecting agent may be included as a separate component of the diagnostic composition or may be conjugated to the antibody which selectively recognizes a pathogenic tau dimer and/or prefibrillar pathological or neurotoxic Tau. In certain embodiments, however, a portion of the antibody may act as a diagnostic agent.

Immunohistochemical and biochemical methods using antibodies capable of selectively recognizing pathogenic tau dimer and/or prefibrillar pathological or neurotoxic Tau, alone or, in in combination with other well characterized antibodies (e.g., TAC-3), may be used to make qualitative and quantitative analysis of the levels, localization and post translational modifications of pathogenic tau dimer and/or prefibrillar pathological or neurotoxic Tau in brain samples of mammals and age-matched controls, and/or quantify pathogenic tau dimer and/or prefibrillar pathological or neurotoxic Tau in a large number of CSF samples. These samples can be analyzed biochemically by direct ELISA, immunoprecipitation/western, and sandwich ELISA, e.g., to quantify the amount/level of recognizing pathogenic tau dimer and/or prefibrillar pathological or neurotoxic Tau.

In one embodiment, the diagnostic composition may be in the form of a test for early detection of AD, or another tauopathy. A detection of pathogenic tau dimer and/or prefibrillar pathological or neurotoxic Tau in the CSF by the antibodies capable of selectively recognizing pathogenic tau dimer and/or prefibrillar pathological or neurotoxic Tau in accordance with the present invention may be used as a biomarker of AD. CSF is in direct contact with CNS, and therefore changes in the biochemical composition of CSF (e.g., presence of the pathogenic tau dimer and/or prefibrillar pathological or neurotoxic Tau) would be evidence of the presence of pathogenic tau dimer and/or prefibrillar pathological or neurotoxic Tau in the CNS brain, and therefore may serve as an early diagnosis of AD. CSF may be obtained from a mammal in need of testing or at risk of developing a tauopathy by, e.g., means of a lumbar puncture.

In one embodiment, the diagnostic composition is a kit comprising (i) one or more antibodies described above, including fragments thereof and (ii) one or more epitopes or immunogens described above. The kit may be used, e.g., for testing or screening of drugs, for therapeutic monitoring and/or for the determination of the effectiveness of treatment of tauopathy.

In an additional embodiment, the diagnostic composition is a kit for diagnosing Alzheimer's disease, the kit comprising a detection means for pathogenic tau dimers and/or prefibrillar pathogenic oligomers of tau. The detection means, generally, comprises one or more antibodies described above, including fragments thereof. The kit may further comprise one or more epitopes or immunogens described above.

In an additional embodiment, the diagnostic composition is a kit for diagnosing Alzheimer's disease, the kit comprising a quantification means for quantitatively detecting pathogenic tau dimers and/or prefibrillar pathogenic oligomers of tau. The quantification means, generally, comprises one or more antibodies described above, including fragments thereof. The kit may further comprise one or more epitopes or immunogens described above.

In a further embodiment, the diagnostic composition of the present invention may be in the form of an ELISA kit comprising one or more antibodies described above, including fragments thereof. The kit may further comprise one or more epitopes or immunogens described above.

In an additional embodiment, the diagnostic composition of the present invention may be in the form of an imaging reagent comprising one or more antibodies described above, including fragments thereof.

In a further embodiment, the diagnostic composition of the invention is a sandwich assay comprising a complex of two antibodies of the invention and an immunogen of the invention. The assay is used to detect the presence of the pathogenic tau dimers and pathogenic prefibrillar oligomeric tau.

Diagnostic Methods

In additional aspects of the invention, the invention is directed to methods of evaluating a mammal suspected of or having a tauopathy (e.g., AD), the method comprising (i) detecting binding of an antibody which selectively recognizes a pathogenic tau dimer and/or prefibrillar pathological or neurotoxic Tau to a component of a biological sample from the mammal, wherein the detection of pathogenic tau dimer and/or prefibrillar pathological or neurotoxic in the biological sample is indicative of tauopathy. The tauopathy can be Alzheimer's disease, Pick's disease (PiD), progressive supranuclear palsy (PSP), corticobasal degeneration (CBD), frontotemporal lobar degeneration (FTLD), or other disease condition that is associated with Tau oligomers. A biological sample includes, e.g., plasma, serum, cerebrospinal fluid (CSF), brain tissue, neuronal tissue, or muscle tissue. The detecting of the antibody is preferably done by an immunoassay.

The present invention relates to a method for the diagnosis of AD in a mammal, said method involving: determining the ratio of prefibrillar tau aggregates (including dimers and prefibrillar oligomers of tau) and total tau in a cerebrospinal fluid (CSF) sample from a mammal; and comparing the obtained ratio with the ratio of prefibrillar tau aggregates (including dimers and prefibrillar oligomers of tau) and total tau in a CSF sample from a control mammal (i.e., a mammal who does not have any tauopathies). Because mammals during early stages of AD (e.g., Braak Stage I) have increased ratios of prefibrillar tau aggregates (including dimers and prefibrillar oligomers of tau) to total tau, as compared to healthy mammals, the increased ratio would indicate that the mammal is suffering from an early stage of AD.

The ratio of prefibrillar tau aggregates (including dimers and prefibrillar oligomers of tau) and total tau can be detected in vitro as well as in vivo.

The method for the in vitro detection of the ratio of prefibrillar tau aggregates (including dimers and prefibrillar oligomers of tau) and total tau in a mammal comprises the steps of: obtaining a sample from said mammal; determining the ratio of prefibrillar tau aggregates (including dimers and prefibrillar oligomers of tau) and total tau, and comparing the obtained ratio with the ratio of prefibrillar tau aggregates (including dimers and prefibrillar oligomers of tau) and total tau in a sample from a control mammal (i.e., a mammal not suffering from any tauopathy). The sample may, e.g., be obtained from blood or CSF. In the preferred embodiments the sample is obtained from CSF of the mammal.

Total tau can be quantified by any method known, including but not limited to the use of antibodies or else by a functional assay (Bramblett et al., 1992). Any monoclonal or polyclonal antibody that specifically recognizes total tau may be used for the quantification of total tau. Antibodies recognizing aggregated and unagreegated Tau include, e.g., TauC3 antibody. Total tau quantification may also be determined by a commercially available tests (e.g., INNOTEST hTau-Ag (Innogenetics, Gent, Belgium). Prefibrillar tau aggregates can be quantified by, e.g., the use of the antibodies of the present invention (e.g., TOC1). In certain embodiments, prefibrillar tau aggregates are quantified by an immunoassay comprising an antibody of the present invention (e.g., TOC1), or a fragment thereof. Prefibrillar tau aggregates may also be quantified by a sandwich ELISA comprising the following steps: obtaining a sample from the patient; bringing said sample into contact with a monoclonal antibody (primary antibody or capturing antibody) selective recognizing prefibrillar tau aggregates (e.g., TOC1), under conditions being suitable for producing an antigen-antibody complex; bringing said sample into contact with a monoclonal antibody (secondary antibody or detector antibody) prefibrillar tau aggregates (e.g., TOC1), under conditions being suitable for producing an antigen-antibody complex; bringing the antigen-antibody complex into contact with a marker either for specific tagging or coupling with said secondary antibody, with said marker being any possible marker known to the person skilled in the art; possibly also, for standardization purposes, bringing the antibodies in contact with a purified immunogen or an epitope of the present invention, which were described above). In some of these embodiments, the secondary antibody itself can carry a marker or a group for direct or indirect coupling with a marker.

The method for the early in vivo detection of the ratio of prefibrillar tau aggregates (including dimers and prefibrillar oligomers of tau) and total tau in a mammal comprising quantifying the amounts of prefibrillar tau aggregates and tau in situ by non-invasive methods including but not limited to brain imaging methods described by Arbit et al. (1995), Tamada et al. (1995), Wakabayashi et al. (1995), Huang et al. (1996), Sandrock et al. (1996), Mariani et al. (1997), and calculating the ratio of prefibrillar tau aggregates and total tau. The quantification may be used e.g., by using TOC1 antibody to quantify prefibrillar tau aggregates and Tau12 antibody to quantify total tau. Because mammals during early stages of AD (e.g., Braak Stage I) have increased ratios of prefibrillar tau aggregates (including dimers and prefibrillar oligomers of tau) to total tau, as compared to healthy mammals, the increased ratio would indicate that the mammal is suffering from an early stage of AD.

In a further aspect, the invention is directed to a peptide which can be used for standardization in the diagnostic kits and methods of the invention. The peptide may comprise an immunogen or an epitope of the invention. The immunogens and epitopes of the invention were discussed above.

In an additional embodiment, the invention is directed to a composition comprising one or more antibodies described above and a cerebrospinal fluid of a mammal. In some of these embodiments, the composition comprises a soluble or insoluble complex of said antibody and a tau dimer or a tau oligomer.

Diagnostic Markers

In an additional aspect, the invention is directed to diagnostic markers of Alzheimer's disease.

In certain embodiments, a diagnostic marker comprises a quantitative ratio of TOC1 to His probe labeling of the respective oligomeric or filamentous structure. The ratio of TOC1 to His probe in healthy mammals is expected to be 0. The ratio of TOC1 to His probe of greater than 0 is indicative of the onset of AD (e.g., Braak stage I). The ratio is expected to increase with the disease's progression.

In additional embodiments, a diagnostic marker comprises a quantitative ratio of TOC1 to Tau 12. The ratio of TOC1 to Tau12 probe in healthy mammals is expected to be 0. The ratio of TOC1 to Tau12 of greater than 0 is indicative of the onset of AD (e.g., Braak stage I). The ratio is expected to increase with the disease's progression.

In certain embodiments, a diagnostic marker further comprises an antibody capable of selectively detecting tau which is cleaved by caspases at, e.g., Asp421 (e.g., TauC3 antibody). An appearance of cleaved Tau in the CSF of a patient is indicative that NFT(s) are about to form.

Technique for Crosslinking Tau

In an additional aspect, the invention is directed to techniques for crosslinking Tau.

One obstacle to studying Tau aggregation in vitro is that, unlike Aβ and α-synuclein, Tau does not aggregate spontaneously under physiological conditions (65). Anionic inducer molecules such as free fatty acids (e.g. AA) (66), heparin (67), or RNA (68) are required to induce Tau polymerization in vitro; however, the physiological inducer of Tau aggregation in situ remains unknown. Although prefibrillar Tau aggregates have been isolated from AD homogenates, the precise composition of these aggregates is unclear (26-28). Past attempts to characterize the earliest stages of Tau multimer formation in vitro were contingent upon disulfide bridge formation (26, 29). However, the formation of disulfide bridges can inhibit aggregation of Tau isoforms containing four microtubule binding repeats (MTBRs) (30-32), and aggregates of the four repeat isoforms are associated with many of the neurodegenerative tauopathies (33). These obstacles have been overcome by the methods described in the present application.

The invention in one aspect is directed to a technique for cross-linking Tau which does not depend upon disulfide bridges between cysteines of individual tau monomers. This technique has several advantages over techniques described elsewhere: (a) site-specific labeling of native cysteine residues, while Tau is in its soluble, extended conformation; (b) lack of interference with the Tau aggregation process; and (c) generation of stable, irreversible cross-linking of Tau multimers allowing for downstream applications such as aggregation and toxicity studies. In certain embodiments, the technique is a benzophenone cross-linking technique used in the present examples to generate Tau dimers.

The cross-linking technique may comprise reacting tau monomers with a molar excess of a cross-linker, aggregating the monomers to form an aggregate, and exposing the aggregates to a shortwave UV light. The linker may be an agent which has a sulfhydryl (SH) group and is capable of reacting with available cites upon UV illumination. The linker may, e.g., be selected from the group consisting of B4M, PEAS (N-((2-pyridyldithio)ethyl)-4-azidosalicylamide), succinimidyl trans-4-(maleimidylmethyl)cyclohexane-1-carboxylate (SMCC), 3-(2-pyridyldithio)propionate (SPDP), 2,5-Pyrrolidinedione, 1-[1-oxo-3-(2-pyridinyldithio)propoxy], succinimidyl acetylthioacetate (SATA), N-((2-pyridyldithio)ethyl)-4-azidosalicylamide), or the like. In the preferred embodiments, the linker is B4M.

In the preferred embodiments, the cross-linker is B4M, a 10-fold molar excess of B4M is used, the monomers are aggregated in the presence of arrachidonic acid, and are cross-linked with UV light (254 mm).

The cross-linking technique may also comprise reacting a tau monomer (e.g. hTau40) with benzophenone-4-maleimide (B4M). B4M preferably reacts with one or more cysteine residues of the tau monomer. The reaction is preferably conducted before the tau monomer is aggregated.

These cross-linking techniques, and the technique, utilized in the examples below do not rely upon oxidative conditions.

DETAILED DESCRIPTION OF PREFERRED EMBODIMENTS

Example 1

Tau proteins are numbered according to the largest isoform found in the central nervous system (hTau40), which consists of 441 amino acids and contains both alternatively spliced N-terminal exons and four microtubule biding repeats ("MT-BRs"). HTau40 was used for all experiments except where otherwise indicated.

Recombinant Tau Protein Expression and Purification

The Tau MTBR construct consisting of residues 244-372 was generated by creating a linear PCR product of this region. An EcoRI restriction site and methionine residue were added N-terminal to residue 244 as well as a poly-His tag and NotI restriction site C-terminal to residue 372. The linear PCR product was inserted into the pET-17b vector (Novagen) via EcoRI/NotI digestion followed by T4 ligation. All other Tau constructs were cloned into vector pT7c as described elsewhere (34-37, 86). Tau constructs were expressed in *Escherichia coli* and purified using TALON metal affinity resin (Clontech) followed by size exclusion chromatography, as previously described (36, 38).

In Vitro Aggregation

Tau-Aggregation was induced with arachidonic acid ("AA"), as previously described (39). Briefly, Tau proteins (2-16 µM) were incubated at room temperature or at 37° C. for deletion mutants. Aggregation assays were performed in a solution containing 50 mM HEPES, pH 7.6, 50 mM KCl, and 5 mM DTT (unless otherwise indicated) in the presence of 37.5-150 µM peroxidase-free AA (Cayman Chemical). Working solutions of AA were prepared in 100% ethanol immediately prior to use.

α-Synuclein-Untagged recombinant full-length human α-synuclein was prepared and aggregated as previously described (40). Briefly, a-synuclein (4 µM) as incubated at 37° C. in 10 mM HEPES, pH 7.6, 100 mM NaCl, and 5 mM DTT in the presence of 200 µM AA for 24 hours.

Aβ-Recombinant human Aβ42 (rPeptide) HFIP (1,1,1,3,3,3-hexafluoro-2-propanol)-treated stocks were prepared as previously described (41). Aβ42 oligomers and filaments were generated according to established protocols (41) with the exception that 4 mM HEPES, pH 8.0, was substituted for Ham's F-12 media. In all cases, aggregation was confirmed using trans-mission electron microscopy (EM). Samples were fixed with 2-10% glutaraldehyde, spotted on formvar/carbon-coated copper grids (Electron Microscopy Sciences), and stained with 2% uranyl acetate.

Benzophenone Cross-Linking hTau40 (15 µM) was reacted with a 10-fold molar excess of benzophenone-4-maleimide (B4M) cross-linker (Invitrogen) in the dark for 4 hours in 100 mM Tris, pH 7.4, 0.1 mM EGTA, and 0.5 mM Tris(2-carboxyethyl)phosphine hydrochloride. The reaction was quenched with 5 mM DTT and excess B4M was removed using Nanosep centrifugal filter devices (Pall; MWCO 30 kDa). B4M-labeled Tau (8 µM) was aggregated overnight in 100 mM Tris, pH 7.4, 0.1 mM EGTA, and 5 mM DTT in the presence of AA as described above. Cross-linking was induced with shortwave UV light (254 nm) for 5 minutes unless otherwise indicated. For sedimentation analysis, samples were centrifuged in a TLS-55 Beckman rotor over a 40% glycerol cushion at 269,000×g for 30 min at 25°. The supernatant was collected and the pellet was resuspended in 100 mM Tris, pH 7.4.

Electroelution

Cross-linked hTau40 aggregates were concentrated by sedimentation (as described above), diluted in Laemmli buffer, heated in a boiling water bath for 10 minutes, and separated by SDS-PAGE using 4-8% linear gradient polyacrylamide gels. Gels were stained with the E-Zinc Reversible Stain Kit (Thermo Scientific) according to the manufacturer's instructions. Individual bands were isolated and placed inside D-Tube Dialyzers (MWCO 6-8 kDa, Novagen). Samples were electroeluted for 5 hours at 150 V in 25 mM Tris, 192 mM glycine, and 0.025% SDS. Electroeluted proteins were concentrated to about 50 µl volume with Pall Nanosep centrifugal concentrators prior to incubation in 400 µl of SDS-away (Protea Biosciences) overnight at −20° C. to precipitate the proteins. Samples were centrifuged at 18,000×g for 10 min at 4° C., the pellets were resuspended in 400 µl of SDS-away, recentrifuged, and finally resuspended in 50 mM HEPES, pH 7.6, 50 mM KCl, 0.01% Triton X-100. Samples were boiled for 5 minutes and centrifuged at 16,000×g for 1 min to remove insoluble proteins.

Mass Spectrometry Analysis

Figure 11:
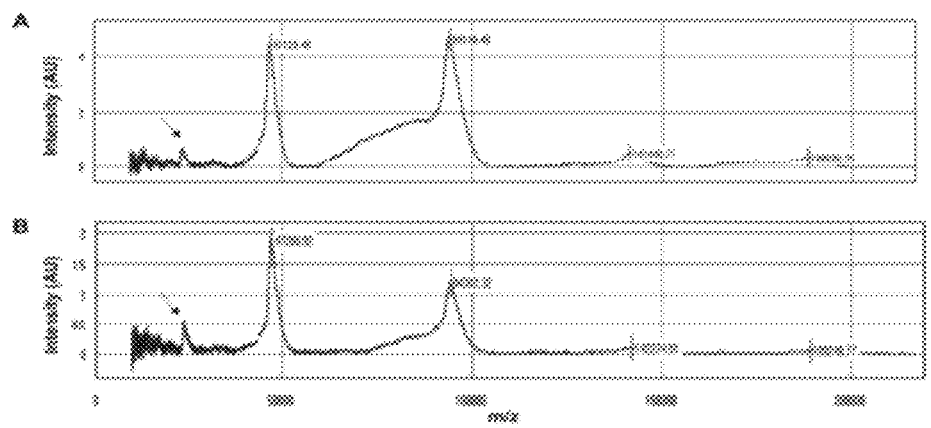
FIGS. 11A and 11B depict Tau dimers incorporating into larger aggregated species.

Protein samples were subjected to analysis by surface enhanced laser desorption and ionization time of flight (SELDI-TOF) mass spectrometry to examine the distribution of masses of protein components. Samples were spotted in three successive 5 µl aliquots onto individual spots of a ProteinChip NP20 Array (Bio-Rad) and allowed to partially air dry for about 10 minutes to reduce the volume between applications. The chip was then washed three times with 5 µl of distilled water and air-dried prior to the addition of 2.5 µl of 10 mg/ml sinapinic acid (Bio-Rad) in 60% acetonitrile, 0.1% formic acid. Controls omitting the air drying for multiple applications of the sample as well as omitting the formic acid with matrix crystallization indicated no difference in the distribution of multimers (FIG. 11). Samples were analyzed using a Bio-Rad ProteinChip System 4000 Enterprise mass spectrometer and calibrated against the Bio-Rad All-in-1-Protein Standard. Each spot was divided into 10 partitions with 210 shots/partition and the data were collected at a laser energy of 3000 joule with a mass range between 10 and 160 kDa unless otherwise indicated.

Tau Oligomeric Complex-1 (TOC1) Antibody Generation

Mouse monoclonal antibodies were raised against electro eluted cross-linked Tau dimers. Female Tau null mice (The Jackson Laboratory; stock number 7251) were immunized subcutaneously five times with 2-10 µg of cross-linked Tau dimer. For the final two immunizations, 100 µg of cross-linked Tau oligomers (hTau40 incubated in the presence of AA for 15 minutes, cross-linked, and flash frozen) was administered. Once the desired serum titer was attained, splenocytes were isolated and fused to SP2/o myeloma cells (42). Two weeks after hybridoma selection in hypoxanthine/aminopterin/thymidine medium, positive clones were chosen based on their ability to bind Tau oligomers but not Tau monomer. One cell line, TOC1, was subcloned two times to ensure monoclonality and hybridoma stability. The clone was adapted to serum-free medium, grown in a CELLine CL 1000 Bioreactor (Sartorius), and the antibody purified by size exclusion chromatography prior to storage in HEPES-saline buffer, pH 7.4, containing 50% glycerol. Isotyping indicated that TOC1 was of the IgM isotype.

Human Brain Homogenates

Frozen frontal cortex samples from control (Braak I-III) and AD brains (Braak V-VI) were obtained from Rush University Medical Center or the University of Miami Medical Center. Samples were homogenized as previously described (43). For denaturing conditions, homogenates were diluted in 2x Laemmli buffer, heated in boiling water for 5 minutes, and briefly centri-fuged at 8,000xg for 3 minutes to remove cellular debris prior to collection of the supernatant. For nondenaturing conditions, homogenates were briefly centrifuged at 3,000xg for 10 minutes.

Immunoblots

Recombinant Tau and human brain homogenate samples were separated by SDS-PAGE on 4-15% linear gradient gels and transferred to nitrocellulose membranes as described previously (43). For dot blots, samples were spotted directly onto nitrocellulose membranes (44). Both Western and dot blot membranes were blocked with 5% nonfat dry milk in TBS, pH 7.4, and incubated in primary antibodies overnight at 4° C. For dot blots, 0.05% Triton X-100 was added to the TBS solution. The Tau12 (45), TauS (46), Tau7 (47), MOAB-2 (a mouse monoclonal antibody (IgG1) produced in the Binder laboratory what recognizes Aβ40 and –42), and TOC1 mouse monoclonal antibodies were used at 0.0067, 0.01, 0.04, 0.05, and 0.1 µg/ml, respectively. The mouse monoclonal anti-α-synuclein (Chemicon; MAB5320) and rabbit monoclonal anti-β-actin (Cell Signaling Technology; clone 13E5) antibodies were diluted to 1:2000 and 1:1000, respectively. The rabbit polyclonal antibodies R1 (48) and His-probe (Santa Cruz Biotechnology; clone H-15) were used at 0.0075 and 0.5 µg/ml, respectively. After rinsing, the membranes were incubated in peroxidase-conjugated horse anti-mouse secondary antibody (Vector Labs) or peroxidase-conjugated goat anti-rabbit (Vector Labs) secondary antibody for 1 hour at room temperature. Reactivity was visualized using ECL substrate (Pierce). Dot blots were quantified using Image) software (National Institutes of Health) and expressed as the ratio of TOC1:Tau12 or TOC1:H is probe intensity.

Immunogold Labeling of Recombinant Tau Aggregates

Aggregated Tau samples were spotted onto 300-mesh formvar/carbon-coated nickel grids (Electron Microscopy Sciences), blocked with 0.1% gelatin, 5% goat serum in TBS, and incubated with the H is probe (Santa Cruz; 10 µg/ml) or TOC1 (50 µg/ml) primary antibodies in 5% goat serum/TBS. Grids were then rinsed with TBS prior to incubation with 10-nm diameter gold-conjugated anti-rabbit IgG (Sigma) or anti-mouse IgM (Electron Microscopy Sciences) secondary antibodies diluted 1:20 in 5% goat serum/TBS. Finally, grids were rinsed with X10 TBS to reduce nonspecific labeling, rinsed with water, and stained with 2% uranyl acetate. Samples were not fixed with glutaraldehyde because this obscured the TOC1 epitope. Optimas 6.0 imaging software (Media Cybernetics) was used to identify and measure oligomers (defined as objects <50 nm in length) and filaments (defined as structures >50 nm in length) and individual gold particles were tallied. To control for differences in the relative quantities of oligomers and filaments present in a given Tau aggregation reaction, results were expressed as the ratio of TOC1:His tag labeling of the respective oligomeric or filamentous structures. Three fields from each grid were chosen for quantitation.

Immunohistochemistry

Tissue sections (40 µm) of control (Braak stages I and II) and severe AD (Braak stages V and VI) cases from the entorhinal cortex (n=4), hippocampus (n=3; AD only), and superior temporal gyrus (n=2) were obtained from the Cognitive Neurology and Alzheimer's Disease Center at Northwestern University. Tissue sections were processed as previously described (49). The TOC1 antibody (0.05 µg/ml) was incubated with tissue sections overnight at 4° C. The tissue was incubated in biotinylated goat anti-mouse secondary antibody (Vector; diluted 1:500) for 2 hours followed by incubation in ABC solution (Vector; according to the manufacturer's instructions) for 1 hour. The staining was developed with 3,3'-diaminobenzidine (Sigma). Sections were mounted onto glass slides, dehydrated through graded alcohols, cleared in xylenes, and coverslipped with Permaslip (Alban Scientific).

Immunofluorescence

Tissue sections (as described above) from the entorhinal cortex of control (Braak stages I and II; n=2) and severe AD (Braak stages V and VI; n=2) cases were processed for immunofluorescence using methods similar to those previously described (50). Briefly, sections were incubated with TOC1 (0.2 µg/ml), the rabbit monoclonal antibody pS422 (Epitomics; diluted 1:2500), and/or MN423 (0.5 µg/ml) (51) overnight at 4° C. After washing with PBS containing 0.04% Triton X-100, sections were incubated in Alexa Fluor 488 goat anti-mouse IgM µ chain-specific (Invitrogen, diluted 1:500), Alexa Fluor 594 goat anti-rabbit IgG (Invitrogen, diluted 1:500), and/or Alexa Fluor 594 goat anti-mouse IgG2b (Invitrogen, diluted 1:500) secondary antibodies for 2 hours at room temperature. Sections were counterstained with Thiazin Red (0.004%) as indicated. Tissue sections were rinsed in PBS/Triton X-100, mounted onto glass slides, incubated with Sudan Black (0.05%) to eliminate lipofuscin autofluorescence, and coverslipped using Vectashield mounting medium (Vector). Staining was visualized using a LSM 510 Meta (Zeiss) laser scanning confocal microscope. All confocal images were acquired as z-stacks of single optical sections and analyzed using Zeiss LSM Image Viewer.

Statistics

SigmaStat software (Systat Software, Inc.) was used for all statistical tests. Comparisons were made using at test or one-way analysis of variance followed by Student-Newman-Keuls post hoc analysis as indicated. Data were expressed as mean±S.E. and significance was set at p values as noted.

Results a. Cross-Linking of the Longest Isoform of Tau (hTau40) Reveals an Apparent 180-kDa Oligomer An established photochemical cross-linking method to examine intermolecular interactions of full-length Tau in vitro (52) (FIG. 1A) was employed. The B4M cross-linker is distinctive in that one end reacts with native cysteine residues and the other end is UV-photoactivatable. Thus, B4M can be used to label the cysteine residues prior to aggregation and, then, UV light can induce cross-linking of carbon-hydrogen bonds within 9Å after the assembly reaction is complete (52). This substantially differs from previous work in which the cysteine residues are cross-linked and, then, Tau was polymerized into filamentous aggregates (26). In addition, using B4M eliminates accessibility issues that may arise when Tau is aggregated prior to cross-linking. B4M cross-linking did not affect the ability of Tau to aggregate (FIGS. 1, B and C), allowing for the stabilization of Tau in its aggregation-competent conformation.

Figure 10:
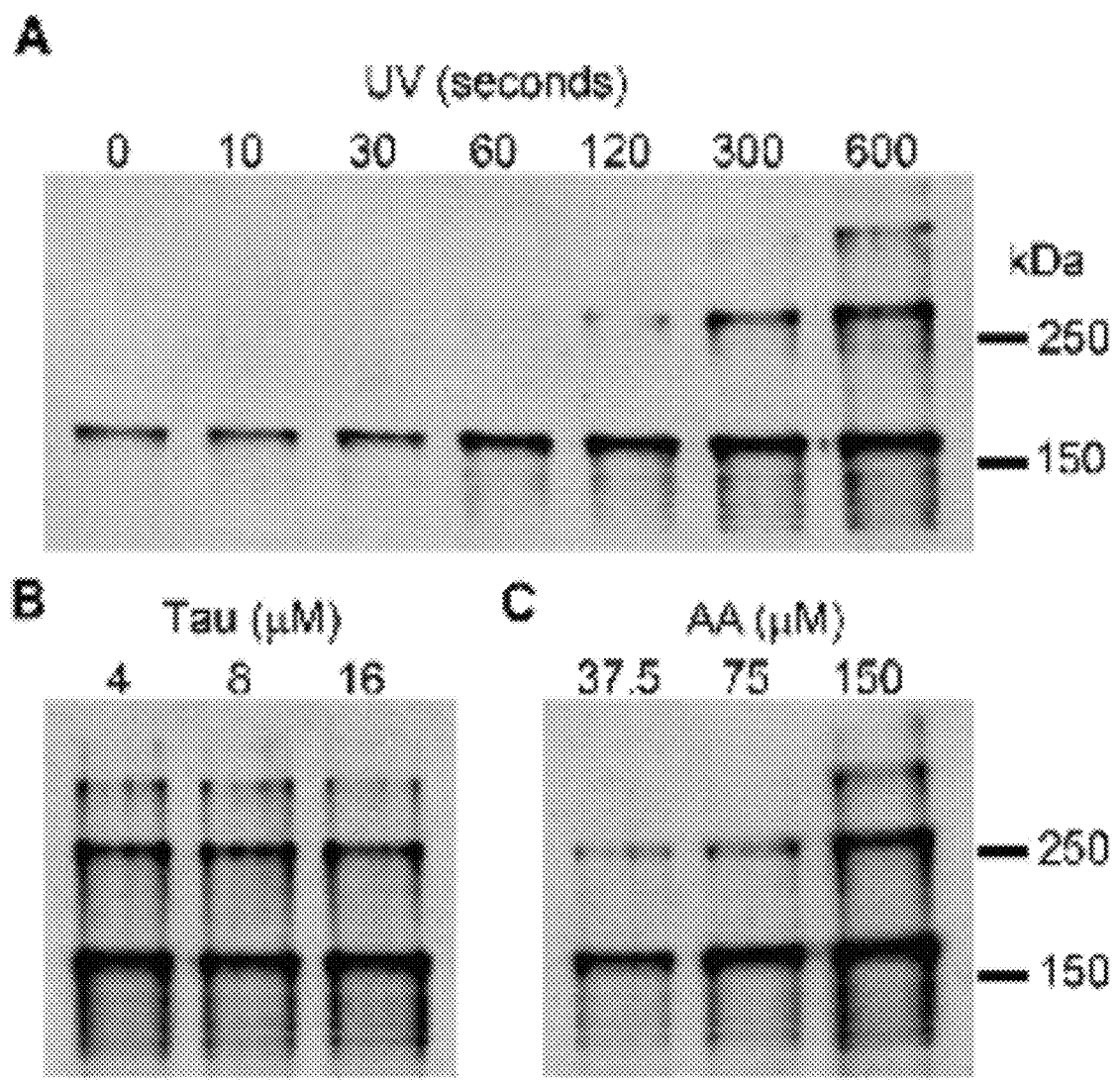
FIGS. 10A-10C depict SELDI-MS analysis of cross-linked apparent 180 kDa multimer reveals predominantly dimeric tau with little trimeric or tetrameric contamination and effects of UV irradiation time, tau concentration, and AA concentration on oligomer formation.

Treatment with an anionic inducing agent such as AA revealed sharp bands at apparent molecular masses of 180 kDa and higher when analyzed by SDS-PAGE (FIG. 1D). As monomeric hTau40 (actual molecular mass 47 kDa) migrates at 60 kDa on SDS-PAGE, this cross-linked product exhibited the apparent mass of a trimer. Importantly, only a small amount of this species was present in the absence of inducer. Moreover, background levels of the 180-kDa species were observed in the absence of cross-linker indicating that this oligomeric species is somewhat SDS stable. To ensure that the results were not an artifact of the reaction conditions, the UV irradiation time, Tau concentration, and AA concentration were varied (FIG. 10). Under all conditions tested, the 180-kDa multimer was the predominant cross-linked species.

b. The 180-kDa Oligomeric Species is Found in AD but not Controls

Figure 2:
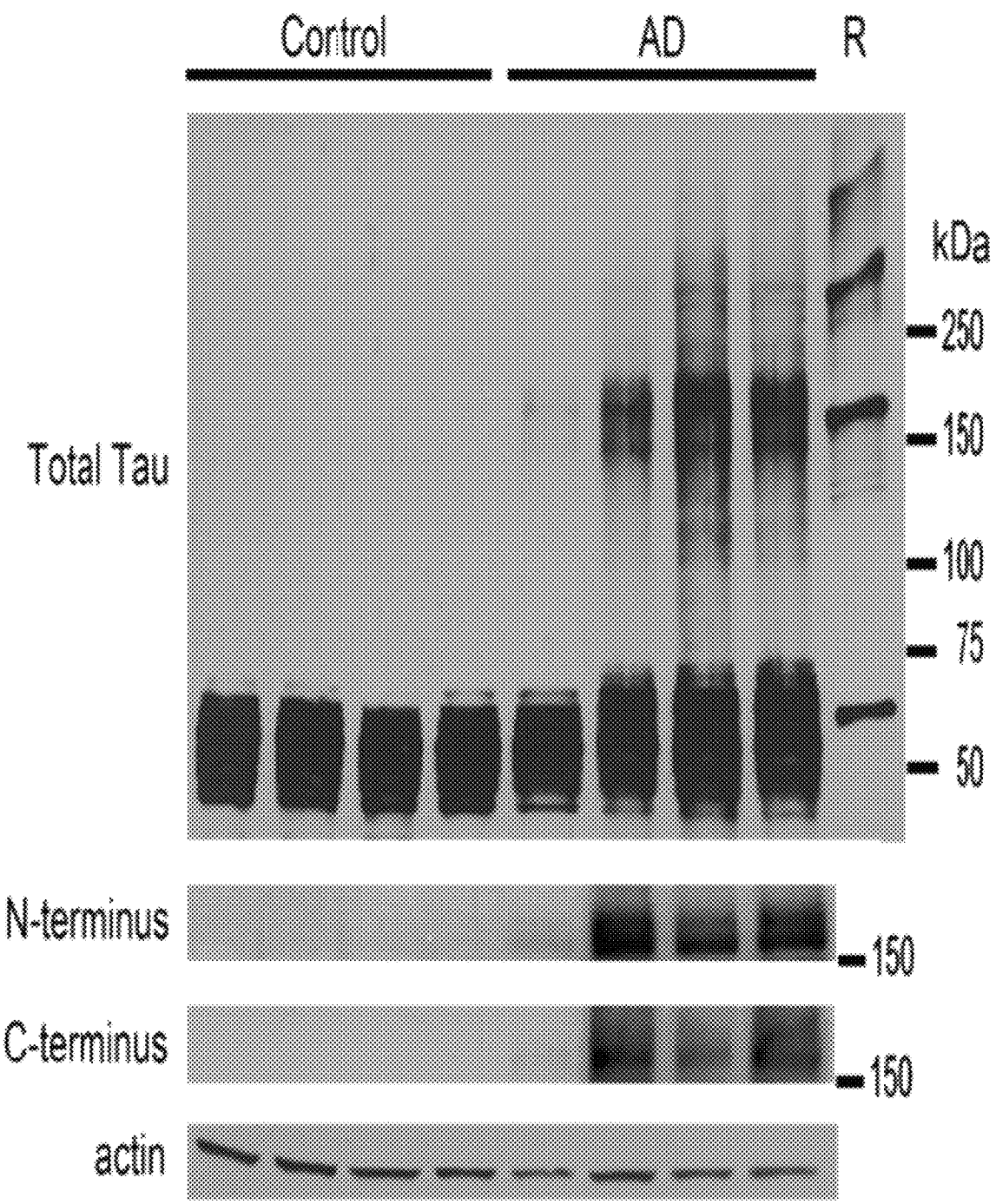
FIG. 2 depicts an apparent 180-kDa Tau oligomer found in brain homogenates of Alzheimer disease patients (Braak V and VI) but not in controls (Braak Whole homogenates (35 μg/lane) of frontal cortices obtained from 4 control and 4 AD brains were analyzed for the multimeric Tau species by Western blotting using polyclonal Tau antibody R1 (total Tau). Recombinant B4M cross-linked hTau40 (R) was run in parallel. In AD cases, multimeric Tau aggregates migrate at a similar M, to cross-linked recombinant Tau indicating that these aggregated species may be comparable in nature. Multimeric Tau aggregates were not observed in control cases. Additionally, the 180-kDa multimeric Tau aggregate was visible in AD cases when probed with Tau12 (N-terminus antibody) and Tau7 (C-terminus antibody), indicating that this species is not an amalgam of cleavage products of Tau monomers. Actin was used as a loading control.

Frontal cortex homogenates from severe AD (Braak V and VI; n=4) and control cases with no cognitive impairment (Braak I-III; n=4) were analyzed for the presence of SDS-stable Tau oligomeric aggregates. Interestingly, the 180-kDa species were found in all four AD cases examined but not the control cases (FIG. 2). Given that cleavage of Tau occurs in AD (53-55), the homogenates for intact Tau using anti-bodies to the extreme N and C termini (Tau12 and Tau7, respectively) were produced. It was found that the 180-kDa aggregates possessed both termini and likely were not composed of cleavage products. When cross-linked recombinant Tau aggregates were run in parallel, the 180-kDa aggregates from brain and recombinant Tau samples appeared to migrate similarly (FIG. 2). This data demonstrate, e.g., that SDS-stable Tau oligomers are disease specific and that the in vitro cross-linking method stabilizes Tau aggregates of comparable size.

c. The 180-kDa Cross-Linked Species is a Dimer

Figure 3:
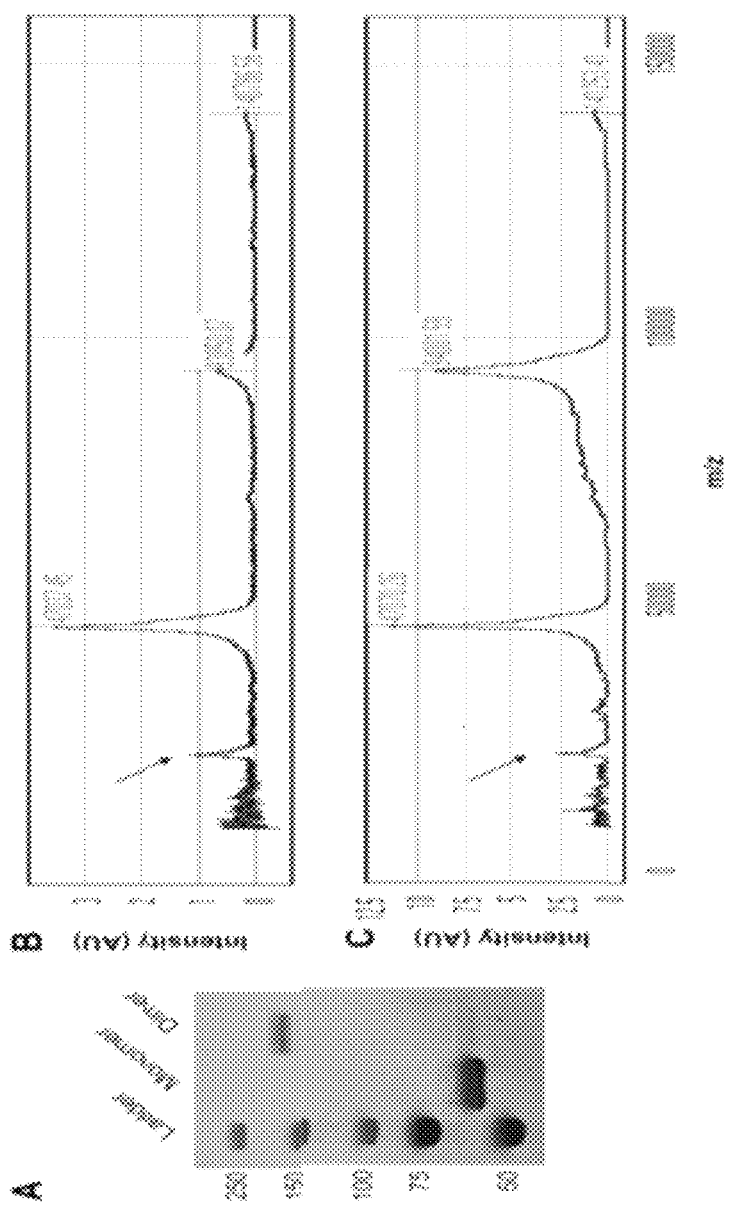
FIGS. 3A-3C depict SELDI-TOF MS analysis revealing that apparent 180-kDa Tau oligomer is predominantly a dimer.

Cross-linked recombinant Tau aggregates were sedimented to remove residual unaggregated Tau, dissociated with 2% SDS, and separated by SDS-PAGE. Monomeric Tau (60 kDa on SDS-PAGE) and the 180-kDa cross-linked product were purified via electroelution. During purification of the 180-kDa cross-linked species, it was subjected to harsh denaturing conditions using SDS to dissociate noncovalent interactions. After purification, the 180-kDa product was analyzed via SDS-PAGE to verify that it still migrated at the same molecular mass (FIG. 3A). Variable amounts of monomeric Tau were co-eluted with the 180-kDa band, signifying that not all of the apparent 180-kDa products were cross-linked. Attempts to purify significant quantities of larger cross-linked species were unsuccessful.

Figure 12:
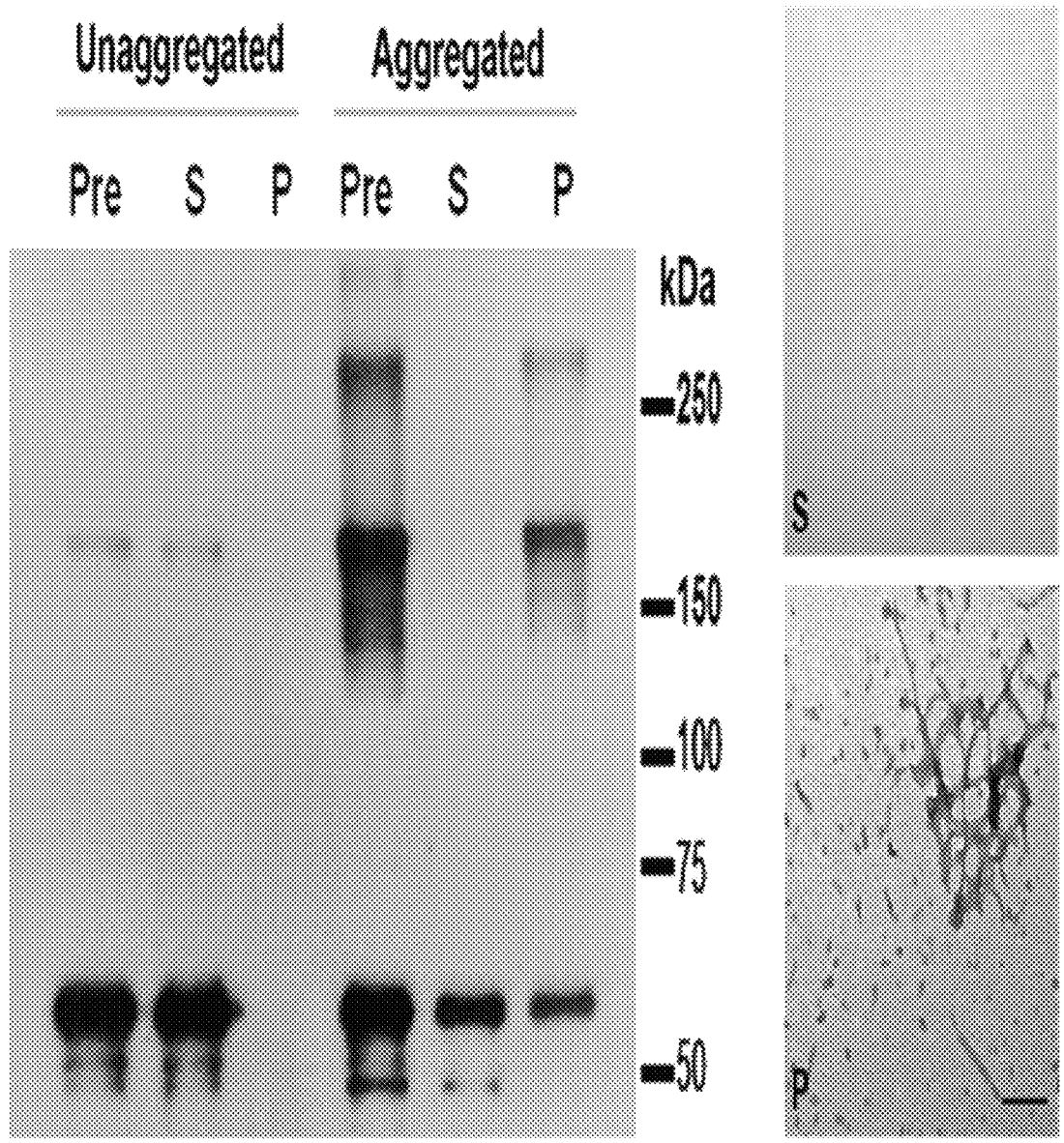
FIG. 12 depicts Effect of UV irradiation time, tau concentration, and AA concentration on oligomer formation. Unaggregated tau (−AA) and tau aggregated with AA were cross-linked with B4M and subsequently sedimented to separate aggregates from residual monomer. Western blot analysis demonstrated that tau dimers are found in the supernatant of the unaggregated sample. However, when AA was added, the cross-linked products were observed in the pellet fraction. This indicates that dimers are likely intermediate species in the formation of higher order aggregates. EM of the supernatant and pellet of an aggregated tau reaction demonstrated that both oligomers and filaments sedimented. Pre, prespin; S, supernatant; P, pellet. Scale bar is 200 nm.
Figure 13:
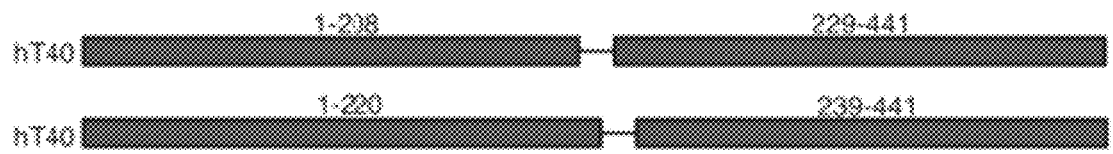
FIG. 13 depicts Tau deletion constructs used to determine the TOC1 epitope in Example 2.
Figure 14:
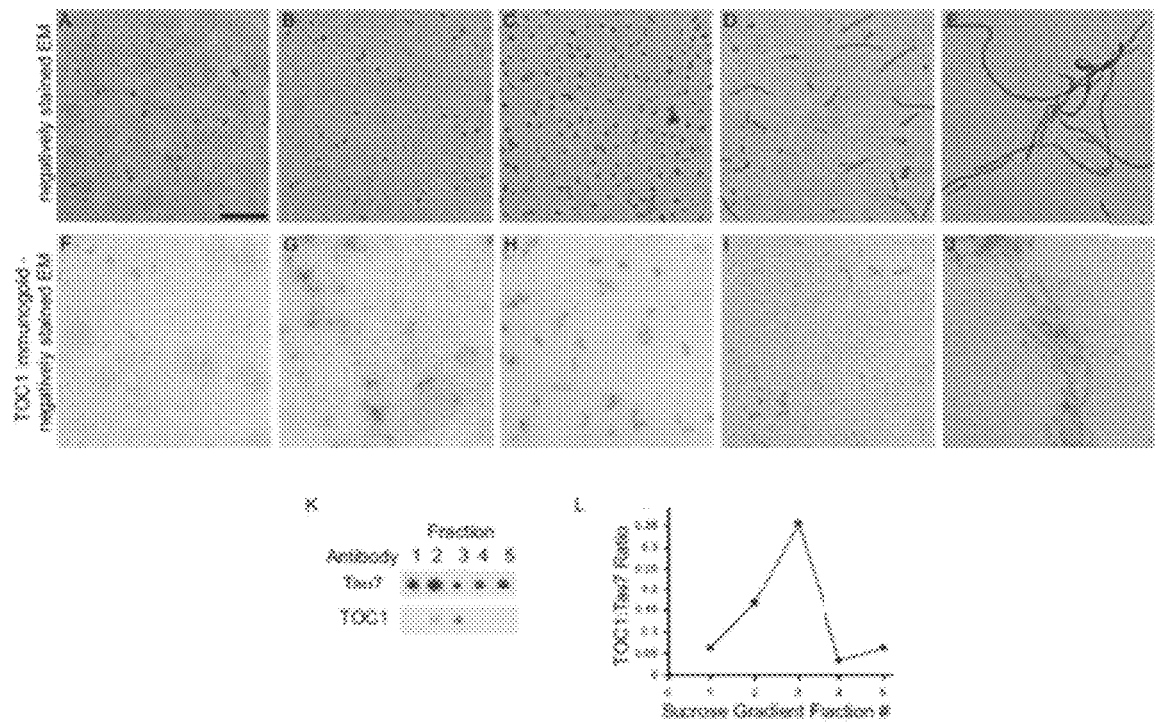
FIG. 14A-14L depict TOC1 preferentially labeling tau oligomers (Fraction 3) purified through sucrose gradient density fractionation of Example 3.
Figure 15:
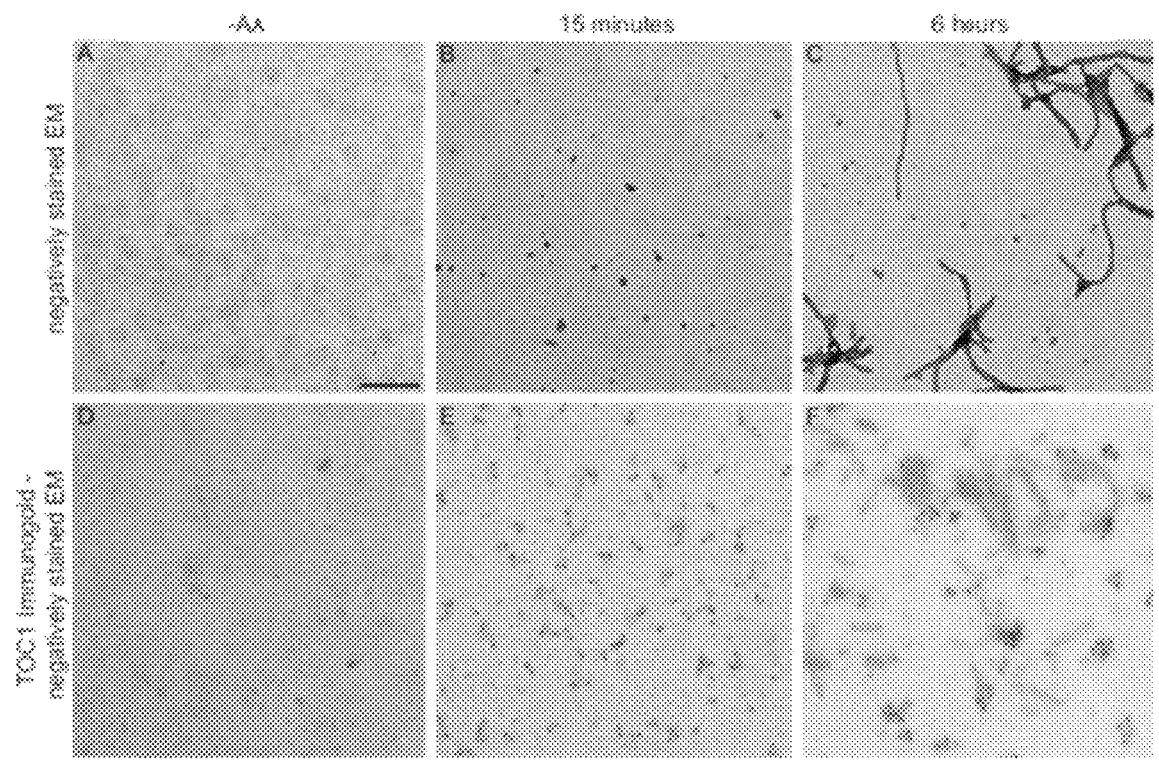
FIG. 15A-15F depict TOC1 preferentially labeling tau oligomers tau over filaments or unaggregated tau of Example 5.

SELDI-TOF MS of the electroeluted monomer revealed a prominent peak at 47 kDa as predicted (FIG. 3B). Smaller peaks at 94 and 141 kDa corresponding to dimeric and trimeric Tau species were also observed. In contrast, SELDI-TOF analysis of the purified apparent 180-kDa species revealed a prominent Tau dimer peak at 94 kDa in addition to the 47-kDa peak representing uncross-linked monomer (FIG. 3C). Minor trimer (141 kDa) and tetramer (188 kDa) peaks were also observed (FIG. 12). It is improbable that the dimeric Tau identified here was a breakdown product of the purified apparent 180-kDa cross-linked product because, if that was the case, another band that migrates at a molecular mass between the monomeric and 180-kDa species on SDS-PAGE would have been seen. The band that migrates at a molecular mass between the monomeric and 180-kDa species on SDS-PAGE was not seen in the present experiment. Thus, the cross-linked product is a dimer that migrates anomalously when analyzed by SDS-PAGE, most likely due to the anisotropy of these stable multimers.

d. Tau Dimers Aggregate to Form Oligomers but not Long Filaments

Cross-linked Tau aggregates were sedimented to confirm that these species incorporate into larger aggregates. In the absence of inducer, the small amount of dimer present was found only in the supernatant (FIG. 12). In the presence of AA, all of the cross-linked species sediment indicating that they incorporate into larger Tau aggregates. This revealed that dimers are intermediates in at least some form of Tau aggregation, as they are observed in the supernatant without inducer and the pellet after AA is added.

Figure 4:
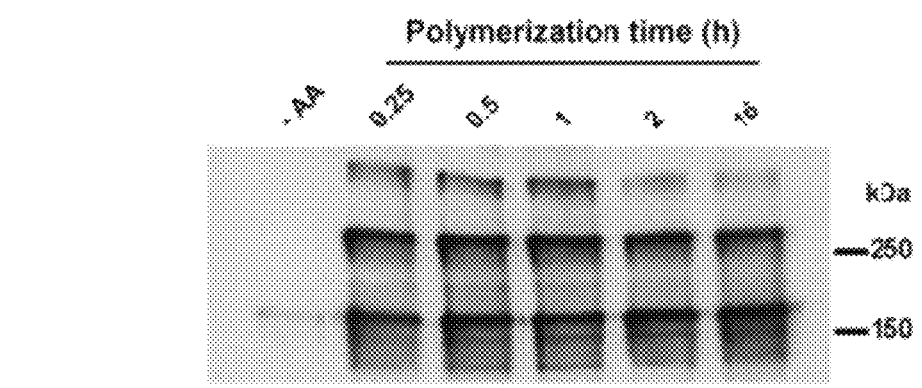
FIGS. 4A and 4B depict Tau dimers associated to form oligomers but not long filaments.
Figure 4:
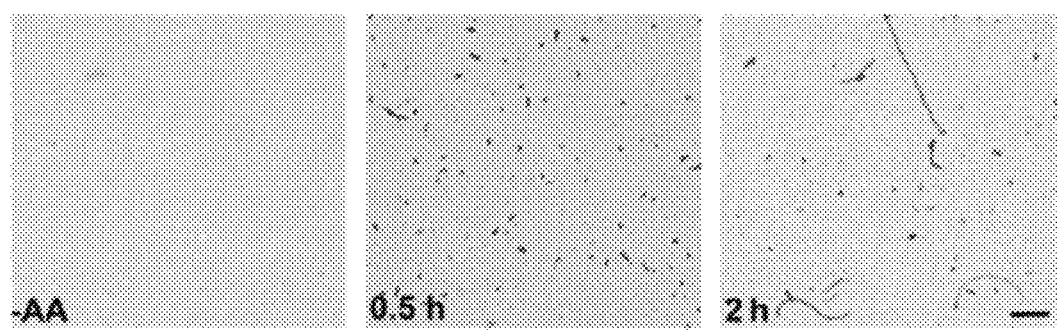
Figure 4:
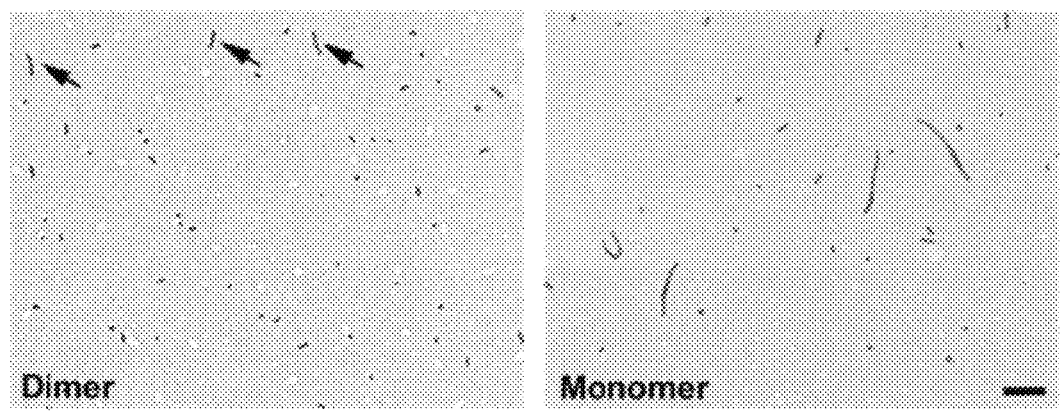

Time course experiments were performed to determine when dimer formation occurs. Tau dimerization reached peak levels 15 minutes after the addition of AA (FIG. 4A). Interestingly, only oligomers and the occasional short filament but no long filaments were observed at the earliest time points. Filament length steadily increased over the next several hours; however, a concomitant increase in dimerization was not observed. This indicates that dimerization is an early event that precedes filament formation in vitro.

Figure 5:
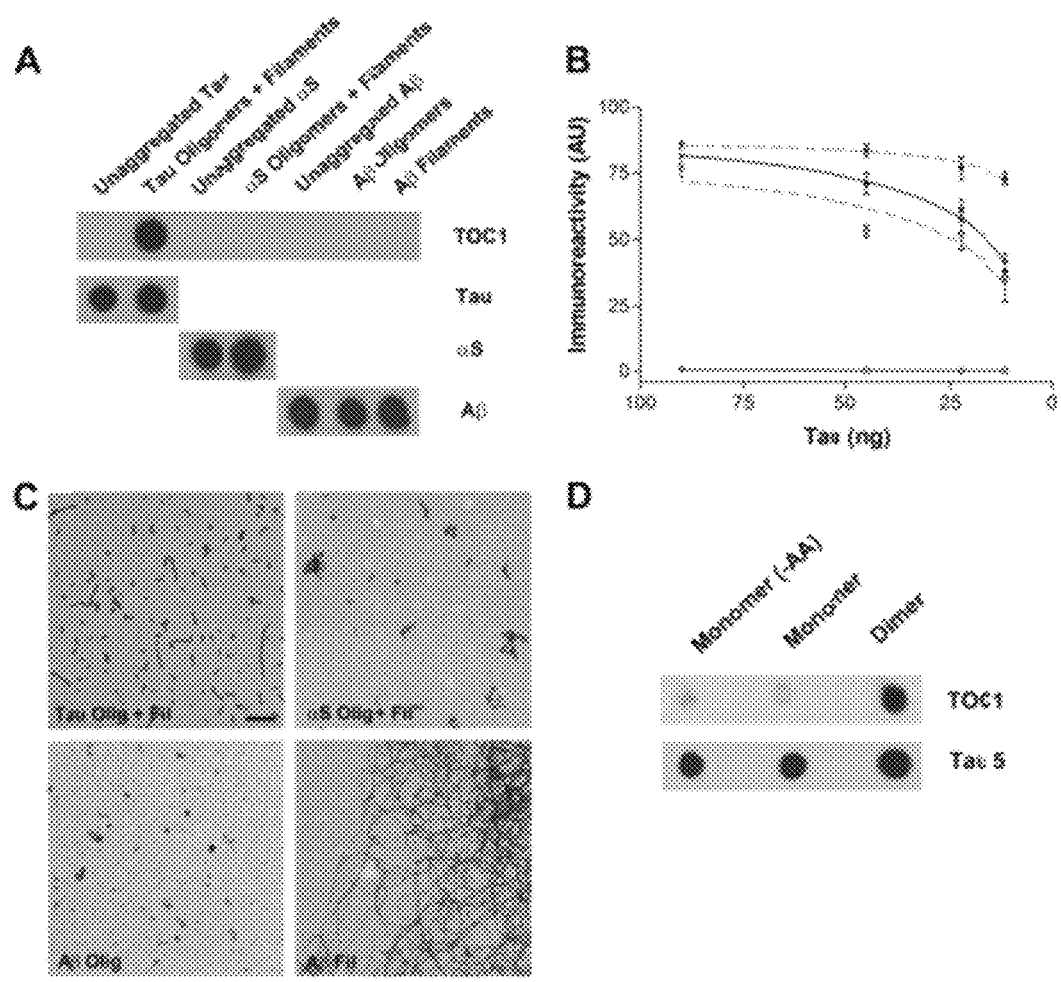
FIGS. 5A-5D depict characterization of the TOC1 monoclonal antibody.

To further ascertain the role of dimer formation, purified cross-linked Tau dimers were aggregated in the presence of AA (FIG. 4B). Similar to the early time points, mostly oligomeric aggregates were visible in the EM, even 24 hours after the addition of inducer. In contrast, assembly of electroeluted monomeric Tau resulted in the formation of oligomers and long filaments. Little aggregation of either monomeric or dimeric Tau was observed in the absence of AA. Thus, it appears that Tau dimerization is a prenucleation event, as AA is required for aggregation. It is possible that the oligomers composed of Tau dimers are "off-pathway" aggregates that do not incorporate into filaments; however, in the aggregated dimer preparations, a few short filaments were observed in addition to the oligomeric aggregates (FIG. 4B), suggesting that aggregated dimers can form filaments but that filament elongation likely favors a different mechanism of addition to the ends of the Tau polymer.

e. Tau Oligomeric Complex-1 (TOC1) Monoclonal Antibody Selectively Recognizes Tau Oligomers Previous work demonstrated the existence of Tau oligomers in AD brain homogenates (25, 56); however, the role of these oligomers in disease remains controversial. A novel mouse monoclonal antibody, TOC1, against purified recombinant cross-linked Tau dimers, was raised, e.g., to confirm that Tau dimers and/or higher order oligomeric species exist in AD. The selectivity of TOC1 for aggregated Tau over unaggregated Tau was confirmed using dot blots (FIGS. 5, A and B). Importantly, when operating at saturating levels of anti-body-immunogen binding, TOC1 showed no reactivity toward unaggregated Tau. In contrast, Tau 12 reacted with both unaggregated and aggregated Tau. Furthermore, TOC1 failed to react with either $\alpha$-synuclein or A$\beta$ in the unaggregated, oligomeric, or filamentous states (FIG. 5A).

Next, the reactivity of TOC1 against purified cross-linked dimers was accessed. When probed using dot blots, TOC1 preferentially labeled cross-linked dimers over electroeluted B4M-labeled monomeric Tau isolated from the same aggregation reaction (FIG. 5D). These data indicated that the exposure to AA alone did not confer the TOC1 epitope and that a minimum of two Tau molecules was required to form the epitope.

Figure 6:
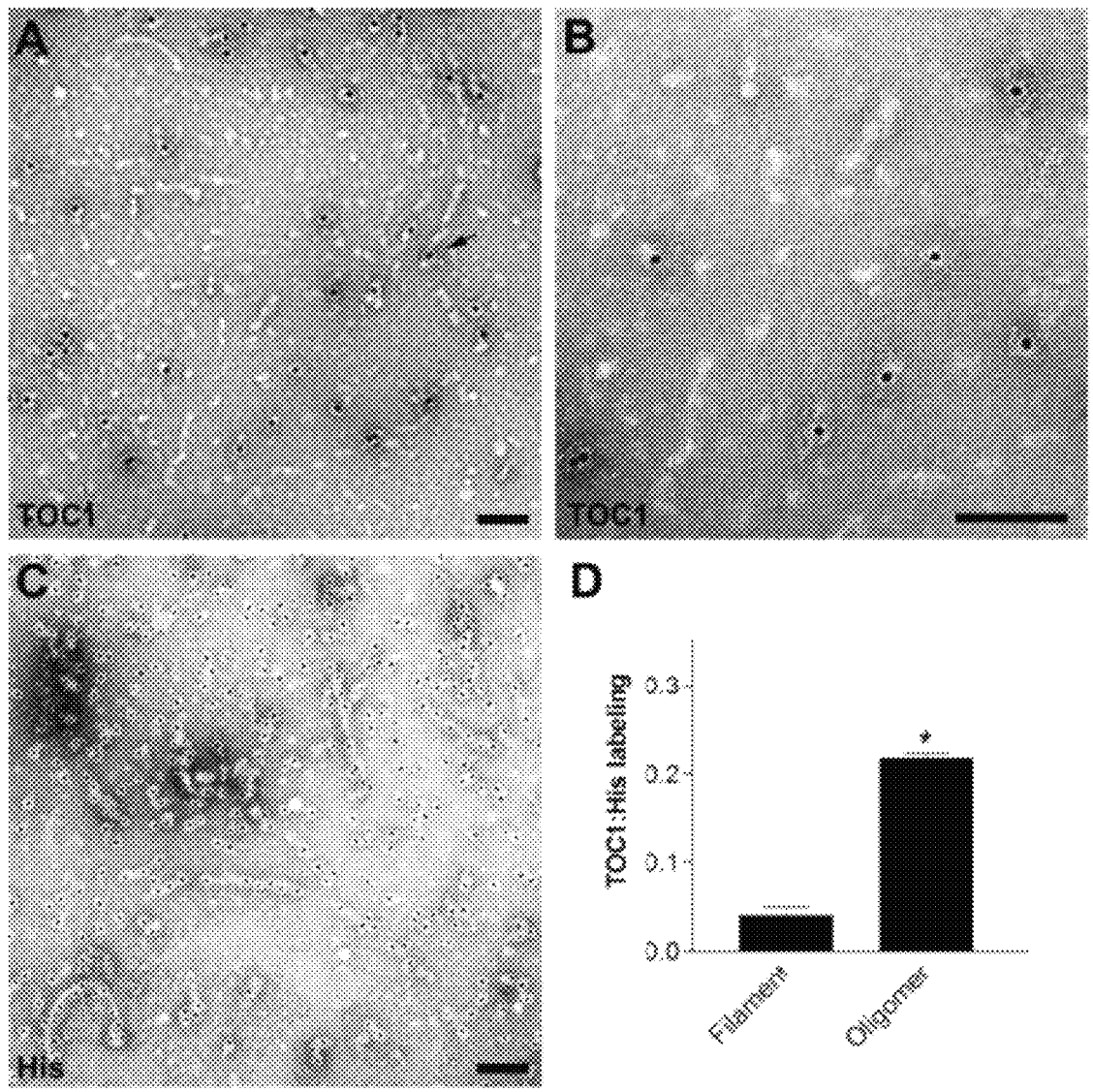
FIGS. 6A-6D depict TOC1 preferentially labeling Tau oligomers (i.e., apparent 180-kDa Tau oligomers).

To further clarify which aggregated species of Tau was recognized by TOC1, immunogold labeling of Tau aggregate preparations was used. Qualitative analyses of the electron micrographs revealed that TOC1 preferentially (i.e., selectively) detected Tau oligomers over filaments; however, occasional labeling of the ends of filaments was observed (FIG. 6A). To control for concentration differences between oligomeric and filamentous aggregates, TOC1 immunogold labeling results were compared with immunogold labeling of the poly-His tag in the same aggregate preparation (FIG. 6C). TOC1 was over seven times more likely to label oligomers (structures <50 nm in length) than filaments (structures >50 nm in length). Collectively, this data established that TOC1 is selective for Tau dimers and higher order oligomers but does not effectively label Tau monomers or filaments. Interestingly, TOC1 appears to label only a subpopulation of the oligomeric aggregates suggesting that more than one Tau oligomer conformation may exist.

f. TOC1 Recognizes a Conformational Epitope of Tau

The affinity data verifies that non-phosphorylated recombinant Tau possesses the necessary amino acid sequences for TOC1 binding but, unlike Tau12, the primary structure is not the only determinant of the interaction between oligomeric Tau and TOC1. To determine the amino acid sequences of Tau that serve as epitopes of TOC1, a recombinant library containing internal deletions of hTau40 was utilized (FIG. 7A). As this antibody requires aggregation of Tau for reactivity, deletion mutants were aggregated with AA prior to screening (FIG. 7B). The results suggest that TOC1 binding is mediated by two segments on Tau. The first region lies within the proline-rich region (Gly$^{155}$-Gln$^{244}$) and is absolutely necessary for TOC1 binding (FIG. 7C). Deletion of a second region (Leu$^{376}$-Ser$^{421}$) contained within the C-terminal portion of the protein causes 50% reduction in TOC1 binding. Given that these two regions are on either side of the MTBR, the results are consistent with the formation of an antiparallel dimer (FIG. 7D).

The deletion of residues Cys$^{291}$-Arg$^{349}$ also results in 50% reduction of TOC1 signal. Because this deletion lacks a large portion of the MTBR domain, it is not surprising that it aggregates poorly in comparison with the other internal deletion mutants (FIG. 7B). Therefore, the presence of this region is necessary for Tau aggregation and deletion of this region likely obstructs the formation of the TOC1 epitope. As an additional control, we also tested a construct that possessed only the MTBRs (Gln$^{244}$-Glu$^{372}$), and TOC1 showed no affinity for this construct. This indicates that this antibody does not recognize the portion of the Tau aggregates possessing (β-pleated sheets (57) in the absence of the rest of the Tau molecule. Nonetheless, the possibility that the MTBRs may comprise part of the epitope should not be completely ruled out.

A potential caveat of these experiments is that deletion of these amino acid sequences could alter the conformation of Tau in such a way as to obscure or prevent the formation of the TOC1 epitope potentially obfuscating our results. Therefore, future experiments will be necessary to refine this preliminary mapping of the TOC1 epitope.

g. TOC1 Immunoreactivity is Elevated in AD

Figure 8:
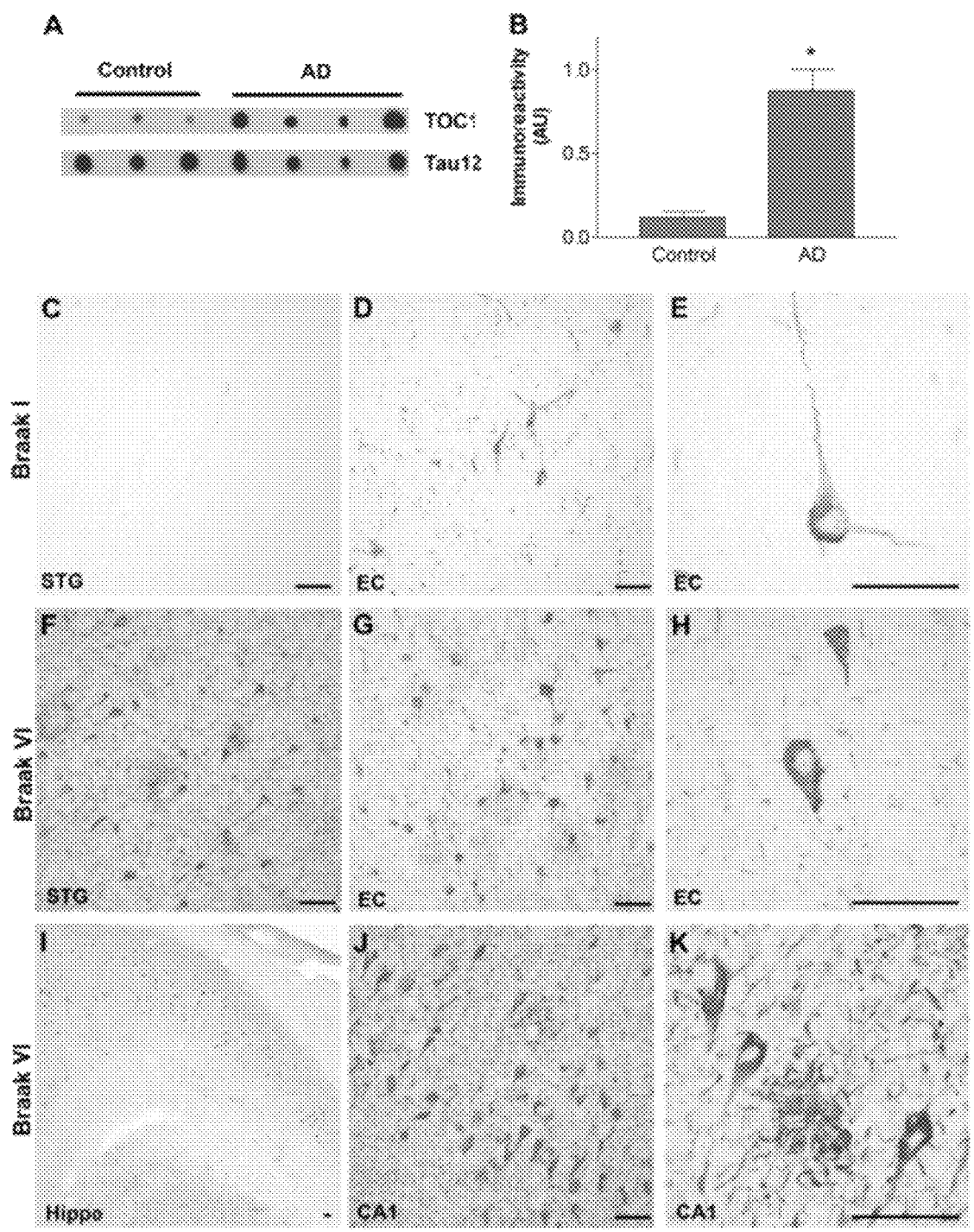
FIG. 8A-8K depict TOC1 immunoreactivity elevated in AD.

Using the TOC1 antibody, control and AD brains were examined for the presence of Tau oligomeric aggregates. Interestingly, Western blot analyses of AD homogenates or in vitro cross-linked Tau using TOC1 were unsuccessful. This indicates that even if Tau dimers do not dissociate when treated with SDS, the TOC1 conformation was not preserved. Thus, frontal cortex homogenates of control and severe AD cases were probed using dot blots under non-denaturing conditions. TOC1 demonstrated a marked increase in selectivity for AD samples over controls (FIGS. 8, A and B). These results not only demonstrate that Tau oligomers are elevated in AD but also validate the relevance of the TOC1 conformation to human disease.

To establish the spatial and temporal pattern of Tau oligomer formation in AD, TOC1 immunohistochemistry was performed on tissue sections from severe AD (Braak V and VI) and age-matched control cases (Braak I and II). Qualitative examination of sections from the entorhinal cortex, hippocampus, and superior temporal gyrus indicate that TOC1 reactivity follows the characteristic pattern of Braak staging (1) (FIG. 8). In control cases, TOC1 revealed neuropil threads as well as diffusely labeled neurons displaying both apical and basal dendritic processes (FIG. 8, C-E). These pretangle neurons are one of the earliest identifiable indicators of Tau deposition. As anticipated, a substantial increase in TOC1-positive inclusions was observed with increasing disease severity. In severe AD cases, TOC1 labels much of the classical Tau AD pathology, including neuropil threads, neuritic plaques, and neuronal pretangle and NFT-bearing inclusions (FIG. 8, F-K). These data indicate that Tau oligomerizaton is an early event in AD pathogenesis and that oligomers persist throughout the duration of the disease.

h. TOC1 Immunoreactivity Precedes NFT Formation

Figure 9:
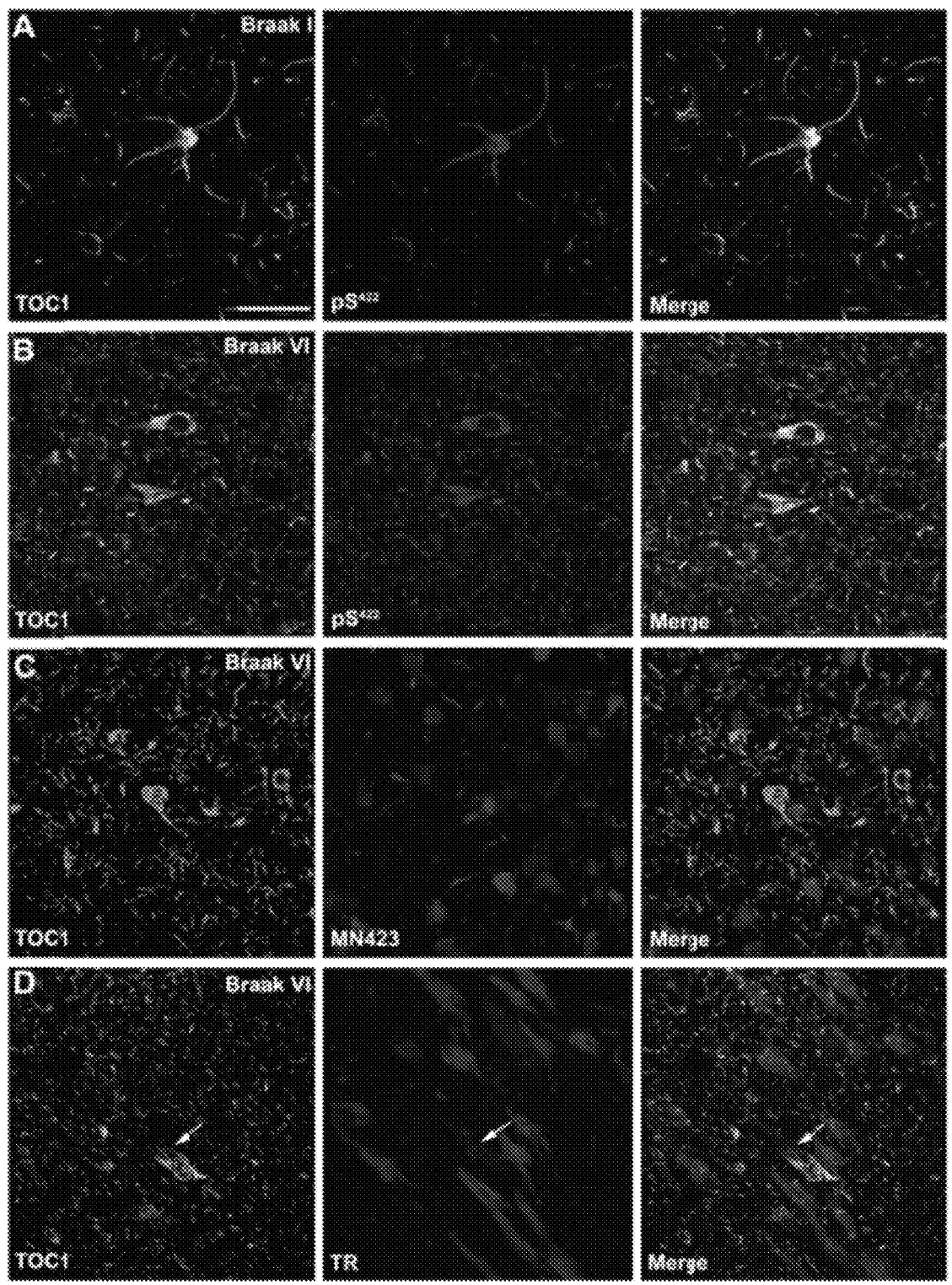
FIGS. 9A-9D depict TOC1 immunoreactivity colocalizing with early markers of Tau pathology.

To further delineate the temporal pattern of Tau oligomer formation, it was investigated whether TOC1 positive inclusions correlate with early or late stage markers of tangle evolution in AD. The phosphorylation of serine 422 (pS422) on the Tau protein is an early modification in AD pathogenesis (58, 59). Thus, tissue sections from the entorhinal cortex of controls and severe AD cases were double-stained with TOC1 and pS422 antibodies using double label immunofluorescence. Qualitative observations revealed extensive colocalization of TOC1 and pS422 in both control and AD samples, and, as pathology progressed into AD, the amount of both TOC1 and pS422 reactivity increased (FIGS. 9, A and B).

Next, TOC1 immunofluorescence was compared with that of a late stage NFT marker, MN423. MN423 recognizes Tau truncated at Glu391 (60). Qualitative analysis of severe AD cases revealed that TOC1 and MN423 reactivity are rarely observed in the same cell, indicating that the TOC1 epitope disappears prior to the truncation of Tau at residue 391 (FIG. 9C).

To establish whether or not TOC1 immunoreactivity is associated with mature NFTs, immunofluorescence with TOC1 and Thiazin Red (TR) was performed. TR is a fluorescent dye that recognizes β-pleated sheet conformation in the neurofibrillary pathology of AD (61). The criteria of TR staining to differentiate between neurons containing seemingly more mature NFTs and those containing granular diffuse aggregates of Tau characteristic of early pretangle neurons was used. Interestingly, in areas possessing abundant TR-positive pathology, TOC1 predominantly labeled dystrophic neurites and neuropil threads but did not colocalize with TR (FIG. 9D). Occasionally, TOC1 labeled cells containing TR positive NFT pathology; however, TOC1 was primarily confined to the periphery of the tangles in these instances. Taken together, this data indicated that Tau oligomer formation represents an early event in AD pathogenesis that precedes neurofibrillary degeneration.

Example 2

TOC1 Deletion Maping

Two overlapping tau deletion constructs (Δ209-228 and Δ221-238) were aggregated and incubated with the TOC1 antibody or with the Tau7 antibody. Both were positive for Tau7 which recognizes the last 11 amino acids of tau, but negative for TOC1. This result indicates that the shared deletion region 221-228 forms an essential part of the TOC1 epitope.

Example 3

Immunogold labeling and Dot Blots of TOC1 were conducted using the following Immunogold Protocol Dot Blots:
Immunogold Protocol
Sample—2 mins
dH20—5×1 min
Block—30 mins (0.2% Gelatin, 5% Goat Serum in 1×TBS)
Primary—TOC1 1:2500 (0.4 μg/ml) in Block—45 mins
1×TBS-4×2 min
Secondary—6 nm colloidal gold Anti-Mouse IgM n-chain 1:50 in Block—45 mins
10×TBS—5 mins dH20—4×2 min 2% Uranyl Acetate in dH20

Dot Blots:

50 ng of each sucrose fraction was used for dot blots. Tau7 was used 1:2,200,000 and TOC1 was used 1:10,000 (0.1 μmg/ml) in 5% non-fat dry milk in 0.05% Triton/1×TBS.

The results of the labeling are depicted in FIGS. 14A-14L. Figures shows electron microscopy from the resulting fractions after 1 ml of 4 μm aggregated tau was loaded on top of a 4 ml 20%-50% sucrose gradient and spun for 2 hours at 50K rpm. Immunogold labeling with the TOC1 antibody shows TOC1 preference for Fraction 3, which corresponds to the oligomer fraction also observed in human AD brains (Maeda et al., 2007; Biochemistry 46, 3856-3861).

It should be noted that TOC1 does not work in the presence of glutaraldehyde fixation, which is used in negatively stained EM images (0.1% Glutaraldehyde for 10 mins). Furthermore, the negative staining is particularly compromised when TOC1 immunogold is performed on sucrose fractions, rather than a normal aggregate preparation.

Example 4

TOC1 was sequenced. The $V_L$ sequence was obtained using degenerated primer method, and updated using RACE method. The following information was obtained:

```
Heavy chain: DNA sequence (1788 bp) (SEQ ID No: 11):
Leader sequence-FR1-CDR1-FR2-CDR2-FR3-CDR3-FR4-Constant
region-Stop codon:
ATGGGATGGAGCTGTATCATCCTCTTCTTGGTATCAACAGCTACAGGTGTCCACTCC-

CAGGTCCAACTGCAGCAGCCTGGGGCTGAGCTTGTGATGCCTGGGGCTTCAGTGAAGCTGTC

CTGCAAGGCTTCT-GGCTACACCTTCACCAGCTACTGGATGCAC-

TGGGTGAAGCAGAGGCCTGGACAAGGCCTTGAGTGGATCGGA-

GAGATTGATCCTTCTGATAGTTATACTAACTACAATCAAAAGTTCAAGGGC-

AAGTCCACATTGACTGTAGACAAATCCTCCAGCACAGCCTACATGCAGCTCAGCAGCCTGAC

ATCTGAGGACTCTGCGGTCTATTACTGTGCAAGA-

AGTGGGGACGGTAGTAGCCCCTGGTACTTCGATGTC-

TGGGGCACAGGGACCACGGTCACCGTCTCCTCA-

GAGAGTCAGTCCTTCCCAAATGTCTTCCCCCTCGTCTCCTGCGAGAGCCCCCTGTCTGATAA

GAATCTGGTGGCCATGGGCTGCCTGGCCCGGGACTTCCTGCCCAGCACCATTTCCTTCACCT

GGAACTACCAGAACAACACTGAAGTCATCCAGGGTATCAGAACCTTCCCAACACTGAGGACA

GGGGGCAAGTACCTAGCCACCTCGCAGGTGTTGCTGTCTCCCAAGAGCATCCTTGAAGGTTC

AGATGAATACCTGGTATGCAAAATCCACTACGGAGGCAAAAACAAAGATCTGCATGTGCCCA

TTCCAGCTGTCGCAGAGATGAACCCCAATGTAAATGTGTTCGTccCACCACGGGATGGCTTC

TCTGGCCCTGCACCACGCAAGTCTAAACTCATCTGCGAGGCCACGAACTTCACTCCAAAACC

GATCACAGTATCCTGGCTAAAGGATGGGAAGCTCGTGGAATCTGGCTTCACCACAGATCCGG

TGACCATCGAGAACAAAGGATCCACACCCCAAACCTACAAGGTCATAAGCACACTTACCATC

TCTGAAATCGACTGGCTGAACCTGAATGTGTACACCTGCCGTGTGGATCACAGGGGTCTCAC

CTTCTTGAAGAACGTGTCCTCCACATGTGCTGCCAGTCCCTCCACAGACATCCTAACCTTCA

CCATCCCCCCCTCCTTTGCCGACATCTTCCTCAGCAAGTCCGCTAACCTGACCTGTCTGGTC

TCAAACCTGGCAACCTATGAAACCCTGAATATCTCCTGGGCTTCTCAAAGTGGTGAACCACT

GGAAACCAAAATTAAAATCATGGAAAGCCATCCCAATGGCACCTTCAGTGCTAAGGGTGTGG

CTAGTGTTTGTGTGGAAGACTGGAATAACAGGAAGGAATTTGTGTGTACTGTGACTCACAGG

GATCTGCCTTCACCACAGAAGAAATTCATCTCAAAACCCAATGAGGTGCACAAACATCCACC

TGCTGTGTACCTGCTGCCACCAGCTCGTGAGCAACTGAACCTGAGGGAGTCAGCCACAGTCA

CCTGCCTGGTGAAGGGCTTCTCTCCTGCAGACATCAGTGTGCAGTGGCTTCAGAGAGGGCAA

CTCTTGCCCCAAGAGAAGTATGTGACCAGTGCCCCGATGCCAGAGCCTGGGGCCCCAGGCTT

CTACTTTACCCACAGCATCCTGACTGTGACAGAGGAGGAATGGAACTCCGGAGAGACCTATA

CCTGTGTTGTAGGCCACGAGGCCCTGCCACACCTGGTGACCGAGAGGACCGTGGACAAGTCC
```

ACTGGTAAACCCACACTGTACAATGTCTCCCTGATCATGTCTGACACAGGCGGCACCTGCTA

T-TGA

Heavy chain: Amino acids sequence (595 AA) (SEQ ID No: 12):
Leader sequence-FR1-CDR1-FR2-CDR2-FR3-CDR3-FR4-Constant
region-Stop codon:
MGWSCIILFLVSTATGVHSQVQLQQPGAELVMPGASVKLSCKAS-GYTFTSYWMH-

WVKQRPGQGLEWIGEIDPSDSYTNYNQKFKG-

KSTLTVDKSSSTAYMQLSSLTSEDSAVYYCAR-SGDGSSPWYFDV-WGTGTTVTVSS-

ESQSFPNVFPLVSCESPLSDKNLVAMGCLARDFLPSTISFTWNYQNNTEVIQGIRTFPTLRT

GGKYLATSQVLLSPKSILEGSDEYLVCKIHYGGKNKDLHVPIPAVAEMNPNVNVFVPPRDGF

SGPAPRKSKLICEATNFTPKPITVSWLKDGKLVESGFTTDPVTIENKGSTPQTYKVISTLTI

SEIDWLNLNVYTCRVDHRGLTFLKNVSSTCAASPSTDILTFTIPPSFADIFLSKSANLTCLV

SNLATYETLNISWASQSGEPLETKIKIMESHPNGTFSAKGVASVCVEDWNNRKEFVCTVTHR

DLPSPQKKFISKPNEVHKHPPAVYLLPPAREQLNLRESATVTCLVKGFSPADISVQWLQRGQ

LLPQEKYVTSAPMPEPGAPGFYFTHSILTVTEEEWNSGETYTCVVGHEALPHLVTERTVDKS

TGKPTLYNVSLIMSDTGGTCY-

Light chain: DNA sequence (717 bp) (SEQ ID No: 13):
Leader sequence-FR1-CDR1-FR2-CDR2-FR3-CDR3-FR4-Constant
region-Stop codon:
ATGAAGTTGCCTGTTAGGCTGTTGGTGCTGATGTTCTGGATTCCTGCTTCCAGCAGT-

GATGTTTTGATGACCCAAACTCCACTCTCCCTGCCTGTCAGTCTTGGAGATCAAGCCTCCAT

CTCTTGC-AGATCTAGTCAGAGCATTGTACATAGTAATGGAAACACCTATTTAGAA-

TGGTACCTGCAGAAACCAGGCCAGTCTCCAAAGCTCCTGATCTAC-

AAAGTTTCCAACCGATTTTCT-

GGGGTCCCAGACAGGTTCAGTGGCAGTGGATCAGGGACAGATTTCACACTCAAGATCAGCAG

AGTGGAGGCTGAGGATCTGGGAGTTTATTACTGC-

TTTCAAGGTTCACATGTTCCTCGGACG-TTCGGTGGAGGCACCAAGCTGGAAATCAAA-

CGGGCTGATGCTGCACCAACTGTATCCATCTTCCCACCATCCAGTGAGCAGTTAACATCTGG

AGGTGCCTCAGTCGTGTGCTTCTTGAACAACTTCTACCCCAAAGACATCAATGTCAAGTGGA

AGATTGATGGCAGTGAACGACAAAATGGCGTCCTGAACAGTTGGACTGATCAGGACAGCAAA

GACAGCACCTACAGCATGAGCAGCACCCTCACGTTGACCAAGGACGAGTATGAACGACATAA

CAGCTATACCTGTGAGGCCACTCACAAGACATCAACTTCACCCATTGTCAAGAGCTTCAACA

GGAATGAGTGT-TAG

Light chain: Amino acids sequence (238 AA) (SEQ ID NO: 14):
Leader sequence-FR1-CDR1-FR2-CDR2-FR3-CDR3-FR4-Constant
region-Stop codon:
MKLPVRLLVLMFWIPASSS-DVLMTQTPLSLPVSLGDQASISC-RSSQSIVHSNGNTYLE-

WYLQKPGQSPKLLIY-KVSNRFS-GVPDRFSGSGSGTDFTLKISRVEAEDLGVYYC-

FQGSHVPRT-FGGGTKLEIK-

RADAAPTVSIFPPSSEQLTSGGASVVCFLNNFYPKDINVKWKIDGSERQNGVLNSWTDQDSK

DSTYSMSSTLTLTKDEYERHNSYTCEATHKTSTSPIVKSFNRNEC-

The underlined "S" in the FR3 of $V_H$ is a mutant site. Most of the time, this site won't affect the binding.

Hybridomas producing TOC1 were deposited with ATCC.

Example 5

Aggregation of 4 μM hTau40 was induced using 75 μM arachidonic acid (AA) at room temperature. Aggregation assays were performed in a solution containing 10 mM HEPES pH 7.6, 100 mM NaCl, 0.1 mM EGTA and 5 mm DTT. Aggregation was stopped after 15 minutes or after 6 hours. An unaggregated preparation was also made in the same solution but lacking the AA.

For the immunogold experiments, TOC1 antibody was incubated with both oligomer and oligomer+filament preparations made as outlined above. The aggregate preparations were adhered to carbon over formvar grids, the grids blocked as noted in the protocol, prior to incubation for 1 hour with 0.4 μg/ml TOC1 antibody. After incubation, and several washing steps, TOC1 was reacted with a secondary antibody conjugated to colloidal gold. Most of the aggregates seen after 15 minutes of assembly were TOC1-positive while after 6 hours incubation, only oligomers were labeled as the filaments did not react with TOC1.

In order to better characterize structural changes in tau and further investigate which forms of aggregated tau are recognized by the TOC1 antibody, a sucrose density gradient centrifugation protocol on fully aggregated recombinant tau which contains a mixture of oligomers and filaments was used. 1 ml of a 6 hour tau aggregation preparation was layered on top of a 4 ml sucrose gradient containing four 1 ml layers with 20%, 30%, 40%, or 50% sucrose in a buffer of 10 mM Hepes, 100 mM NaCl and 0.1 mM EGTA. The sucrose solutions were centrifuged for 2 hours at 50,000 rpm in a Ti-55 Roter using a Beckman Coulter Optima MAX-E ultracentrifuge at 23° C. Each of the fractions were pipetted out separately and are referred to as fractions 1, 2, 3, 4, and 5, containing 0%, 20%, 30%, 40%, and 50% sucrose, respectively.

Negatively stained EM images of fractions 1-5 reveal a distinct separation of long filaments (Fraction 5), short filaments interspersed with oligomers (Fraction 4), and large oligomers (Fraction 3), with smaller oligomers and most likely dimers and monomers in Fractions 2 and 1, respectively.

Negative staining of the five fractions following reaction with TOC1 (0.4 μg/ml) and a secondary antibody conjugated to colloidal gold reveals a relatively small amount of gold particles in Fractions 1, 2, 4, and 5, and significant gold labeling in Fraction 3. The preferential labeling of TOC1 in Fraction 3 suggests that TOC1 is oligomer-selective as no monomers or filaments are present in this fraction.

However, to confirm this result, 50 ng of each fraction was used in dot blots and probed separately for TOC1 (0.1 μg/ml) and Tau7 (0.5 ng/ml), as described above in Example 3. TOC1 immunoreactivity was detected in fractions 2 and 3, with higher reactivity in fraction 3. This is confirmed with dot blot densitometry comparing the ratio of TOC1:Tau7 for each fraction (Tau7 recognizes all unaggregated and aggregated forms of tau). As in the negative stain described above, TOC1 immunoreactivity peaks in fraction 3, which further supports the idea that TOC1 is oligomer-selective.

In the preceding specification, the invention has been described with reference to specific exemplary embodiments and examples thereof. It will, however, be evident that various modifications and changes may be made thereto without departing from the broader spirit and scope of the invention as set forth in the claims that follow. The specification and drawings are accordingly to be regarded in an illustrative manner rather than a restrictive sense.

All references cited herein, including journal articles or abstracts, published or unpublished U.S. or foreign patent applications, issued U.S. or foreign patents, or any other references, are entirely incorporated by reference herein, including all data, tables, figures, and text presented in the cited references. Additionally, the entire contents of the references cited within the references cited herein are also entirely incorporated by reference.

Reference to known method steps, conventional methods steps, known methods or conventional methods is not in any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

1. Braak, H., and Braak, E. (1991) Acta Neuropathol. 82, 239-259
2. Arriagada, P. V., Growdon, J. H., Hedley-Whyte, E. T., and Hyman, B. T. (1992) Neurology 42, 631-639
3. Rapoport, M., Dawson, H. N., Binder, L. I., Vitek, M. P., and Ferreira, A. (2002) Proc. Natl. Acad. Sci. U.S.A. 99, 6364-6369
4. Roberson, E. D., Scearce-Levie, K., Palop, J. J., Yan, F., Cheng, I. H., Wu, T., Gerstein, H., Yu, G. Q., and Mucke, L. (2007) Science 316, 750-754
5. Vossel, K. A., Zhang, K., Brodbeck, J., Daub, A. C., Sharma, P., Finkbeiner, S., Cui, B., and Mucke, L. (2010) Science 330, 198
6. Feany, M. B., and Dickson, D. W. (1996) Ann. Neurol. 40, 139-148
7. Poorkaj, P., Bird, T. D., Wijsman, E., Nemens, E., Garruto, R. M., Ander-son, L., Andreadis, A., Wiederholt, W. C., Raskind, M., and Schellenberg, G. D. (1998) Ann. Neurol. 43, 815-825
8. Poorkaj, P., Grossman, M., Steinbart, E., Payami, H., Sadovnick, A., Noch-lin, D., Tabira, T., Trojanowski, J. Q., Borson, S., Galasko, D., Reich, S., Quinn, B., Schellenberg, G., and Bird, T. D. (2001) Arch. Neurol. 58, 383-387
9. Spillantini, M. G., Murrell, J. R., Goedert, M., Farlow, M. R., Klug, A., and Ghetti, B. (1998) Proc. Natl. Acad. Sci. U.S.A. 95, 7737-7741
10. Hutton, M., Lendon, C. L., Rizzu, P., Baker, M., Froelich, S., Houlden, H., Pickering-Brown, S., Chakraverty, S., Isaacs, A., Grover, A., Hackett, J., Adamson, J., Lincoln, S., Dickson, D., Davies, P., Petersen, R. C., Stevens, M., de Graaff, E., Wauters, E., van Baren, J., Hillebrand, M., Joosse, M., Kwon, J. M., Nowotny, P., Che, L. K., Norton, J., Morris, J. C., Reed, L. A., Trojanowski, J., Basun, H., Lannfelt, L., Neystat, M., Fahn, S., Dark, F., Tannenberg, T., Dodd, P. R., Hayward, N., Kwok, J. B., Schofield, P. R., Andreadis, A., Snowden, J., Craufurd, D., Neary, D., Owen, F., Oostra, B. A., Hardy, J., Goate, A., van Swieten, J., Mann, D., Lynch, T., and Heu-tink, P. (1998) Nature 393, 702-705

11. Schweers, O., Schonbrunn-Hanebeck, E., Marx, A., and Mandelkow, E. (1994) J. Biol. Chem. 269, 24290-24297
12. Iqbal, K., Liu, F., Gong, C. X., Alonso Adel, C., and Grundke-Iqbal, I. (2009) Acta Neuropathol. 118, 53-69
13. von Bergen, M., Friedhoff, P., Biernat, J., Heberle, J., Mandelkow, E. M., and Mandelkow, E. (2000) Proc. Natl. Acad. Sci. U.S.A. 97, 5129-5134
14. Lewis, J., McGowan, E., Rockwood, J., Melrose, H., Nacharaju, P., Van Slegtenhorst, M., Gwinn-Hardy, K., Paul Murphy, M., Baker, M., Yu, X., Duff, K., Hardy, J., Corral, A., Lin, W. L., Yen, S. H., Dickson, D. W., Davies, P., and Hutton, M. (2000) Nat. Genet. 25, 402-405
15. Gotz, J., Chen, F., Barmettler, R., and Nitsch, R. M. (2001) J. Biol. Chem. 276, 529-534
16. Tanemura, K., Akagi, T., Murayama, M., Kikuchi, N., Murayama, O., Ha-shikawa, T., Yoshiike, Y., Park, J. M., Matsuda, K., Nakao, S., Sun, X., Sato, S., Yamaguchi, H., and Takashima, A. (2001) Neurobiol. Dis. 8, 1036-1045
17. Tatebayashi, Y., Miyasaka, T., Chui, D. H., Akagi, T., Mishima, K., Iwasaki, K., Fujiwara, M., Tanemura, K., Murayama, M., Ishiguro, K., Planel, E., Sato, S., Hashikawa, T., and Takashima, A. (2002) Proc. Natl. Acad. Sci. U.S.A. 99, 13896-13901
18. Allen, B., Ingram, E., Takao, M., Smith, M. J., Jakes, R., Virdee, K., Yoshida, H., Holzer, M., Craxton, M., Emson, P. C., Atzori, C., Migheli, A., Crowther, R. A., Ghetti, B., Spillantini, M. G., and Goedert, M. (2002) J. Neurosci. 22, 9340-9351
19. Andorfer, C., Acker, C. M., Kress, Y., H of, P. R., Duff, K., and Davies, P. (2005) J. Neurosci. 25, 5446-5454
20. Oddo, S., Caccamo, A., Shepherd, J. D., Murphy, M. P., Golde, T. E., Kayed, R., Metherate, R., Mattson, M. P., Akbari, Y., and LaFerla, F. M. (2003) Neuron 39, 409-421
21. Spires, T. L., Orne, J. D., SantaCruz, K., Pitstick, R., Carlson, G. A., Ashe, K. H., and Hyman, B. T. (2006) Am. J. Pathol. 168, 1598-1607
22. Santacruz, K., Lewis, J., Spires, T., Paulson, J., Kotilinek, L., Ingelsson, M., Guimaraes, A., DeTure, M., Ramsden, M., McGowan, E., Forster, C., Yue, M., Orne, J., Janus, C., Mariash, A., Kuskowski, M., Hyman, B., Hutton, M., and Ashe, K. H. (2005) Science 309, 476-481
23. Sydow, A., Van der Jeugd, A., Zheng, F., Ahmed, T., Balschun, D., Petrova, O., Drexler, D., Zhou, L., Rune, G., Mandelkow, E., D'Hooge, R., Alzheimer, C., and Mandelkow, E. M. (2011) J. Neurosci. 31, 2511-2525
24. Wittmann, C. W., Wszolek, M. F., Shulman, J. M., Salvaterra, P. M., Lewis, J., Hutton, M., and Feany, M. B. (2001) Science 293, 711-714
25. Berger, Z., Roder, H., Hanna, A., Carlson, A., Rangachari, V., Yue, M., Wszolek, Z., Ashe, K., Knight, J., Dickson, D., Andorfer, C., Rosenberry, T. L., Lewis, J., Hutton, M., and Janus, C. (2007) J. Neurosci. 27, 3650-3662
26. Friedhoff, P., von Bergen, M., Mandelkow, E. M., Davies, P., and Man-delkow, E. (1998) Proc. Natl. Acad. Sci. U.S.A. 95, 15712-15717
27. Congdon, E. E., Kim, S., Bonchak, J., Songrug, T., Matzavinos, A., and Kuret, J. (2008) J. Biol. Chem. 283, 13806-13816
28. Lasagna-Reeves, C. A., Castillo-Carranza, D. L., Guerrero-Muoz, M. J., Jackson, G. R., and Kayed, R. (2010) Biochemistry 49, 10039-10041
29. Sahara, N., Maeda, S., Murayama, M., Suzuki, T., Dohmae, N., Yen, S. H., and Takashima, A. (2007) Eur. J. Neurosci. 25, 3020-3029
30. Barghorn, S., and Mandelkow, E. (2002) Biochemistry 41, 14885-14896
31. Schweers, O., Mandelkow, E. M., Biernat, J., and Mandelkow, E. (1995) Proc. Natl. Acad. Sci. U.S.A. 92, 8463-8467
32. Gamblin, T. C., King, M. E., Kuret, J., Berry, R. W., and Binder, L. I. (2000) Biochemistry 39, 14203-14210
33. Lee, V. M., Goedert, M., and Trojanowski, J. Q. (2001) Annu. Rev. Neuro-sci. 24, 1121-1159
34. Goedert, M., Spillantini, M. G., Potier, M. C., Ulrich, J., and Crowther, R. A. (1989) EMBO. J. 8, 393-399
35. Carmel, G., Mager, E. M., Binder, L. I., and Kuret, J. (1996) J. Biol. Chem. 271, 32789-32795
36. Abraha, A., Ghoshal, N., Gamblin, T. C., Cryns, V., Berry, R. W., Kuret, J., and Binder, L. I. (2000) J. Cell Sci. 113, 3737-3745
37. Gamblin, T. C., Berry, R. W., and Binder, L. I. (2003) Biochemistry 42, 2252-2257
38. Cannel, G., Leichus, B., Cheng, X., Patterson, S. D., Mirza, U., Chait, B. T., Kuret, J. (1994) J. Biol. Chem. 269, 7304-7309
39. Gamblin, T. C., King, M. E., Dawson, H., Vitek, M. P., Kuret, J., Berry, R. W., and Binder, L. I. (2000) Biochemistry 39, 6136-6144
40. Necula, M., Chirita, C. N., and Kuret, J. (2003) J. Biol. Chem. 278, 46674-46680
41. Stine, W. B., Jungbauer, L., Yu, C., and LaDu, M. J. (2011) Methods Mol. Biol. 670, 13-32
42. Binder, L. I., Frankfurter, A., and Rebhun, L. I. (1985) J. Cell Biol. 101, 1371-1378
43. Reyes, J. F., Reynolds, M. R., Horowitz, P. M., Fu, Y., Guillozet-Bon-gaarts, A. L., Berry, R., and Binder, L. I. (2008) Neurobiol. Dis. 31, 198-208
44. LaPointe, N. E., Morfini, G., Pigino, G., Gaisina, I. N., Kozikowski, A. P., Binder, L. I., and Brady, S. T. (2009) J. Neurosci. Res. 87, 440-451
45. Horowitz, P. M., Patterson, K. R., Guillozet-Bongaarts, A. L., Reynolds, M. R., Carroll, C. A., Weintraub, S. T., Bennett, D. A., Cryns, V. L., Berry, R. W., and Binder, L. I. (2004) J. Neurosci. 24, 7895-7902
46. LoPresti, P., Szuchet, S., Papasozomenos, S. C., Zinkowski, R. P., and Binder, L. I. (1995) Proc. Natl. Acad. Sci. U.S.A. 92, 10369-10373
47. Horowitz, P. M., LaPointe, N., Guillozet-Bongaarts, A. L., Berry, R. W., and Binder, L. I. (2006) Biochemistry 45, 12859-12866
48. Berry, R. W., Sweet, A. P., Clark, F. A., Lagalwar, S., Lapin, B. R., Wang, T., Topgi, S., Guillozet-Bongaarts, A. L., Cochran, E. J., Bigio, E. H., and Binder, L. I. (2004) J. Neurocytol. 33, 287-295
49. Kanaan, N. M., Kordower, J. H., and Collier, T. J. (2007) J. Comp. Neurol. 502, 683-700
50. Garcia-Sierra, F., Ghoshal, N., Quinn, B., Berry, R. W., and Binder, L. I. (2003) J. Alzheimers Dis. 5, 65-77
51. Novak, M., Wischik, C. M., Edwards, P., Pannell, R., and Milstein, C. (1989) Prog. Clin. Biol. Res. 317, 755-761
52. Dorman, G., and Prestwich, G. D. (1994) Biochemistry 33, 5661-5673
53. Gamblin, T. C., Chen, F., Zambrano, A., Abraha, A., Lagalwar, S., Guil-lozet, A. L., Lu, M., Fu, Y., Garcia- Sierra, F., LaPointe, N., Miller, R., Berry, R. W., Binder, L. I., and Cryns, V. L. (2003) Proc. Natl. Acad. Sci. U.S.A. 100, 10032-10037

54. Novak, M., Kabat, J., and Wischik, C. M. (1993) EMBO J. 12, 365-370

55. Guo, H., Albrecht, S., Bourdeau, M., Petzke, T., Bergeron, C., and LeBlanc, A. C. (2004) Am. J. Pathol. 165, 523-531

56. Maeda, S., Sahara, N., Saito, Y., Murayama, S., Ikai, A., and Takashima, A. (2006) Neurosci. Res. 54, 197-201

57. Barghorn, S., Davies, P., and Mandelkow, E. (2004) Biochemistry 43, 1694-1703

58. Guillozet-Bongaarts, A. L., Cahill, M. E., Cryns, V. L., Reynolds, M. R., Berry, R. W., and Binder, L. I. (2006) J. Neurochem. 97, 1005-1014

59. Mondragon-Rodriguez, S., Basurto-Islas, G., Santa-Maria, I., Mena, R., Binder, L. I., Avila, J., Smith, M. A., Perry, G., and Garcia-Sierra, F. (2008) Int. J. Exp. Pathol. 89, 81-90

60. Guillozet-Bongaarts, A. L., Garcia-Sierra, F., Reynolds, M. R., Horowitz, P. M., Fu, Y., Wang, T., Cahill, M. E., Bigio, E. H., Berry, R. W., and Binder, L. I. (2005) Neurobiol. Aging 26, 1015-1022

61. Luna-Munoz, J., Peralta-Ramirez, J., Chavez-Macías, L., Harrington, C. R., Wischik, C. M., and Mena, R. (2008) Acta Neuropathol. 116, 507-515

62. Kidd, M. (1963) Nature 197, 192-193

63. Kosik, K. S., Joachim, C. L., and Selkoe, D. J. (1986) Proc. Natl. Acad. Sci. U.S.A. 83, 4044-4048

64. Gomez-Isla, T., Hollister, R., West, H., Mui, S., Growdon, J. H., Pe-tersen, R. C., Parisi, J. E., and Hyman, B. T. (1997) Ann. Neurol. 41, 17-24

65. Chirita, C. N., Congdon, E. E., Yin, H., and Kuret, J. (2005) Biochemistry 44, 5862-5872

66. Wilson, D. M., and Binder, L. I. (1995) J. Biol. Chem. 270, 24306-24314

67. Perez, M., Valpuesta, J. M., Medina, M., Montejo de Garcini, E., and Avila, J. (1996) J. Neurochem. 67, 1183-1190

68. Kampers, T., Friedhoff, P., Biernat, J., Mandelkow, E. M., and Mandelkow, E. (1996) FEBS. Lett. 399, 344-349

69. Guttmann, R. P., Erickson, A. C., and Johnson, G. V. (1995) J. Neurochem. 64, 1209-1215

70. Maeda, S., Sahara, N., Saito, Y., Murayama, M., Yoshiike, Y., Kim, H., Miyasaka, T., Murayama, S., Ikai, A., and Takashima, A. (2007) Biochemistry 46, 3856-3861

71. Rosenberg, K. J., Ross, J. L., Feinstein, H. E., Feinstein, S. C., and Israel-achvili, J. (2008) Proc. Natl. Acad. Sci. U.S.A. 105, 7445-7450

72. Wille, H., Drewes, G., Biernat, J., Mandelkow, E. M., and Mandelkow, E. (1992) J. Cell Biol. 118, 573-584

73. Cabre, F., Canela, E. I., and Canela, M. A. (1989) J. Chromatogr. 472, 347-356

74. Sayre, L. M., Zelasko, D. A., Harris, P. L., Perry, G., Salomon, R. G., and Smith, M. A. (1997) J. Neurochem. 68, 2092-2097

75. Liu, Q., Smith, M. A., Avilá, J., DeBernardis, J., Kansal, M., Takeda, A., Zhu, X., Nunomura, A., Honda, K., Moreira, P. I., Oliveira, C. R., Santos, M. S., Shimohama, S., Aliev, G., de la Torre, J., Ghanbari, H. A., Siedlak, S. L., Harris, P. L., Sayre, L. M., and Perry, G. (2005) Free Radic. Biol. Med. 38, 746-754

76. Appelt, D. M., and Balin, B. J. (1997) Brain Res. 745, 21-31

77. Balin, B. J., and Appelt, D. M. (2000) Methods Mol. Med. 32, 395-404

78. Dudek, S. M., and Johnson, G. V. (1993) J. Neurochem. 61, 1159-1162

79. Singer, S. M., Zainelli, G. M., Norlund, M. A., Lee, J. M., and Muma, N. A. (2002) Neurochem. Int. 40, 17-30

80. Oosawa, F., and Asakura, S. (1975) Thermodynamics of the Polymerization of Protein, Academic Press, New York 81. Kriem, B., Sponne, I., Fifre, A., Malaplate-Armand, C., Lozac'h-Pillot, K., Koziel, V., Yen-Potin, F. T., Bihain, B., Oster, T., Olivier, J. L., and Pillot, T. (2005) FASEB 119, 85-87

82. Malaplate-Armand, C., Florent-Bechard, S., Youssef, I., Koziel, V., Sponne, I., Kriem, B., Leininger-Muller, B., Olivier, J. L., Oster, T., and Pillot, T. (2006) Neurobiol Dis. 23, 178-189

83. Sanchez-Mejia, R. 0., Newman, J. W., Toh, S., Yu, G. Q., Zhou, Y., Halabisky, B., Cisse, M., Scearce-Levie, K., Cheng, I. H., Gan, L., Palop, J. J., Bonventre, J. V., and Mucke, L. (2008) Nat. Neurosci. 11, 1311-1318

84. Farooqui, A. A., and Horrocks, L. A. (2006) Neuroscientist 12, 245-260

85. Jicha, G. A., Bowser, R., Kazam, I. G., and Davies, P. (1997) J. Neurosci, Res. 48, 128-132

86. Kanaan, N. M., Morfini, G., Lapointe, N. E., Pigino, G., Patterson, K. R., Song, Y., Andreadis, A., Brady, S. T., and Binder, L. I. (2011) J. Neurosci, in press.

---

What is claimed is:

1. A tau oligomeric complex-1 (TOC-1) monoclonal antibody comprising the heavy variable region of SEQ ID NO:7.

2. The antibody of claim 1, which is an IgG antibody.

3. The antibody of claim 1, wherein the antibody selectively recognizes prefibrillar Tau aggregates comprising at least two tau proteins cross-linked to each other, either directly or through a linker at one or more cysteine residues.

4. The antibody of claim 1, wherein the antibody comprises the light variable region of SEQ ID NO: 8.

5. The antibody of claim 1, wherein the antibody selectively recognizes a conformation induced by a cross-linked Tau dimer, wherein the cross-linked Tau dimer comprises at least two tau proteins cross-linked in vitro to each other, either directly or through a linker, at one or more cysteine residues.

6. An antibody comprising a variable region of the heavy chain which is the same as the heavy variable region of SEQ ID NO:7.

7. The antibody of claim 6, the epitope of which comprises a minimum of two Tau monomers.

8. The antibody of claim 6, whose epitope lies within ninety amino acids of a MTBR of hTau40.

9. The antibody of claim 8, whose epitope lies within a region of hTau40 selected from the group consisting of $Gly^{155}$-$Gln^{244}$, $Leu^{376}$-$Ser^{421}$, $Cys^{291}$-$Arg^{349}$, or a fragment of any of the foregoing.

10. The antibody of claim 9, wherein the epitope lies within $Gly^{155}$-$Gln^{244}$ or a fragment thereof.

11. The antibody of claim 6, wherein the antibody selectively recognizes prefibrillar Tau aggregates comprising at least two tau proteins cross-linked to each other, either directly or through a linker at one or more cysteine residues.

12. The antibody of claim 6, wherein the antibody selectively recognizes a conformation induced by a cross-linked Tau dimer, wherein the cross-linked Tau dimer comprises at least two tau proteins cross-linked in-vitro to each other, either directly or through a linker, at one or more cysteine residues.

13. The antibody of claim 6, which is an IgG antibody.

14. The antibody of any one of claim 1 or 6, which requires for binding a conformation comprising:
   at least two cross-linked Tau molecules, and
   a region of hTau40 selected from the group consisting of $Gly^{155}$-$Gln^{244}$, $Leu^{376}$-$Ser^{421}$, $Cys^{291}$-$Arg^{349}$, or a fragment of any of the foregoing.

15. A method of treating a tauopathy in a mammal, comprising administering to a mammal in need of therapy for a tauopathy an antibody according to claim 1 or an antibody according to claim 6.

16. The antibody of claim 1 or 6, which does not selectively recognize monomeric Tau.

17. The antibody of claim 1 or 6, which does not selectively react with α-synuclein.

18. The antibody of claim 1 or 6, which does not selectively react with Aβ in the unaggregated, oligomeric or filamentous states.

19. The antibody of claim 1 or 6, which is an IgM antibody.

* * * * *

SEQUENCE LISTING

<160> NUMBER OF SEQ ID NOS: 35

<210> SEQ ID NO 1
<211> LENGTH: 441
<212> TYPE: PRT
<213> ORGANISM: Artificial Sequence
<220> FEATURE:
<223> OTHER INFORMATION: HTAU40

<400> SEQUENCE: 1

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45
```

```
Gln Thr Pro Thr Glu Asp Gly Ser Glu Glu Pro Gly Ser Glu Thr Ser
 50                  55                  60

Asp Ala Lys Ser Thr Pro Thr Ala Glu Asp Val Thr Ala Pro Leu Val
 65                  70                  75                  80

Asp Glu Gly Ala Pro Gly Lys Gln Ala Ala Gln Pro His Thr Glu
                 85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
            115                 120                 125

Ser Lys Ser Lys Asp Gly Thr Gly Ser Asp Asp Lys Lys Ala Lys Gly
        130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
        195                 200                 205

Arg Ser Arg Thr Pro Ser Leu Pro Thr Pro Pro Thr Arg Glu Pro Lys
210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
            245                 250                 255

Lys Ser Lys Ile Gly Ser Thr Glu Asn Leu Lys His Gln Pro Gly Gly
        260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
        290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
            325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
            355                 360                 365

Lys Lys Ile Glu Thr His Lys Leu Thr Phe Arg Glu Asn Ala Lys Ala
        370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
        435                 440

<210> SEQ ID NO 2
<211> LENGTH: 410
<212> TYPE: PRT
<213> ORGANISM: Artificial
```

<220> FEATURE:
<223> OTHER INFORMATION: Human Tau 2N3R

<400> SEQUENCE: 2

```
Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Pro Gly Ser Glu Thr Ser
    50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Gln Pro His Thr Glu
                85                  90                  95

Ile Pro Glu Gly Thr Thr Ala Glu Ala Gly Ile Gly Asp Thr Pro
                100                 105                 110

Ser Leu Glu Asp Glu Ala Ala Gly His Val Thr Gln Ala Arg Met Val
            115                 120                 125

Ser Lys Ser Leu Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
                180                 185                 190

Asp Arg Ser Gly Tyr Ser Ser Pro Gly Ser Pro Gly Thr Pro Gly Ser
            195                 200                 205

Arg Ser Arg Thr Pro Ser Leu Pro Thr Pro Pro Thr Arg Glu Pro Lys
210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
                260                 265                 270

Gly Lys Val Gln Ile Val Tyr Lys Pro Val Asp Leu Ser Lys Val Thr
            275                 280                 285

Ser Lys Cys Gly Ser Leu Gly Asn Ile His His Lys Pro Gly Gly Gly
    290                 295                 300

Gln Val Glu Val Lys Ser Glu Lys Leu Asp Phe Lys Asp Arg Val Gln
305                 310                 315                 320

Ser Lys Ile Gly Ser Leu Asp Asn Ile Thr His Val Pro Gly Gly Gly
                325                 330                 335

Asn Lys Lys Ile Glu Thr His Lys Leu Thr Phe Arg Glu Asn Ala Lys
                340                 345                 350

Ala Lys Thr Asp His Gly Ala Glu Ile Val Tyr Lys Ser Pro Val Val
            355                 360                 365

Ser Gly Asp Thr Ser Pro Ala His Leu Ser Asn Val Ser Ser Thr Gly
    370                 375                 380

Ser Ile Asp Met Val Asp Ser Pro Gln Leu Ala Thr Leu Ala Asp Glu
385                 390                 395                 400
```

```
Val Ser Ala Ser Leu Ala Lys Gln Gly Leu
            405                 410

<210> SEQ ID NO 3
<211> LENGTH: 412
<212> TYPE: PRT
<213> ORGANISM: Artificial Sequence
<220> FEATURE:
<223> OTHER INFORMATION: Human Tau 1N4R

<400> SEQUENCE: 3

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Gly Asp Gly Ser Glu Glu Pro Gly Ser Glu Thr Ser
    50                  55                  60

Asp Ala Lys Ser Thr Pro Thr Ala Glu Ala Glu Glu Ala Gly Ile Gly
65                  70                  75                  80

Asp Thr Pro Ser Leu Glu Asp Glu Ala Ala Gly His Val Thr Gln Ala
                85                  90                  95

Arg Met Val Ser Lys Ser Leu Asp Gly Thr Gly Ser Asp Asp Lys Lys
            100                 105                 110

Ala Lys Gly Ala Asp Gly Lys Thr Leu Ile Ala Thr Pro Arg Gly Ala
        115                 120                 125

Ala Pro Pro Gly Gln Lys Gly Gln Ala Asn Ala Thr Arg Ile Pro Ala
    130                 135                 140

Lys Thr Pro Pro Ala Pro Lys Thr Pro Pro Ser Ser Gly Glu Pro Pro
145                 150                 155                 160

Lys Ser Gly Asp Arg Ser Gly Tyr Ser Ser Pro Gly Ser Pro Gly Thr
                165                 170                 175

Pro Gly Ser Arg Ser Arg Thr Pro Ser Leu Pro Thr Pro Pro Thr Arg
            180                 185                 190

Glu Pro Lys Lys Val Ala Val Val Arg Thr Pro Pro Lys Ser Pro Ser
        195                 200                 205

Ser Ala Lys Ser Arg Leu Gln Thr Ala Pro Val Pro Met Pro Asp Leu
    210                 215                 220

Lys Asn Val Lys Ser Lys Ile Gly Ser Thr Glu Asn Leu Lys His Gln
225                 230                 235                 240

Pro Gly Gly Gly Lys Val Gln Ile Ile Asn Lys Lys Leu Asp Leu Ser
                245                 250                 255

Asn Val Gln Ser Lys Cys Gly Ser Leu Asp Asn Ile Leu His Val Pro
            260                 265                 270

Gly Gly Gly Ser Val Gln Ile Val Tyr Lys Pro Val Asp Leu Ser Lys
        275                 280                 285

Val Thr Ser Lys Cys Gly Ser Leu Gly Asn Ile His His Lys Pro Gly
    290                 295                 300

Gly Gly Gln Val Glu Val Lys Ser Glu Lys Leu Asp Phe Lys Asp Arg
305                 310                 315                 320

Val Gln Ser Lys Ile Gly Ser Leu Asp Asn Ile Thr His Val Pro Gly
                325                 330                 335

Gly Gly Asn Lys Lys Ile Glu Thr His Lys Leu Thr Phe Arg Glu Asn
            340                 345                 350

Ala Lys Ala Lys Thr Asp His Gly Ala Glu Ile Val Tyr Lys Ser Pro
```

Val Val Ser Gly Asp Thr Ser Pro Arg His Leu Ser Asn Val Ser Ser
370                 375                 380

Thr Gly Ser Ile Asp Met Val Asp Ser Pro Gln Leu Ala Thr Leu Ala
385                 390                 395                 400

Asp Glu Val Ser Ala Ser Leu Ala Lys Gln Gly Leu
            405                 410

<210> SEQ ID NO 4
<211> LENGTH: 383
<212> TYPE: PRT
<213> ORGANISM: Artificial Sequence
<220> FEATURE:
<223> OTHER INFORMATION: Human Tau ON4R

<400> SEQUENCE: 4

Met Ala Glu Pro Arg Gln Glu Phe Glu Val Met Glu Asp His Ala Gly
1               5                   10                  15

Thr Tyr Gly Leu Gly Asp Arg Leu Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Ala Thr Pro Pro Lys Ser 
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Leu Ile Gly Ser Thr Glu Asn Leu
        195                 200                 205

Lys His Gln Pro Gly Gly Gly Lys Val Gln Ile Ile Asn Lys Lys Leu
    210                 215                 220

Asp Leu Ser Asn Val Gln Ser Lys Cys Gly Ser Lys Asp Asn Ile Lys
225                 230                 235                 240

His Val Pro Gly Gly Gly Ser Val Gln Ile Val Tyr Lys Pro Val Asp
                245                 250                 255

Leu Ser Lys Val Thr Ser Lys Cys Gly Ser Leu Gly Asn Ile His His
            260                 265                 270

Lys Pro Gly Gly Gly Gln Val Glu Val Lys Ser Glu Lys Leu Asp Phe
        275                 280                 285

Lys Asp Arg Val Gln Ser Lys Ile Gly Ser Leu Asp Asn Ile Thr His
    290                 295                 300

Val Pro Gly Gly Gly Asn Lys Lys Ile Glu Thr His Lys Leu Thr Phe
305                 310                 315                 320

```
Arg Glu Asn Ala Lys Ala Leu Thr Asp His Gly Ala Glu Ile Val Tyr
            325                 330                 335

Lys Ser Pro Val Val Ser Gly Asp Thr Ser Pro Arg His Leu Ser Asn
            340                 345                 350

Val Ser Ser Thr Gly Ser Ile Asp Met Val Asp Ser Pro Gln Leu Ala
            355                 360                 365

Thr Leu Ala Asp Glu Val Ser Ala Ser Leu Ala Lys Gln Gly Leu
            370                 375                 380

<210> SEQ ID NO 5
<211> LENGTH: 381
<212> TYPE: PRT
<213> ORGANISM: Artificial Sequence
<220> FEATURE:
<223> OTHER INFORMATION: Human Tau 1N3R

<400> SEQUENCE: 5

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Glu Ser Pro Leu
        35                  40                  45

Gln Thr Pro Thr Glu Asp Gly Ser Glu Glu Pro Gly Ser Glu Thr Ser
    50                  55                  60

Asp Ala Lys Ser Thr Pro Thr Ala Glu Ala Glu Glu Ala Gly Ile Gly
65                  70                  75                  80

Asp Thr Pro Ser Leu Glu Asp Glu Ala Ala Gly His Val Thr Gln Ala
                85                  90                  95

Arg Met Val Ser Lys Ser Lys Asp Gly Thr Gly Ser Asp Asp Lys Lys
            100                 105                 110

Ala Lys Gly Ala Asp Gly Lys Thr Lys Ile Ala Thr Pro Arg Gly Ala
        115                 120                 125

Ala Pro Pro Gly Gln Lys Gly Gln Ala Asn Ala Thr Arg Ile Pro Ala
    130                 135                 140

Lys Thr Pro Pro Ala Pro Lys Thr Pro Ser Ser Gly Glu Pro Pro
145                 150                 155                 160

Lys Ser Gly Asp Arg Ser Gly Tyr Ser Ser Pro Gly Ser Pro Gly Thr
            165                 170                 175

Pro Gly Ser Arg Ser Arg Thr Pro Ser Leu Pro Thr Pro Pro Thr Arg
        180                 185                 190

Glu Pro Lys Lys Val Ala Val Val Arg Thr Pro Pro Lys Ser Pro Ser
    195                 200                 205

Ser Ala Lys Ser Arg Leu Gln Thr Ala Pro Val Pro Met Pro Asp Leu
210                 215                 220

Lys Asn Val Lys Ser Lys Ile Gly Ser Thr Glu Asn Leu Lys His Gln
225                 230                 235                 240

Pro Gly Gly Gly Lys Val Gln Ile Val Tyr Lys Pro Val Asp Leu Ser
            245                 250                 255

Lys Val Thr Ser Lys Cys Gly Ser Leu Gly Asn Ile His His Lys Pro
        260                 265                 270

Gly Gly Gly Gln Val Glu Val Lys Ser Glu Lys Leu Asp Phe Lys Asp
    275                 280                 285

Arg Val Gln Ser Lys Ile Gly Ser Leu Asp Asn Ile Thr His Val Pro
290                 295                 300
```

```
Gly Gly Gly Asn Lys Lys Ile Glu Thr His Lys Leu Thr Phe Arg Glu
305                 310                 315                 320

Asn Ala Lys Ala Lys Thr Asp His Gly Ala Glu Ile Val Tyr Lys Ser
            325                 330                 335

Pro Val Val Ser Gly Asp Thr Ser Pro Arg His Leu Ser Asn Val Ser
            340                 345                 350

Ser Thr Gly Ser Ile Asp Met Val Asp Ser Pro Gln Leu Ala Thr Leu
            355                 360                 365

Ala Asp Glu Val Ser Ala Ser Leu Ala Lys Gln Gly Leu
            370                 375                 380

<210> SEQ ID NO 6
<211> LENGTH: 352
<212> TYPE: PRT
<213> ORGANISM: Artificial Sequence
<220> FEATURE:
<223> OTHER INFORMATION: Human Tau 0N3R

<400> SEQUENCE: 6

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
            20                  25                  30

Gln Asp Gln Glu Gly Asp Thr Asp Ala Gly Leu Lys Ala Glu Glu Ala
        35                  40                  45

Gly Ile Gly Asp Thr Pro Ser Leu Glu Asp Glu Ala Ala Gly His Val
    50                  55                  60

Thr Gln Ala Arg Met Val Ser Lys Ser Lys Asp Gly Thr Gly Ser Asp
65                  70                  75                  80

Asp Lys Lys Ala Lys Gly Ala Asp Gly Lys Thr Lys Ile Ala Thr Pro
                85                  90                  95

Arg Gly Ala Ala Pro Pro Gly Gln Lys Gly Gln Ala Asn Ala Thr Arg
            100                 105                 110

Ile Pro Ala Lys Thr Pro Pro Ala Pro Lys Thr Pro Pro Ser Ser Gly
        115                 120                 125

Glu Pro Pro Lys Ser Gly Asp Arg Ser Gly Tyr Ser Ser Pro Gly Ser
    130                 135                 140

Pro Gly Thr Pro Gly Ser Arg Ser Arg Thr Pro Ser Leu Pro Thr Pro
145                 150                 155                 160

Pro Thr Arg Glu Pro Lys Lys Val Ala Val Val Arg Thr Pro Pro Lys
                165                 170                 175

Ser Pro Ser Ser Ala Lys Ser Arg Leu Gln Thr Ala Pro Val Pro Met
            180                 185                 190

Pro Asp Leu Lys Asn Val Lys Ser Lys Ile Gly Ser Thr Glu Asn Leu
        195                 200                 205

Lys His Gln Pro Gly Gly Gly Lys Val Gln Ile Val Tyr Lys Pro Val
    210                 215                 220

Asp Leu Ser Lys Val Thr Ser Lys Cys Gly Ser Leu Gly Asn Ile His
225                 230                 235                 240

His Lys Pro Gly Gly Gly Gln Val Glu Val Lys Ser Glu Lys Leu Asp
                245                 250                 255

Phe Lys Asp Arg Val Gln Ser Lys Ile Gly Ser Leu Asp Asn Ile Thr
            260                 265                 270

His Val Pro Gly Gly Gly Asn Lys Lys Ile Gly Thr His Lys Leu Thr
        275                 280                 285

Phe Arg Glu Asn Ala Lys Ala Lys Thr Asp His Gly Ala Glu Ile Val
```

```
                    290                 295                 300

Tyr Lys Ser Pro Val Val Ser Gly Asp Thr Ser Pro Arg His Leu Ser
305                 310                 315                 320

Asn Val Ser Ser Thr Gly Ser Ile Asp Met Val Asp Ser Pro Gln Leu
                    325                 330                 335

Ala Thr Leu Ala Asp Glu Val Ser Ala Ser Leu Ala Lys Gln Gly Leu
                    340                 345                 350

<210> SEQ ID NO 7
<211> LENGTH: 121
<212> TYPE: PRT
<213> ORGANISM: artificial sequence
<220> FEATURE:
<223> OTHER INFORMATION: variable region of the heavy chain

<400> SEQUENCE: 7

Gln Val Gln Leu Gln Gln Pro Gly Ala Glu Leu Val Met Pro Gly Ala
1               5                   10                  15

Ser Val Lys Leu Ser Cys Lys Ala Ser Gly Tyr Thr Phe Thr Ser Tyr
                20                  25                  30

Trp Met His Trp Val Lys Gln Arg Pro Gly Gln Gly Leu Glu Trp Ile
            35                  40                  45

Gly Glu Ile Asp Pro Ser Asp Ser Tyr Thr Asn Tyr Asn Gln Lys Phe
        50                  55                  60

Lys Gly Lys Ser Thr Leu Thr Val Asp Lys Pro Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Gly Asp Gly Ser Ser Pro Trp Tyr Phe Asp Val Trp Gly
                100                 105                 110

Thr Gly Thr Thr Val Thr Val Ser Ser
            115                 120

<210> SEQ ID NO 8
<211> LENGTH: 112
<212> TYPE: PRT
<213> ORGANISM: artificial sequence
<220> FEATURE:
<223> OTHER INFORMATION: variable region of the light chain

<400> SEQUENCE: 8

Asp Ile Val Met Thr Gln Ser Thr Leu Ser Leu Pro Val Ser Leu Gly
1               5                   10                  15

Asp Gln Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Lys Leu Leu Ile Tyr Lys Val Ser Asn Arg Phe Ser Gly Val Pro
        50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Arg Thr Phe Gly Gly Gly Thr Lys Leu Glu Ile Lys
                100                 105                 110

<210> SEQ ID NO 9
<211> LENGTH: 363
<212> TYPE: DNA
```

```
<213> ORGANISM: artificial sequence
<220> FEATURE:
<223> OTHER INFORMATION: DNA encoding VH

<400> SEQUENCE: 9
caggtccaac tgcagcagcc tggggctgag cttgtgatgc ctggggcttc agtgaagctg      60
tcctgcaagg cttctggcta caccttcacc agctactgga tgcactgggt gaagcagagg     120
cctggacaag ccttgagtg gatcggagag attgatcctt ctgatagtta tactaactac     180
aatcaaaagt tcaagggcaa gtccacattg actgtagaca aaccctccag cacagcctac     240
atgcagctca gcagcctgac atctgaggac tctgcggtct attactgtgc aagaagtggg     300
gacggtagta gccccctggta cttcgatgtc tggggcacag ggaccacggt caccgtctcc     360
tca                                                                   363

<210> SEQ ID NO 10
<211> LENGTH: 336
<212> TYPE: DNA
<213> ORGANISM: artificial sequence
<220> FEATURE:
<223> OTHER INFORMATION: DNA encoding VL of antibody

<400> SEQUENCE: 10
gatattgtga tgacacagtc tacactctcc ctgcctgtca gtcttggaga tcaagcctcc      60
atctcttgca gatctagtca gagcattgta catagtaatg gaaacaccta tttagaatgg     120
tacctgcaga aaccaggcca gtctccaaag ctcctgatct acaaagtttc caaccgattt     180
tctggggtcc cagacaggtt cagtggcagt ggatcaggga cagatttcac actcaagatc     240
agcagagtgg aggctgagga tctgggagtt tattactgct ttcaaggttc acatgttcct     300
cggacgttcg gtggaggcac caagctggaa atcaaa                               336

<210> SEQ ID NO 11
<211> LENGTH: 1788
<212> TYPE: DNA
<213> ORGANISM: Artificial Sequence
<220> FEATURE:
<223> OTHER INFORMATION: Heavy Chain: DNA Segment

<400> SEQUENCE: 11
atgggatgga gctgtatcat cctcttcttg gtatcaacag ctacaggtgt ccactcccag      60
gtccaactgc agcagcctgg ggctgagctt gtgatgcctg ggcttcagt gaagctgtcc     120 tgcaaggctt ctggctacac cttcaccagc tactggatgc actgggtgaa gcagaggcct     180
ggacaaggcc ttgagtggat cggagagatt gatccttctg atagttatac taactacaat     240
caaaagttca gggcaagtc cacattgact gtagacaaat cctccagcac agcctacatg     300
cagctcagca gcctgacatc tgaggactct gcggtctatt actgtgcaag aagtggggac     360
ggtagtagcc cctggtactt cgatgtctgg ggcacaggga ccacggtcac cgtctcctca     420
gagagtcagt ccttcccaaa tgtcttcccc ctcgtctcct gcgagagccc cctgtctgat     480
aagaatctgg tggccatggg ctgcctggcc cgggacttcc tgcccagcac catttccttc     540
acctggaact accagaacaa cactgaagtc atccagggta tcagaacctt cccaacactg     600
aggacagggg gcaagtacct agccacctcg caggtgttgc tgtctcccaa gagcatcctt     660
gaaggttcag atgaatacct ggtatgcaaa atccactacg gaggcaaaaa caaagatctg     720
catgtgccca ttccagctgt cgcagagatg aaccccaatg taaatgtgtt cgtcccacca     780
cgggatggct ctctctggcc ctgcaccacg caagtctaaa tcatctgcga ggccacgaac     840
```

-continued

```
ttcactccaa aaccgatcac agtatcctgg ctaaaggatg ggaagctcgt ggaatctggc    900
ttcaccacag atccggtgac catcgagaac aaaggatcca caccccaaac ctacaaggtc    960
ataagcacac ttaccatctc tgaaatcgac tggctgaacc tgaatgtgta cacctgccgt   1020
gtggatcaca ggggtctcac cttcttgaag aacgtgtcct ccacatgtgc tgccagtccc   1080
tccacagaca tcctaacctt caccatcccc ccctcctttg ccgacatctt cctcagcaag   1140
tccgctaacc tgacctgtct ggtctcaaac ctggcaacct atgaaaccct gaatatctcc   1200
tgggcttctc aaagtggtga accactggaa accaaaatta aaatcatgga agccatccc    1260 aatggcacct tcagtgctaa gggtgtggct agtgtttgtg tggaagactg gaataacagg   1320
aaggaatttg tgtgtactgt gactcacagg gatctgcctt caccacagaa gaaattcatc   1380
tcaaaaccca atgaggtgca caaacatcca cctgctgtgt acctgctgcc accagctcgt   1440
gagcaactga acctgaggga gtcagccaca gtcacctgcc tggtgaaggg cttctctcct   1500
gcagacatca gtgtgcagtg gcttcagaga gggcaactct tgcccccaaga gaagtatgtg   1560 accagtgccc cgatgccaga gcctggggcc ccaggcttct actttaccca cagcatcctg   1620
actgtgacag aggaggaatg gaactccgga gagacctata cctgtgttgt aggccacgag   1680
gccctgccac acctggtgac cgagaggacc gtggacaagt ccactggtaa acccacactg   1740
tacaatgtct ccctgatcat gtctgacaca ggcggcacct gctattga                1788
```

```
<210> SEQ ID NO 12
<211> LENGTH: 595
<212> TYPE: PRT
<213> ORGANISM: Artificial Sequence
<220> FEATURE:
<223> OTHER INFORMATION: Heavy Chain: Amino Acid Sequence

<400> SEQUENCE: 12

Met Gly Trp Ser Cys Ile Ile Leu Phe Leu Val Ser Thr Ala Thr Gly
1               5                   10                  15

Val His Ser Gln Val Gln Leu Gln Gln Pro Gly Ala Glu Leu Val Met
                20                  25                  30

Pro Gly Ala Ser Val Lys Leu Ser Cys Lys Ala Ser Gly Tyr Thr Phe
            35                  40                  45

Thr Ser Tyr Trp Met His Trp Val Lys Gln Arg Pro Gly Gln Gly Leu
        50                  55                  60

Glu Trp Ile Gly Glu Ile Asp Pro Ser Asp Ser Tyr Thr Asn Tyr Asn
65                  70                  75                  80

Gln Lys Phe Lys Gly Lys Ser Thr Leu Thr Val Asp Lys Ser Ser Ser
                85                  90                  95

Thr Ala Tyr Met Gln Leu Ser Ser Leu Thr Ser Glu Asp Ser Ala Val
                100                 105                 110

Tyr Tyr Cys Ala Arg Ser Gly Asp Gly Ser Ser Pro Trp Tyr Phe Asp
            115                 120                 125

Val Trp Gly Thr Gly Thr Thr Val Thr Val Ser Ser Glu Ser Gln Ser
        130                 135                 140

Phe Pro Asn Val Phe Pro Leu Val Ser Cys Glu Ser Pro Leu Ser Asp
145                 150                 155                 160

Lys Asn Leu Val Ala Met Gly Cys Leu Ala Arg Asp Phe Leu Pro Ser
                165                 170                 175

Thr Ile Ser Phe Thr Trp Asn Tyr Gln Asn Asn Thr Glu Val Ile Gln
            180                 185                 190

Gly Ile Arg Thr Phe Pro Thr Leu Arg Thr Gly Gly Lys Tyr Leu Ala
        195                 200                 205
```

Thr Ser Gln Val Leu Leu Ser Pro Lys Ser Ile Leu Glu Gly Ser Asp
    210                 215                 220

Glu Tyr Leu Val Cys Lys Ile His Tyr Gly Gly Lys Asn Lys Asp Leu
225                 230                 235                 240

His Val Pro Ile Pro Ala Val Ala Glu Met Asn Pro Asn Val Asn Val
                245                 250                 255

Phe Val Pro Pro Arg Asp Gly Phe Ser Gly Pro Ala Pro Arg Lys Ser
                260                 265                 270

Lys Leu Ile Cys Glu Ala Thr Asn Phe Thr Pro Lys Pro Ile Thr Val
            275                 280                 285

Ser Trp Leu Lys Asp Gly Lys Leu Val Glu Ser Gly Phe Thr Thr Asp
    290                 295                 300

Pro Val Thr Ile Glu Asn Lys Gly Ser Thr Pro Gln Thr Tyr Lys Val
305                 310                 315                 320

Ile Ser Thr Leu Thr Ile Ser Glu Ile Asp Trp Leu Asn Leu Asn Val
                325                 330                 335

Tyr Thr Cys Arg Val Asp His Arg Gly Leu Thr Phe Leu Lys Asn Val
                340                 345                 350

Ser Ser Thr Cys Ala Ala Ser Pro Ser Thr Asp Ile Leu Thr Phe Thr
            355                 360                 365

Ile Pro Pro Ser Phe Ala Asp Ile Phe Leu Ser Lys Ser Ala Asn Leu
    370                 375                 380

Thr Cys Leu Val Ser Asn Leu Ala Thr Tyr Glu Thr Leu Asn Ile Ser
385                 390                 395                 400

Trp Ala Ser Gln Ser Gly Glu Pro Leu Glu Thr Lys Ile Lys Ile Met
                405                 410                 415

Glu Ser His Pro Asn Gly Thr Phe Ser Ala Lys Gly Val Ala Ser Val
                420                 425                 430

Cys Val Glu Asp Trp Asn Asn Arg Lys Glu Phe Val Cys Thr Val Thr
            435                 440                 445

His Arg Asp Leu Pro Ser Pro Gln Lys Lys Phe Ile Ser Lys Pro Asn
    450                 455                 460

Glu Val His Lys His Pro Pro Ala Val Tyr Leu Leu Pro Pro Ala Arg
465                 470                 475                 480

Glu Gln Leu Asn Leu Arg Glu Ser Ala Thr Val Thr Cys Leu Val Lys
                485                 490                 495

Gly Phe Ser Pro Ala Asp Ile Ser Val Gln Trp Leu Gln Arg Gly Gln
                500                 505                 510

Leu Leu Pro Gln Glu Lys Tyr Val Thr Ser Ala Pro Met Pro Glu Pro
            515                 520                 525

Gly Ala Pro Gly Phe Tyr Phe Thr His Ser Ile Leu Thr Val Thr Glu
    530                 535                 540

Glu Glu Trp Asn Ser Gly Glu Thr Tyr Thr Cys Val Val Gly His Glu
545                 550                 555                 560

Ala Leu Pro His Leu Val Thr Glu Arg Thr Val Asp Lys Ser Thr Gly
                565                 570                 575

Lys Pro Thr Leu Tyr Asn Val Ser Leu Ile Met Ser Asp Thr Gly Gly
                580                 585                 590

Thr Cys Tyr
        595

<210> SEQ ID NO 13
<211> LENGTH: 717
<212> TYPE: DNA

<213> ORGANISM: Artificial Sequence
<220> FEATURE:
<223> OTHER INFORMATION: Light Chain DNA sequence

<400> SEQUENCE: 13

```
atgaagttgc ctgttaggct gttggtgctg atgttctgga ttcctgcttc cagcagtgat      60
gttttgatga cccaaactcc actctccctg cctgtcagtc ttggagatca agcctccatc     120
tcttgcagat ctagtcagag cattgtacat agtaatggaa acacctattt agaatggtac     180
ctgcagaaac caggccagtc tccaaagctc ctgatctaca agtttccaac cgattttct      240
ggggtcccag acaggttcag tggcagtgga tcagggacag atttcacact caagatcagc     300
agagtggagg ctgaggatct gggagtttat tactgctttc aaggttcaca tgttcctcgg     360
acgttcggtg aggcaccaa gctggaaatc aaacgggctg atgctgcacc aactgtatcc     420
atcttcccac catccagtga gcagttaaca tctggaggtg cctcagtcgt gtgcttcttg     480
aacaacttct accccaaaga catcaatgtc aagtggaaga ttgatggcag tgaacgacaa     540
aatggcgtcc tgaacagttg gactgatcag gacagcaaag acagcaccta cagcatgagc     600
agcaccctca cgttgaccaa ggacgagtat aacgacata acagctatac ctgtgaggcc     660
actcacaaga catcaacttc acccattgtc aagagcttca caggaatga gtgttag        717
```

<210> SEQ ID NO 14
<211> LENGTH: 238
<212> TYPE: PRT
<213> ORGANISM: Artificial Sequence
<220> FEATURE:
<223> OTHER INFORMATION: Light Chain Amino acid sequence

<400> SEQUENCE: 14

```
Met Lys Leu Pro Val Arg Leu Leu Val Leu Met Phe Trp Ile Pro Ala
 1               5                  10                  15

Ser Ser Ser Asp Val Leu Met Thr Gln Thr Pro Leu Ser Leu Pro Val
            20                  25                  30

Ser Leu Gly Asp Gln Ala Ser Ile Ser Cys Arg Ser Ser Gln Ser Ile
        35                  40                  45

Val His Ser Asn Gly Asn Thr Tyr Leu Glu Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser His Val Pro Arg Thr Phe Gly Gly Gly Thr Lys Leu
        115                 120                 125

Glu Ile Lys Arg Ala Asp Ala Ala Pro Thr Val Ser Ile Phe Pro Pro
    130                 135                 140

Ser Ser Glu Gln Leu Thr Ser Gly Gly Ala Ser Val Val Cys Phe Leu
145                 150                 155                 160

Asn Asn Phe Tyr Pro Lys Asp Ile Asn Val Lys Trp Lys Ile Asp Gly
                165                 170                 175

Ser Glu Arg Gln Asn Gly Val Leu Asn Ser Trp Thr Asp Gln Asp Ser
            180                 185                 190

Lys Asp Ser Thr Tyr Ser Met Ser Ser Thr Leu Thr Leu Thr Lys Asp
        195                 200                 205

Glu Tyr Glu Arg His Asn Ser Tyr Thr Cys Glu Ala Thr His Lys Thr
```

```
                210                 215                 220
Ser Thr Ser Pro Ile Val Lys Ser Phe Asn Arg Asn Glu Cys
225                 230                 235

<210> SEQ ID NO 15
<211> LENGTH: 14
<212> TYPE: PRT
<213> ORGANISM: tetanus toxin bacteria

<400> SEQUENCE: 15

Gln Tyr Ile L

```
<210> SEQ ID NO 22
<211> LENGTH: 16
<212> TYPE: PRT
<213> ORGANISM: Tetanus toxin bacteria

<400> SEQUENCE: 22

Tyr Asp Pro Asn Tyr Leu Arg Thr Asp Ser Asp Lys Asp Arg Phe Leu
1               5                   10                  15

<210> SEQ ID NO 23
<211> LENGTH: 24
<212> TYPE: PRT
<213> ORGANISM: Pertussis toxin bacteria

<400> SEQUENCE: 23

Gly Ala Tyr Ala Arg Cys Pro Asn Gly Thr Arg Ala Leu Thr Val Ala
1               5                   10                  15

Glu Leu Arg Gly Asn Ala Glu Leu
            20

<210> SEQ ID NO 24
<211> LENGTH: 15
<212> TYPE: PRT
<213> ORGANISM: Measles virus

<400> SEQUENCE: 24

Leu Ser Glu Ile Lys Gly Val Ile Val His Arg Leu Glu Gly Val
1               5                   10                  15

<210> SEQ ID NO 25
<211> LENGTH: 20
<212> TYPE: PRT
<213> ORGANISM: measles virus

<400> SEQUENCE: 25

Gly Ile Leu Glu Ser Arg Gly Ile Lys Ala Arg Ile Thr His Val Ser
1               5                   10                  15

Thr Glu Ser Tyr
            20

<210> SEQ ID NO 26
<211> LENGTH: 16
<212> TYPE: PRT
<213> ORGANISM: Tetanus toxin bacteria

<400> SEQUENCE: 26

Trp Val Arg Asp Ile Ile Asp Asp Phe Thr Asn Glu Ser Ser Gln Lys
1               5                   10                  15

<210> SEQ ID NO 27
<211> LENGTH: 16
<212> TYPE: PRT
<213> ORGANISM: Tetanus toxin bacteria

<400> SEQUENCE: 27

Asp Val Ser Thr Ile Val Pro Tyr Ile Gly Pro Ala Leu Asn His Val
1               5                   10                  15

<210> SEQ ID NO 28
<211> LENGTH: 24
<212> TYPE: PRT
<213> ORGANISM: Clamydia trachomitis
```

```
<400> SEQUENCE: 28

Ala Leu Asn Ile Trp Asp Arg Phe Asp Val Phe Cys Thr Leu Gly Ala
1 5 10 15

Thr Thr Tyr Leu Lys Glu Asn Ser
20

<210> SEQ ID NO 29
<211> LENGTH: 23
<212> TYPE: PRT
<213> ORGANISM: Diphteria toxin bacteria

<400> SEQUENCE: 29

Asp Ser Glu Thr Ala Asp Asn Leu Glu Lys Thr Val Ala Ala Leu Ser
1 5 10 15

Ile Leu Pro Gly Ile Gly Cys
20

<210> SEQ ID NO 30
<211> LENGTH: 39
<212> TYPE: PRT
<213> ORGANISM: Diphteria toxin bacteria

<400> SEQUENCE: 30

Glu Glu Ile Val Ala Gln Ser Ile Ala Leu Ser Ser Leu Met Val Ala
1 5 10 15

Gln Ala Ile Pro Leu Val Gly Glu Leu Val Asp Ile Gly Phe Ala Ala
20 25 30

Thr Asn Phe Val Glu Ser Cys
35

<210> SEQ ID NO 31
<211> LENGTH: 21
<212> TYPE: PRT
<213> ORGANISM: Plasmodium falciparum

<400> SEQUENCE: 31

Asp Ile Glu Lys Lys Ile Ala Lys Met Glu Lys Ala Ser Ser Val Phe
1 5 10 15

Asn Val Val Asn Ser
20

<210> SEQ ID NO 32
<211> LENGTH: 16
<212> TYPE: PRT
<213> ORGANISM: Schistom mansoni

<400> SEQUENCE: 32

Lys Trp Phe Lys Thr Asn Ala Pro Asn Gly Val Asp Glu Lys Ile Arg
1 5 10 15

<210> SEQ ID NO 33
<211> LENGTH: 14
<212> TYPE: PRT
<213> ORGANISM: Escherichia coli

<400> SEQUENCE: 33

Gly Leu Gln Gly Lys Ile Ala Asp Ala Val Lys Ala Lys Gly
1 5 10

<210> SEQ ID NO 34
<211> LENGTH: 19
<212> TYPE: PRT
<213> ORGANISM: Escherichia coli

```
<400> SEQUENCE: 34

Gly Leu Ala Ala Gly Leu Val Gly Met Ala Ala Pro Ala Met Val Glu
1               5                   10                  15

Asp Val Asn

<210> SEQ ID NO 35
<211> LENGTH: 20
<212> TYPE: PRT
<213> ORGANISM: Escherichia coli

<400> SEQUENCE: 35

Ser Thr Glu Thr Gly Asn Gln His His Tyr Gln Thr Arg Val Val Ser
1               5                   10                  15

Asn Ala Asn Lys
            20
```